United States Patent
Poulos et al.

(10) Patent No.: US 10,093,949 B2
(45) Date of Patent: *Oct. 9, 2018

(54) PRODUCTION OF CANNABIDIOLIC ACID IN YEAST

(71) Applicant: Librede Inc., Sherman Oaks, CA (US)

(72) Inventors: Jason L. Poulos, Los Angeles, CA (US); Anthony N. Farnia, Pasadena, CA (US)

(73) Assignee: Librede Inc., Sherman Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/815,651

(22) Filed: Nov. 16, 2017

(65) Prior Publication Data

US 2018/0073043 A1 Mar. 15, 2018

Related U.S. Application Data

(63) Continuation of application No. 14/795,816, filed on Jul. 9, 2015, now Pat. No. 9,822,384.

(60) Provisional application No. 62/024,099, filed on Jul. 14, 2014.

(51) Int. Cl.
| | | |
|---|---|---|
| *C12P 7/42* | (2006.01) |
| *C12N 1/14* | (2006.01) |
| *C12N 15/00* | (2006.01) |
| *C12N 9/88* | (2006.01) |
| *C12N 9/10* | (2006.01) |
| *C12N 9/00* | (2006.01) |
| *C12N 15/81* | (2006.01) |

(52) U.S. Cl.
CPC .............. *C12P 7/42* (2013.01); *C12N 9/1029* (2013.01); *C12N 9/1085* (2013.01); *C12N 9/88* (2013.01); *C12N 9/93* (2013.01); *C12N 15/81* (2013.01); *C12Y 203/01206* (2015.07); *C12Y 205/01* (2013.01); *C12Y 504/99* (2013.01); *C12Y 602/01* (2013.01)

(58) Field of Classification Search
None
See application file for complete search history.

(56) References Cited

U.S. PATENT DOCUMENTS

| | | |
|---|---|---|
| 6,630,507 B1 | 10/2003 | Hampson et al. |
| 7,186,850 B2 | 3/2007 | Silverberg |
| 8,673,368 B2 | 3/2014 | Guy et al. |
| 8,884,100 B2 | 11/2014 | Page et al. |

(Continued)

FOREIGN PATENT DOCUMENTS

| | | |
|---|---|---|
| WO | WO2013006953 | 1/2013 |
| WO | WO2014134281 | 9/2014 |
| WO | WO2016010827 | 1/2016 |

OTHER PUBLICATIONS

Gagne, S.J. et al. Identification of olivetolic acid cyclase from Cannabis sativa reveals a unique catalytic route to plant polyketides. Proceedings of the National Academy of Sciences of the United States of America 109, 12811-12816 (2012).

(Continued)

*Primary Examiner* — Yong D Pak
(74) *Attorney, Agent, or Firm* — Carr & Ferrell LLP

(57) ABSTRACT

Exemplary embodiments provided herein include genetically engineering microorganisms, such as yeast or bacteria, to produce cannabinoids by inserting genes that produce the appropriate enzymes for the metabolic production of a desired compound.

1 Claim, 8 Drawing Sheets

Specification includes a Sequence Listing.

(56) References Cited

U.S. PATENT DOCUMENTS

| | | | |
|---|---|---|---|
| 9,611,460 B2* | 4/2017 | Page | C12N 9/1025 |
| 9,822,384 B2 | 11/2017 | Poulos et al. | |
| 2009/0226991 A1 | 9/2009 | Feldman et al. | |
| 2012/0144523 A1 | 6/2012 | Page et al. | |
| 2013/0067619 A1 | 3/2013 | Page et al. | |
| 2013/0210107 A1 | 8/2013 | Akada et al. | |
| 2014/0178954 A1 | 6/2014 | Hitz et al. | |
| 2016/0010126 A1 | 1/2016 | Poulos et al. | |

OTHER PUBLICATIONS

Stout, J.M., Boubakir, Z., Ambrose, S.J., Purves, R.W. & Page, J.E. The hexanoyl-CoA precursor for cannabinoid biosynthesis is formed by an acyl-activating enzyme in Cannabis sativa trichomes. The Plant Journal 71, 353-365 (2012).

Shoyama, Y. et al. Structure and function of 1-Tetrahydrocannabinolic Acid (THCA) synthase, the enzyme controlling the psychoactivity of cannabis sativa. J. Mol. Biol., 423 (1), 96-105 (2012).

ElSohly et al. Chemical constituents of marijuana: The complex mixture of natural cannabinoids. National Center for Natural Products Research, School of Pharmacy, The University of Mississippi, University, MS 38677. Life Sciences (78), 539-548 (2005).

Ignea et al. Engineering monoterpene production in yeast using a synthetic dominant negative geranyl diphosphate synthase. ACS Synth Biol, May 16, 2014. vol. 3, No. 5. pp. 298-306.

Fonseca et al. The yeast Kluyveromyces marxianus and its biotechnological potential. Appl Microbiol Biotechnol, Jun. 2008, vol. 79, No. 3, pp. 339-54.

International Search Report and Written Opinion dated Dec. 28, 2015 in Patent Cooperation Treaty Application No. PCT/US2015/039812, filed Jul. 9, 2015, 21 pages.

"Recombinase expression vector pSH68, complete sequence", GenBank entry HQ401270.1, [retrieved on Nov. 18, 2015 from http://www.ncbi.nlm.nih.gov/nuccore/HW401270] Sep. 12, 2011 (Sep. 12, 2011), 3 pages.

Written Opinion of the International Preliminary Examining Authority dated Jun. 24, 2016 in Patent Cooperation Treaty Application No. PCT/US2015/039812, filed Jul. 9, 2015, 5 pages.

Fischer, Marc et al., Metabolic Engineering of Monoterpene Synthesis in Year, Biotechnology and Bioengineering, vol. 108, No. 8, Aug. 2011, 10 pages.

* cited by examiner

PRODUCTION OF CANNABIDIOLIC ACID IN YEAST

CROSS-REFERENCE TO RELATED APPLICATIONS

This continuation application claims the priority benefit of U.S. Non-Provisional patent application Ser. No. 14/795,816 filed on Jul. 9, 2015 titled "Production of Cannabinoids in Yeast," which will issue on Nov. 21, 2017 as U.S. Pat. No. 9,822,384, which in turn claims the benefit and priority of U.S. Provisional Patent Application Ser. No. 62/024,099 filed Jul. 14, 2014, titled "Terpenophenolic Production in Microorganisms," which is incorporated by reference herein.

REFERENCE TO SEQUENCE LISTINGS

The present application is filed with sequence listing(s) attached hereto and incorporated by reference, including Appendix 1B titled "Sequence IDs".

FIELD OF THE INVENTION

This invention relates to molecular biology, and more specifically to the transformation of yeast cells and the production of cannabinoids.

SUMMARY OF THE INVENTION

Exemplary embodiments provided herein include genetically engineering microorganisms, such as yeast or bacteria, to produce cannabinoids by inserting genes that produce the appropriate enzymes for the metabolic production of a desired compound.

DETAILED DESCRIPTION OF EXEMPLARY EMBODIMENTS

Figure 1:
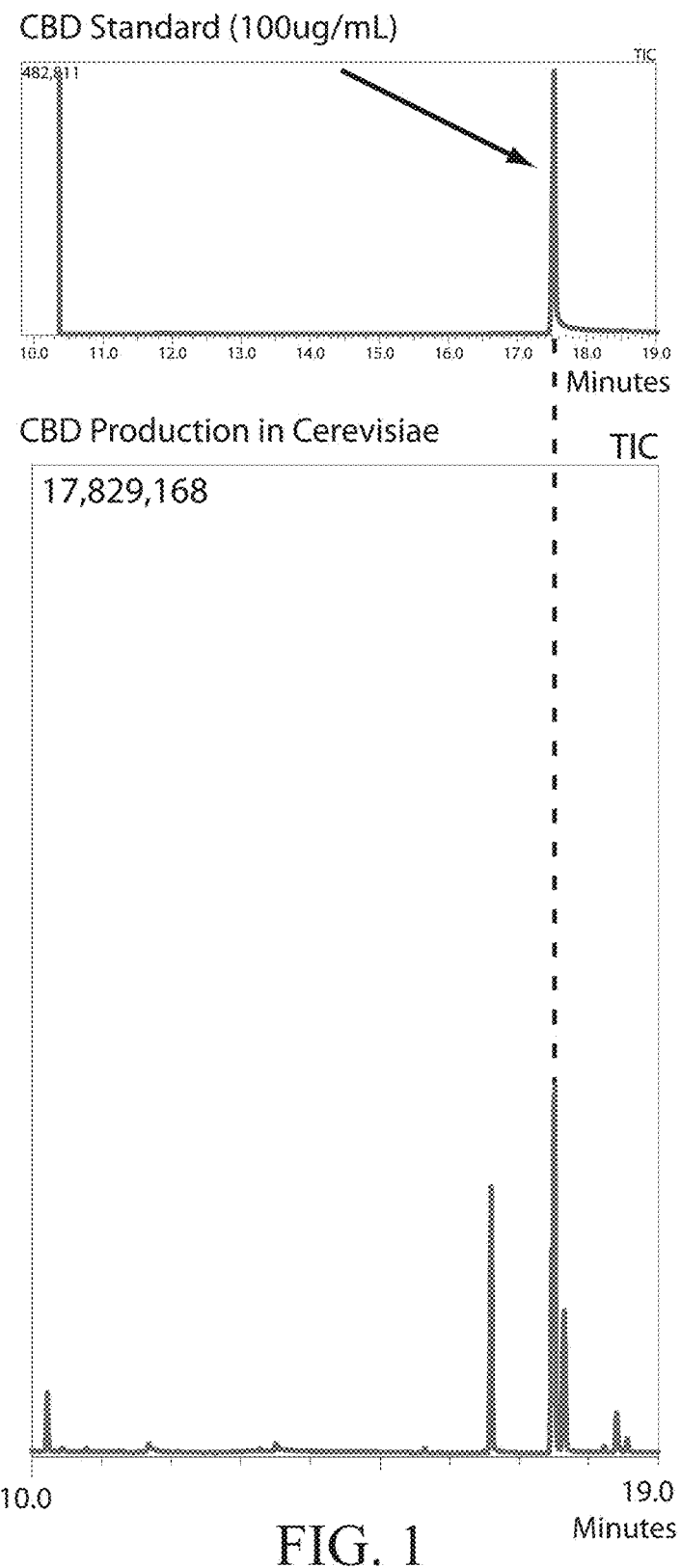
FIG. 1 shows exemplary experimental data achieved in connection with Example 1 of Appendix 1A titled "Additional Examples" for cannabidiol ("CBD")/cannabidiolic acid ("CBDA") production in *S. cerevisiae*.

The present application relates to the field of cannabinoid production in yeasts. Cannabinoids are a general class of chemicals that act on cannabinoid receptors and other target molecules to modulate a wide range of physiological behavior such as neurotransmitter release. Cannabinoids are produced naturally in humans (called endocannabinoids) and by several plant species (called phytocannabinoids) including *Cannabis sativa*. Cannabinoids have been shown to have several beneficial medical/therapeutic effects and therefore they are an active area of investigation by the pharmaceutical industry for use as pharmaceutical products for various diseases.

Currently the production of cannabinoids for pharmaceutical or other use is done by chemical synthesis or through the extraction of cannabinoids from plants that are producing these cannabinoids, for example *Cannabis sativa*. There are several drawbacks to the current methods of cannabinoid production. The chemical synthesis of various cannabinoids is a costly process when compared to the extraction of cannabinoids from naturally occurring plants. The chemical synthesis of cannabinoids also involves the use of chemicals that are not environmentally friendly, which can be considered as an additional cost to their production. Furthermore, the synthetic chemical production of various cannabinoids has been classified as less pharmacologically active as those extracted from plants such as *Cannabis sativa*. Although there are drawbacks to chemically synthesized cannabinoids, the benefit of this production method is that the end product is a highly pure single cannabinoid. This level of purity is preferred for pharmaceutical use. The level of purity required by the pharmaceutical industry is reflected by the fact that no plant extract based cannabinoid production has received FDA approval yet and only synthetic compounds have been approved.

In contrast to the synthetic chemical production of cannabinoids, the other method that is currently used to produce cannabinoids is production of cannabinoids in plants that naturally produce these chemicals; the most used plant for this is *Cannabis sativa*. In this method, the plant *Cannabis sativa* is cultivated and during the flowering cycle various cannabinoids are produced naturally by the plant. The plant can be harvested and the cannabinoids can be ingested for pharmaceutical purposes in various methods directly from the plant itself or the cannabinoids can be extracted from the plant. There are multiple methods to extract the cannabinoids from the plant *Cannabis sativa*. All of these methods typically involve placing the plant, *Cannabis sativa* that contains the cannabinoids, into a chemical solution that selectively solubilizes the cannabinoids into this solution. There are various chemical solutions used to do this such as hexane, cold water extraction methods, $CO_2$ extraction methods, and others. This chemical solution, now containing all the different cannabinoids, can then be removed, leaving behind the excess plant material. The cannabinoid containing solution can then be further processed for use.

There are several drawbacks of the natural production and extraction of cannabinoids in plants such as *Cannabis sativa*. Since there are numerous cannabinoids produced by *Cannabis sativa* it is often difficult to reproduce identical cannabinoid profiles in plants using an extraction process. Furthermore, variations in plant growth will lead to different levels of cannabinoids in the plant itself making reproducible extraction difficult. Different cannabinoid profiles will have different pharmaceutical effects which are not desired for a pharmaceutical product. Furthermore, the extraction of cannabinoids from *Cannabis sativa* extracts produces a mixture of cannabinoids and not a highly pure single pharmaceutical compound. Since many cannabinoids are similar in structure it is difficult to purify these mixtures to a high level resulting in cannabinoid contamination of the end product.

Disclosed herein are strategies for creating cannabinoids in microorganisms such as yeast and methods to produce various cannabinoids in yeast from a simple sugar source. The general methods involve genetically engineering yeast to produce various cannabinoids, where the main carbon source available to the yeast is a sugar (glucose, galactose, fructose, sucrose, honey, molasses, raw sugar, etc.). Genetic engineering of the microorganism involves inserting various genes that produce the appropriate enzymes and/or altering the natural metabolic pathway in the microorganism to achieve the production of a desired compound. Through genetic engineering of microorganisms these metabolic pathways can be introduced into these microorganisms and the same metabolic products that are produced in the plant *Cannabis sativa* can be produced by the microorganisms. The benefit of this method is that once the microorganism is produced, the production of the cannabinoid is low cost and reliable, only a specific cannabinoid is produced or a subset is produced, depending on the organism. The purification of the cannabinoid is straight forward since there is only a single cannabinoid or a selected few cannabinoids present in the microorganism. The process is a sustainable process which is more environmentally friendly than synthetic production.

FIG. 1 shows exemplary experimental data achieved in connection with Example 1 of Appendix 1A titled "Additional Examples" for cannabidiol ("CBD")/cannabidiolic acid ("CBDA") production in *S. cerevisiae*.

FIG. 1 shows gas chromatography—mass spectrometry of cannabidiol (CBD) produced in *S. cervisiae*. After processing the yeast cells, as described in Example 1 of Appendix 1A, the whole cell ethyl acetate extract is analyzed for the presences of CBD. The samples were prepared in a way similar to that shown in Appendix A1 except that no MSTFA derivatization was used in this sample (therefore CBDA turns into CBD upon heating), the oven protocol was also slightly different than that shown in Appendix 1A. Initially, a standard CBD solution is run (100 ug/mL; TOP). After running the standard the inventors determined the run time of 17.5 minutes. After running the standard the inventors repeated the GC-MS experiment with their whole cell extract (BOTTOM). At a run time of 17.5 minutes, the inventors saw the same peak as in the standard. Mass spectrometry analysis of the peaks showed identical mass for the two samples (standard and extract) indicating the presence of CBD in their whole cell extract.

Figure 2:
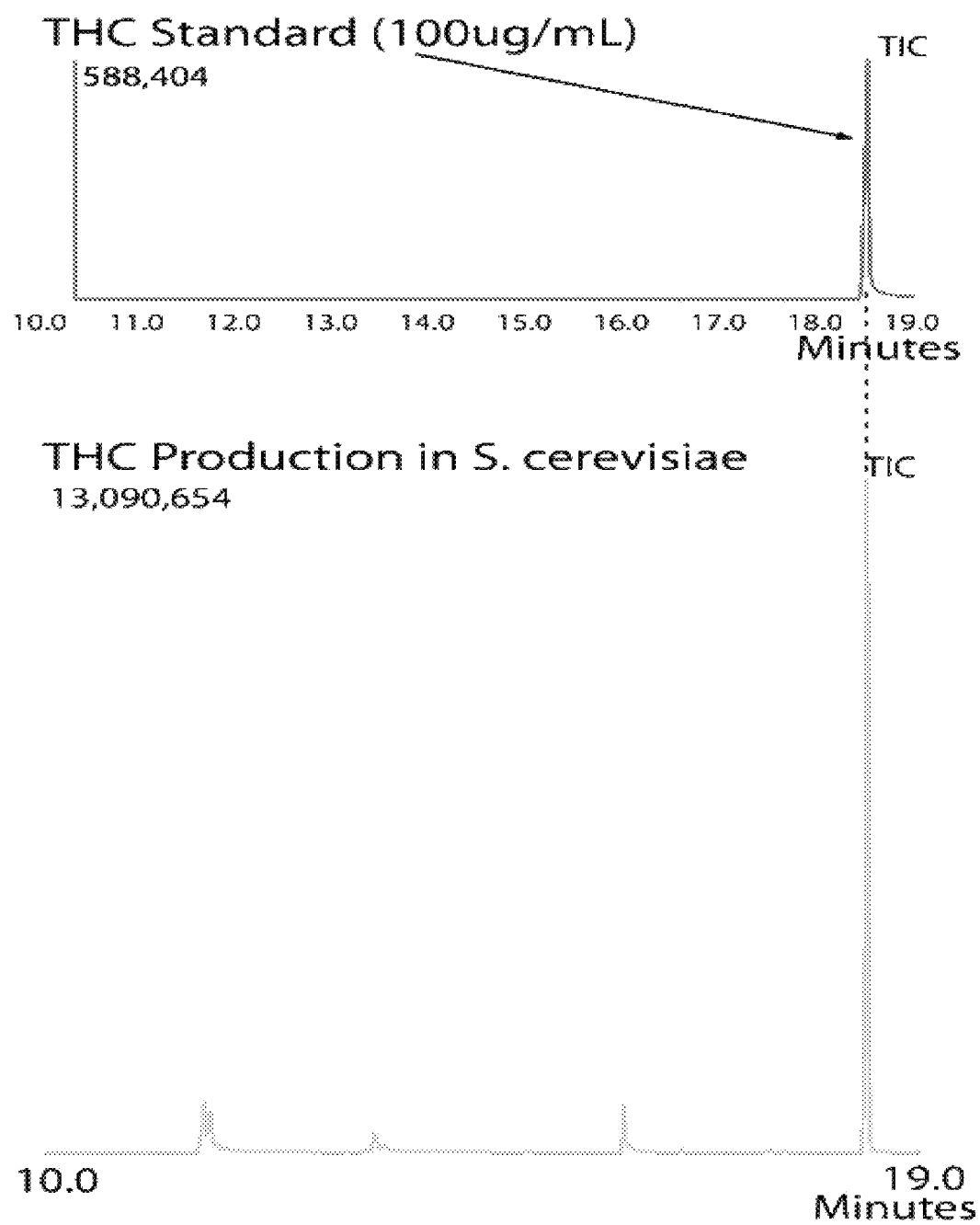
FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae*.

FIG. 2 shows exemplary experimental data achieved in connection with Example 2 of Appendix 1A titled "Additional Examples" for tetrahydrocannabinol ("THC")/tetrahydrocannabinolic acid ("THCA") production in *S. cerevisiae*.

FIG. 2 shows gas chromatography—mass spectrometry of tetrahydrocannabinol (THC) produced in *S. cervisiae*. After processing the yeast cells, as described in Example 2 of Appendix 1A, the whole cell ethyl acetate extract was analyzed for the presences of THC. The samples were prepared in a way similar to that shown in Appendix 1A except that no MSTFA derivatization was used in this sample (therefore THCA turns into THC upon heating), the oven protocol was also slightly different than that shown in Appendix 1A. Initially, a standard CBD solution was run (100 ug/mL; TOP). After running the standard the inventors determined the run time of 18.5 minutes. After running the standard the inventors repeated the GC-MS experiment with their whole cell extract (BOTTOM). At a run time of 18.5 minutes, the inventors saw the same peak as in the standard. Mass spectrometry analysis of the peaks showed identical mass for the two samples (standard and extract) indicating the presence of THC in their whole cell extract.

Figure 3:
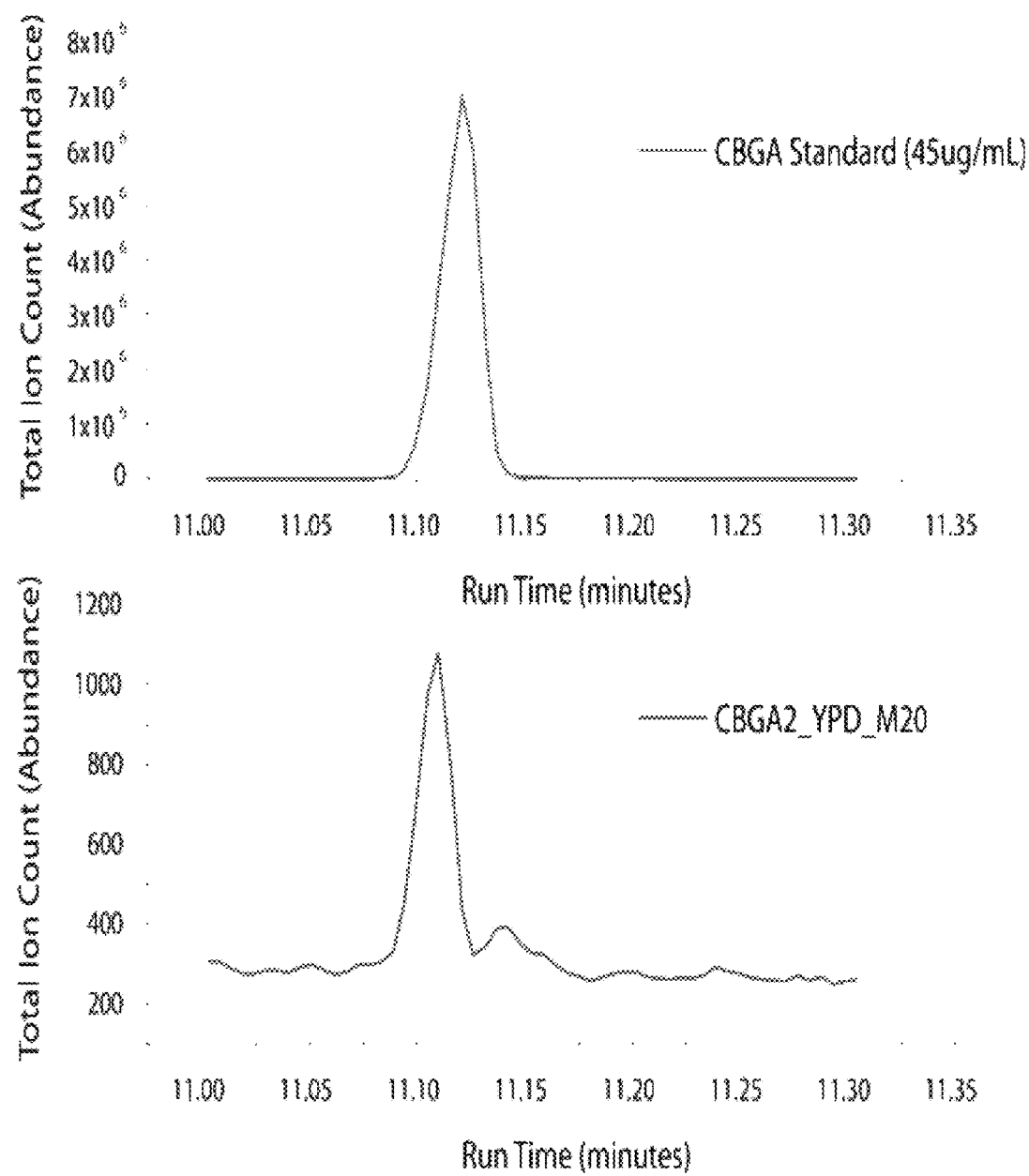
FIG. 3 shows exemplary experimental data achieved in connection with Example 3 of Appendix 1A titled "Additional Examples" for cannabigerol ("CBG")/cannabigerolic acid ("CBGA") production in *S. cerevisiae*.

FIG. 3 shows exemplary experimental data achieved in connection with Example 3 of Appendix 1A titled "Additional Examples" for cannabigerol ("CBG")/cannabigerolic acid ("CBGA") production in *S. cerevisiae*.

FIG. 3 shows gas chromatography—mass spectrometry of cannabigerolic acid (CBGA) produced in *S. cervisiae*. After processing the yeast cells, as described in Example 3 of Appendix 1A, the whole cell ethyl acetate extract was analyzed for the presences of CBGA. The samples were prepared in a way as described in Appendix 1A, but the oven protocol was also slightly different than that shown in Appendix 1A. Initially, a standard CBGA solution was run (45 ug/mL; TOP). After running the standard, the inventors determined the run time of 11.1 minutes. After running the standard, the inventors repeated the GC-MS experiment with their whole cell extract (BOTTOM). At a run time of 11.1 minutes, the inventors saw the same peak as in the standard. Mass spectrometry analysis of the peaks showed identical mass for the two samples (standard and extract) indicating the presence of CBGA in their whole cell extract.

Figure 4:
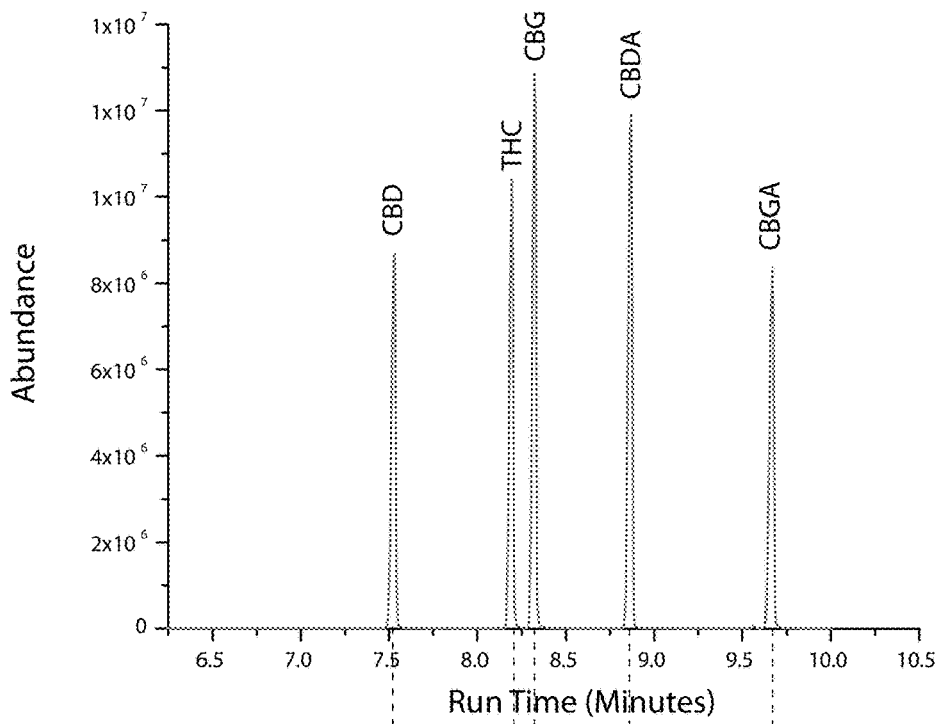
FIG. 4 shows exemplary experimental data achieved in connection with Example 4 of Appendix 1A titled "Additional Examples" for CBGA, CBDA, CBD, CBG and THC production in *K. marxianus*.
Figure 4:
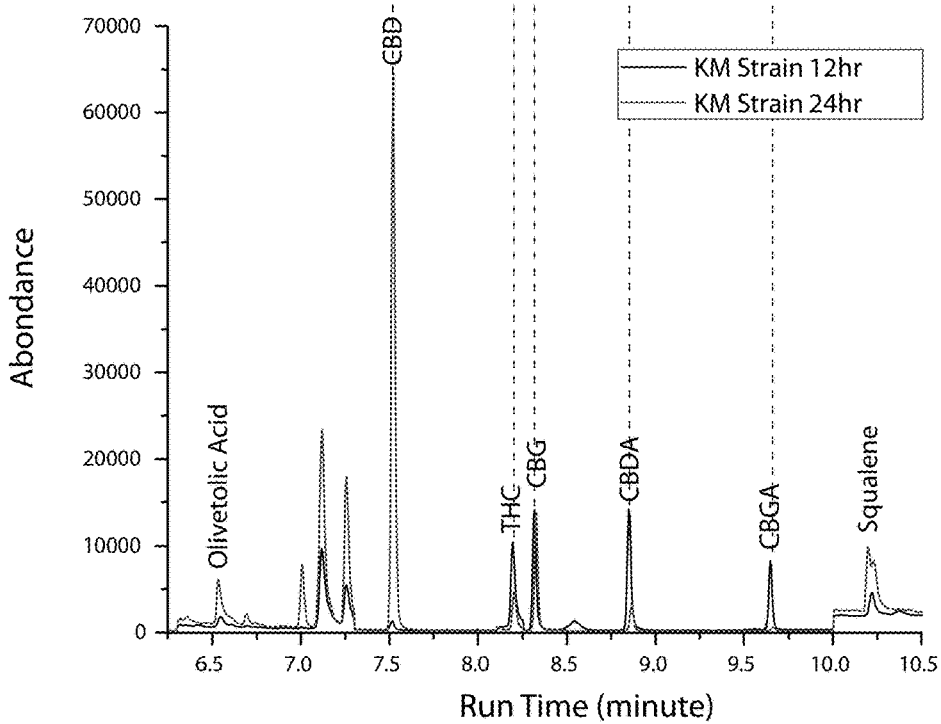

FIG. 4 shows exemplary experimental data achieved in connection with Example 4 of Appendix 1A titled "Additional Examples" for CBGA, CBDA, CBD, CBG and THC production in *K. marxianus*.

FIG. 4 shows gas chromatography—mass spectrometry of cannabinoid production (CBGA, CBDA, CBD, CBG, THC) produced in *K. marxianus*. After processing the yeast cells, as described in Example 4 of Appendix 1A, the whole cell ethyl acetate extract was analyzed for the presence of cannabinoids. The samples were prepared in a way as described in Appendix 1A, but the oven protocol was also slightly different than that shown in Appendix 1A. Initially, a standard solution containing CBD, CBG, THC, CBDA, and CBGA was run (70 ug/mL each; TOP). After running the standard, the inventors determined the run time for each compounds. After running the standard, the inventors repeated the GC-MS experiment with their whole cell extract (BOTTOM). At each run time the inventors saw the same peaks as in the standard. Mass spectrometry analysis of the peaks showed identical mass for the two samples (standard and extract) indicating the presence of cannabinoids in their whole cell extract.

Figure 5:
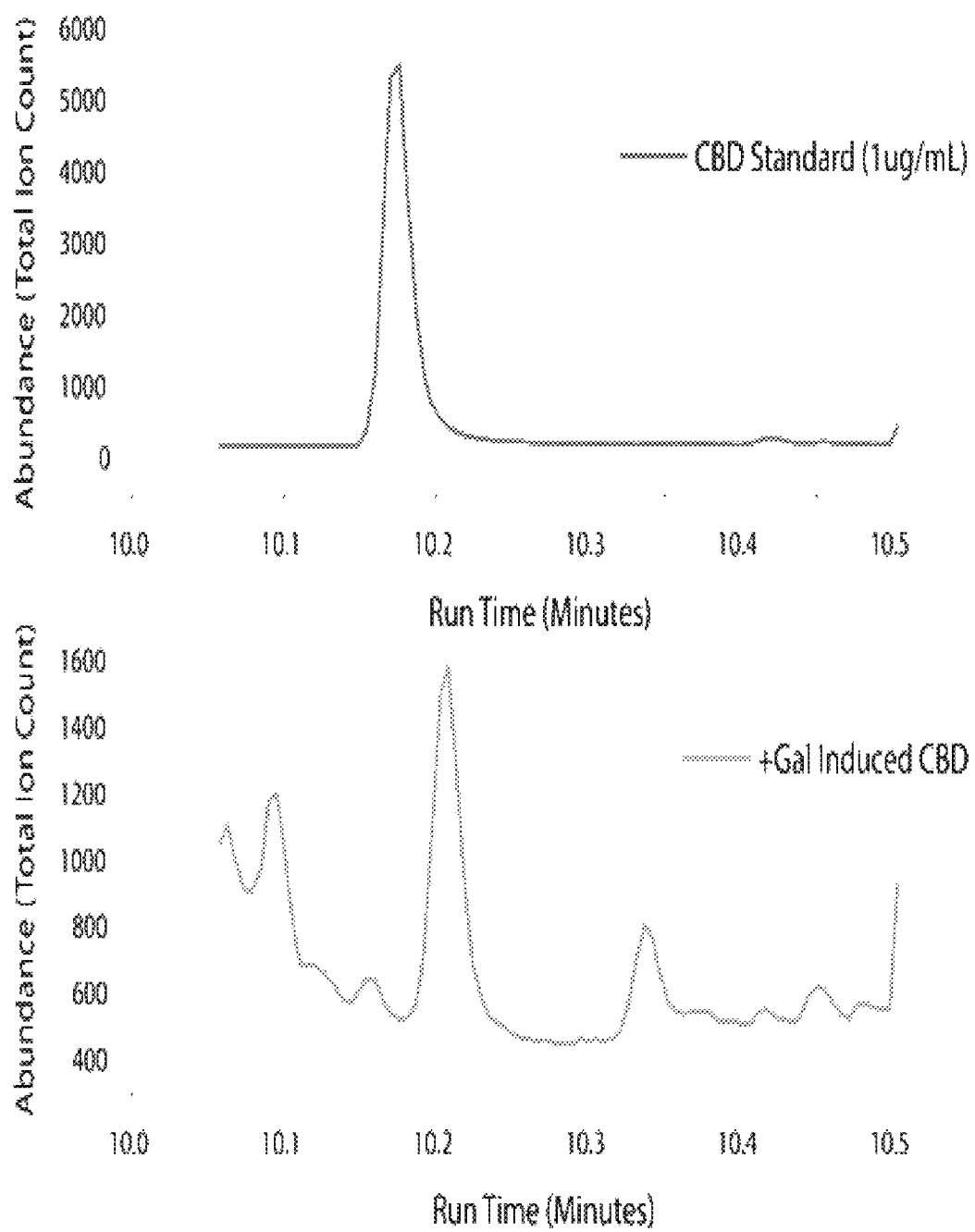
FIG. 5 show exemplary experimental data achieved in connection with Example 5 of Appendix 1A titled "Additional Examples" for galactose induced CBD production in *S. cerevisiae*.

FIG. 5 show exemplary experimental data achieved in connection with Example 5 of Appendix 1A titled "Additional Examples" for galactose induced CBD production in *S. cerevisiae*.

FIG. 5 shows gas chromatography—mass spectrometry of induced cannabidiol (CBD) production in *S. cervisiae*. After processing yeast cells, as described in Example 5 of Appendix 1A, the whole cell ethyl acetate extract was analyzed for the presences of CBD. The samples were prepared in a way as described in Appendix 1A. Initially, a standard solution containing CBD was run (1 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Figure 6:
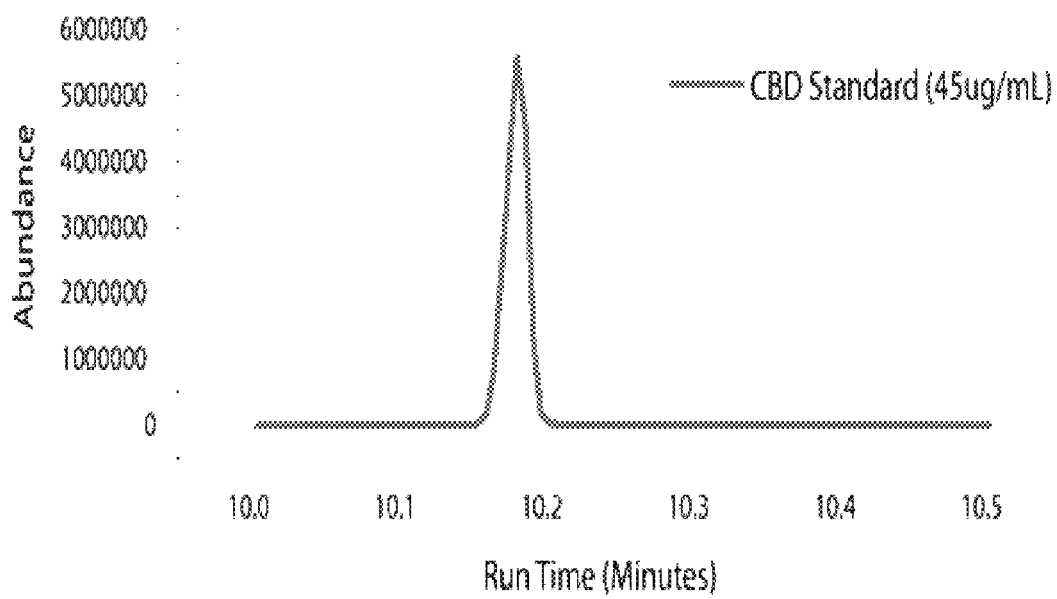
FIG. 6 shows exemplary experimental data achieved in connection with Example 6 of Appendix 1A titled "Additional Examples" for secretion of CBD into media by *S. cerevisiae*.
Figure 6:
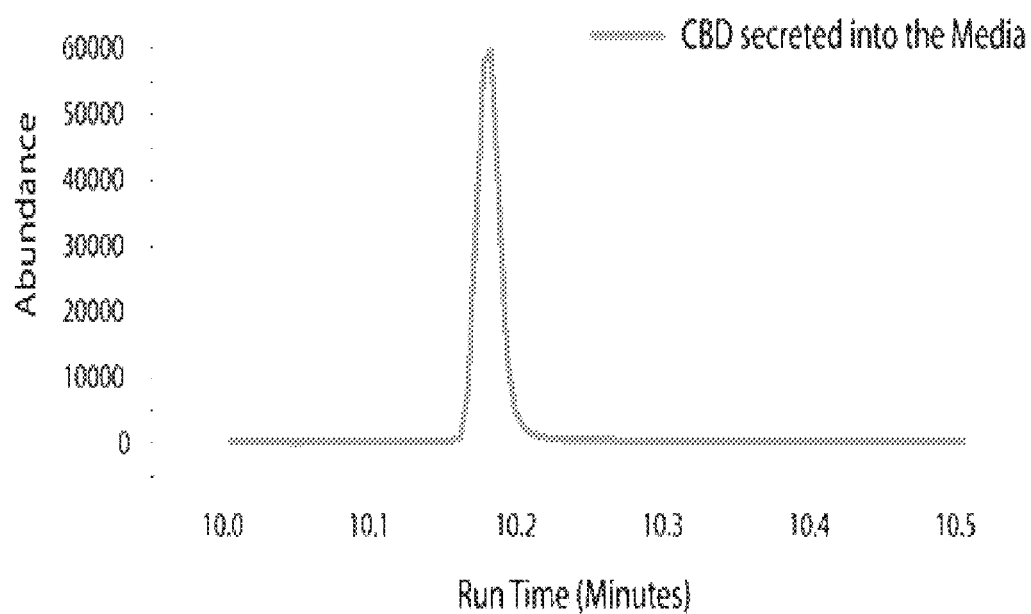

FIG. 6 shows exemplary experimental data achieved in connection with Example 6 of Appendix 1A titled "Additional Examples" for secretion of CBD into media by *S. cerevisiae*.

FIG. 6 shows gas chromatography—mass spectrometry of induced cannabidiol production (CBD) produced in *S. cervisiae* and secreted into the media. After processing the growth media, as described in Example 6 of Appendix 1A, the media ethyl acetate extract was analyzed for the presence of CBD. The samples were prepared in a way as described in Appendix 1A. Initially, a standard solution containing CBD was run (45 ug/mL; TOP). After running the standard the inventors determined the run time for CBD as 10.2 minutes. After running the standard, the inventors repeated the GC-MS experiment with their whole cell extract (BOTTOM). At 10.2 minutes, the inventors saw the same peak as in the standard. Mass spectrometry analysis of the peaks showed identical mass for the two samples (standard and extract) indicating the presence of CBD in their whole cell extract.

Biosynthetic Production of Cannabidiolic Acid (CBDA) in *S. cerevisiae*

Through genetic engineering the inventors have reconstituted the cannabidiolic acid (CBDA) metabolic pathway found in *Cannabis sativa* into *S. cerevisiae* (a species of yeast).

Producing CBGA is an initial step in producing many cannabinoids from *Cannabis sativa* in *S. cerevisiae*. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues.

Figure 7:
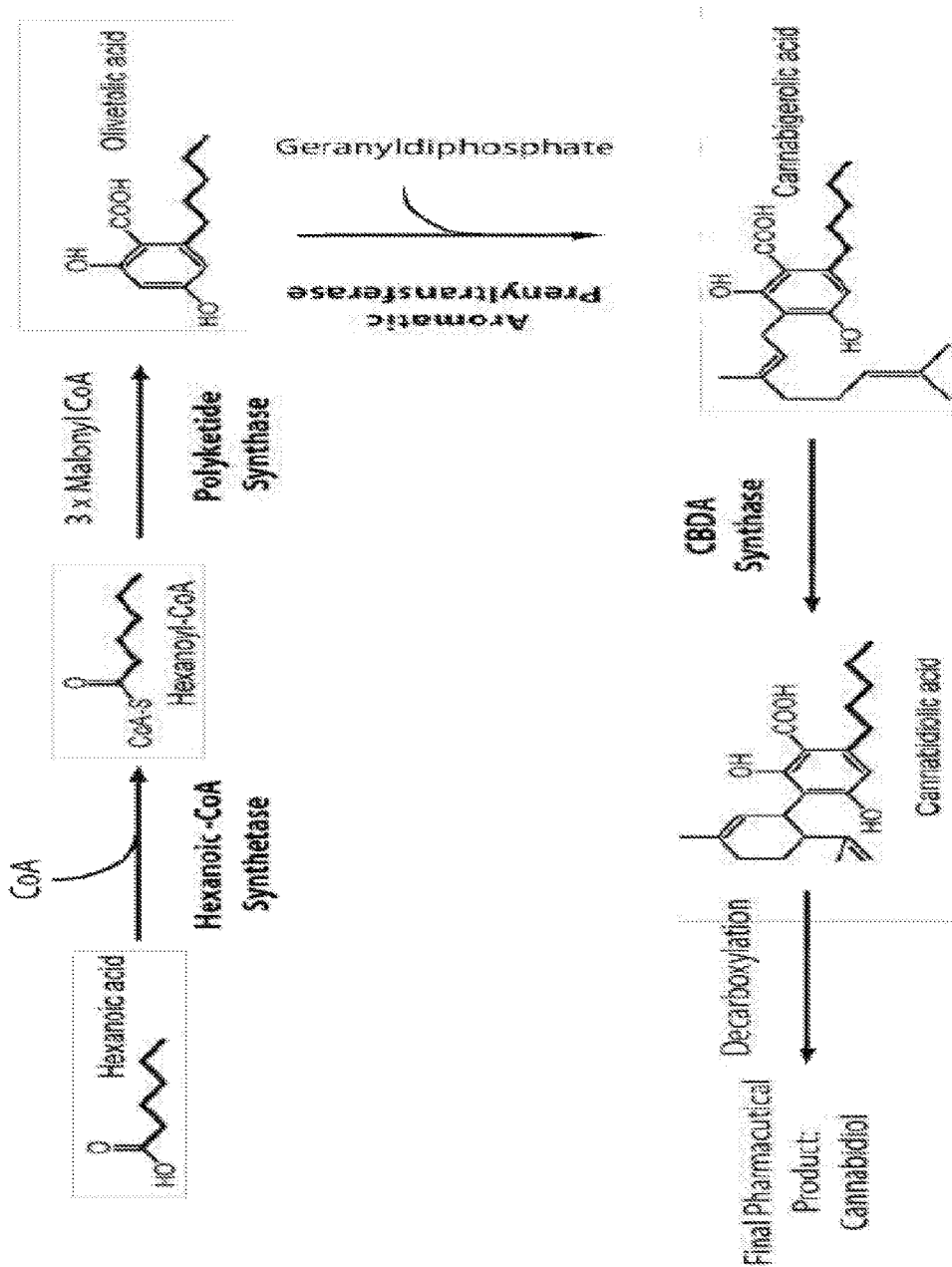
FIG. 7 shows an exemplary metabolic pathway for the production of cannabinoids by *Cannabis sativa*.

FIG. 7 shows an exemplary metabolic pathway for the production of cannabinoids by *Cannabis sativa*.

The biosynthetic route for the production of cannabidiolic acid in *Cannabis sativa* is shown in FIG. 7. The pathway begins with the conversion of Hexanoic acid (a simple fatty acid) to Hexanoyl-CoA by Hexanoyl-CoA Synthetase. Hexanoyl-CoA is converted to Oleviolic acid (OA), a polyketide, by a Polyketide synthase. OA is then prenylated with the monoterpene geranyl diphosphate to cannabigerolic acid by an Aromatic prenyltransferase. Finally, cannabidiolic acid (CBDA) is produced by cyclizing cannabigerolic acid via CBDA synthase (CBDAs). In summary, it takes four enzymatic steps to produce CBDA from Hexanoic acid. The inventors have engineered this metabolic pathway into *S. cerevisiae* (a species of yeast) for the production of CBDA.

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, through genetic engineering many of the required enzymes can be added and the production of GPP can be increased. In order to add the required enzymes for CBDA production in yeast the inventors created plasmids that contain the essential genes in the CBDA biosynthetic pathway. The inventors have transformed these genes into *S. cerevisiae*.

Synthesis of Fusion Genes Required for CBDA Production in *S. cerevisiae*

The genome of *Cannabis sativa* has been investigated and the acyl-activating enzymes CsAAE1 was determined to convert hexanoic acid to hexanoyl-CoA (Step 1 in FIG. 7). The inventors have overexpressed CsAAE1 in yeast while simultaneously supplementing the growth media with Hexanoic acid. By supplementing the media with hexanoic acid, the inventors ensured that the yeast have the required starting materials for the production of hexanoyl-CoA.

The next enzymatic step that was engineered into the yeast strain was for the production of Olivetolic acid (OA) from hexanoyl-CoA. This step requires the substrates hexanoyl-CoA and 3 malonyl-CoA molecules, with the malonyl-CoA molecule produced by yeast naturally. Olivetolic acid production requires two enzymes for the condensation and subsequent cyclization of malonyl-CoA with hexanoyl-CoA. This process requires the tetraketide synthase, olivetolic synthase (OS), and the polyketide cyclase, olivetolic acid cyclase (OAC). In some embodiments, stoichiometric amounts of both of these enzymes are preferred; as it has been experimentally determined that OAC binds a chemical intermediate made by OS. In various embodiments, in order to ensure the proper amounts of OS and OAC the inventors have created a single gene that is a fusion of OS, a self cleaving T2A peptide, and the OAC gene (OS-T2A-OAC) and in certain cases an HA tag was inserted at the C-terminus of OAC to verify protein expression. This entire fusion protein was produced in yeast and the self cleaving peptide is spliced in vivo to produce OS and OAC.

The next enzymatic step requires the production of geranyl pyrophosphate (GPP). In yeast the prenyltransferace Erg20 condenses isopentenyl diphosphate (IPP) and dimethylallyl diphosphate (DMAP) to geranyl pyrophosphate (GPP) and feranyl pyrophosphate (FPP) naturally. While only these two products are produced in yeast, a greater quantity of FPP when compared to GPP is produced. More GPP is required for the production of CBDA. In order to increase the production of GPP compared to FPP the inventors inserted a mutant prenyltransferase, Erg20(K179E) in the yeast strain. This mutant has been shown to shift the ratio of GPP:FPP to 70:30. This Erg20(K179E) mutant was placed on a fusion gene with CsAAE1, the enzyme for hexanoyl-CoA, and a self-cleaving peptide, T2A (CsAAE1-T2A-Erg20(K179E)). We also added a FLAG tag to the C-terminus of the Erg20p (K197E) enzyme (CsAAE1-T2A-Erg20(K179E)-FLAG) to verify expression of this fusion protein in yeast in certain yeast strains. After production in yeast the self-cleaving peptide was cut producing CsAAE1 and Erg20(K179E).

Once the inventors verified that they had enough GPP to prenylate Olivetolic acid to cannabigerolic acid the inventors inserted the aromatic prenyltransferase (CsPt1) gene into the yeast. In this final enzymatic step the inventors placed the cannabidiolic acid synthase (CBDAs) gene into yeast for the conversion of cannabigerolic acid to CBDA. Similar to the inventors' previous approach, they introduced a single gene containing CsPt1, a self-cleaving peptide T2A, CBDs, and in certain cases a MYC tag was inserted at the C-terminus of CBDs in order to verify production of each enzyme (CsPt1-T2A-CBDs-MYC).

Creation of a Stable Yeast Strain Producing the Metabolic Pathway for CBDA

Three stable transformations of *S. cerevesaie* where created utilizing selection for leucine, uracil and tryptophan. The inventors first transformed an auxotrophic yeast strain (his3D1/leu2/trp1-289/ura3-52) with the CsAAE1-T2A-Erg20(K197E)-FLAG gene in an integrating vector. 5 µg of CsAAE1-T2A-Erg20(K197E)-FLAG in a vector containing a gene for tryptophan depletion resistance was linearized with the restriction enzyme EcoRV, transformed into chemically competent InVSc1, and grown on Yeast Nitrogen Base without amino acids and 0.5% ammonium sulfate (YNBA) agar plates supplemented with histidine, leucine, tryptophan, 1% glucose and 2% lactic acid are grown at 30° C. until colonies are formed. Any yeast colonies that did not incorporate the plasmid, that contains the CsAAE1-T2A-Erg20 (K197E)-FLAG gene died since the starting yeast strain is a tryptophan auxotroph. All colonies, with successful plasmid incorporation, where picked and grown in YNBA supplemented with histidine, leucine and uracil, 1% glucose and 2% lactic acid. All colonies were screened for protein production by taking whole cell extracts of each induced clone and the total protein was subjected to SDS-PAGE followed by western blotting against the c-terminal tag of Erg20(K197E). Positive clones where stored at −80° C. in glycerol stocks. The highest expressing clone was taken for the second transformation and was be designated as VscGPHA.

Using the VscGPHA strains the inventors added 5 µg of OS-T2A-OAC-HA in the a vector containing a gene for leucine depletion resistance. This plasmid was linearized with the restriction enzyme AseI and transformed into chemically competent VscGPHA and grown on YNBA agar plates supplemented with histidine and uracil, 1% glucose and 2% lactic acid and grown at 30° C. until colonies were formed. Any yeast colonies that did not incorporate the plasmid that contains the OS-T2A-OAC-HA gene died since the VscGPHA is a leucine auxotroph. All colonies, with successful plasmid incorporation, were picked and grown in YNBA supplemented with histidine, and leucine. All colonies were screened for protein production by taking whole cell extracts of each induced clone and subjected the total protein to SDS-PAGE followed by western blotting against the c-terminal HA tag of OAC. Positive clones were stored at −80° C. in glycerol stocks. The highest expressing clone was taken for the second stable transformation and was designated VscGPHOA.

The final stable transformation was done in a similar way as the previous transformation. The CsPT-T2A-CBDAs-MYC gene was placed in the vector containing a gene for uracil depletion resistance 5 µg of this plasmid was linearized with EcorV and transformed into chemically competent VscGPHOA. Transformed VscGPHOA was grown in YNBA supplemented with histidine, 1% glucose and 2% lactic acid. Any yeast colonies that did not incorporate the plasmid that contains the CsPT-T2A-CBDAs-MYC gene died since they lacked leucine. All colonies were picked and grown in YNBA supplemented with histidine, 1% glucose and 2% lactic acid. All colonies were screened for protein production by taking whole cell extracts of each induced clone and subjecting the total protein to SDS-PAGE followed by western blotting against the c-terminal Myc tag of CBDAs. Positive clones are stored at −80° C. in glycerol stocks. The highest expressing CBDAs was taken for the final strain and designated VscCBDA.

Production of CBDA in Yeast

To initiate the reconstituted metabolic pathway of CBDA a colony of VscCBDA was freshly streaked on a plate of a frozen glycerol stock of VscCBDA. A small culture of VscCBDA was grown in YNBA supplemented with 0.05% histidine, 1% glucose, 2% lactic acid, and 0.03% hexanoic acid overnight at 30° C. The overnight culture was transferred to 1 L of YNBA supplemented with 0.05% histidine, 1% glucose, 2% lactic acid, and 0.03% hexanoic acid and was grown at 30° C. until mid log phase. Cells were pelleted by centrifugation then washed with 200 ml of phosphate buffered saline (PBS) and repelleted. Pelleted cells were resuspended with 1 L of YNBA supplemented with 0.05% histidine, 2% galactose, and 0.03% hexanoic acid and grown at 30° C. overnight.

Overnight 1 L cultures were pelleted by centrifugation, resuspended, washed one time in PBS and pelleted. Cell pellets were resuspended in 40% (wt/vol) KOH and 50% (vol/vol) ethanol solution and boiled for 10 minutes. Metabolite extraction was done by extracting from the boiled extracts 3 times with hexane, then 3 times with ethyl acetate. The spent supernatant broth was extracted in a similar fashion as described above. Organic phases of extracts of each sample were pooled then dried by a rotary evaporator and stored for liquid chromatography mass spectrometry (LC-MS) and gas chromatography mass spectrometry (GC-MS) analysis to confirm and quantitate how much CBDA is produced from strain VscCBDA.

Biosynthetic Production of Cannabidiolic Acid (CBDA) in *K. marxianus*

Through genetic engineering the inventors have reconstituted the cannabidiolic acid (CBDA) metabolic pathway found in *Cannabis sativa* into *K. marxianus* (a species of yeast). Producing CBGA is an initial step in producing many cannabinoids from *Cannabis sativa* in *K. marxianus*. Once CBGA is produced a single additional enzymatic step is required to turn CBGA into many other cannabinoids (CBDA, THCA, CBCA, etc.). The acidic forms of the cannabinoids can be used as a pharmaceutical product or the acidic cannabinoids can be turned into their neutral form for use, for example Cannabidiol (CBD) is produced from CBDA through decarboxylation. The resulting cannabinoid products will be used in the pharmaceutical/nutraceutical industry to treat a wide range of health issues. Synthesis of fusion genes required for CBDA production in *k. Marxianus*

Figure 8:
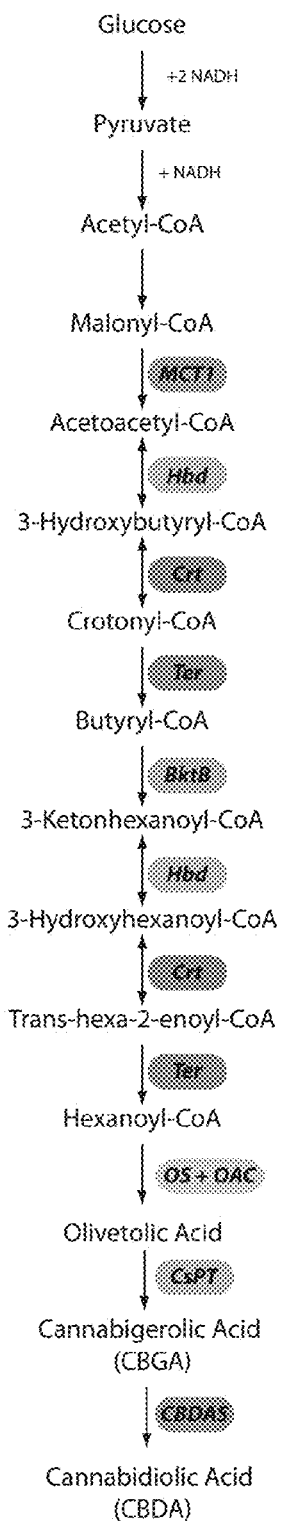
FIG. 8 shows an exemplary biosynthetic route for the production of CBDA from glucose.

FIG. 8 shows an exemplary biosynthetic route for the production of CBDA from glucose.

The biosynthetic route for the production of cannabidiolic acid in *Cannabis sativa*, from glucose to CBDA is shown in FIG. 8. The pathway begins with the conversion of glucose to malonyl-CoA through a series of steps that are common to many strains of yeast. The conversion of malonyl-CoA to Acetoacetyl-CoA is conducted by the enzyme MCT1, an acyl-carrier-protein. Acetoacetyl-CoA is converted to 3-Hydroxybutyryl-CoA by the enzyme 3-hydroxybutyryl-CoA dehydrogenase (Hbd) from *Clostridium acetobutylicum*. Next, 3-Hydroxybutyryl-CoA is converted into Crotonyl-CoA by the enzyme crotonase (Crt) from *Clostridium acetobutylicum* and the conversion of Crotonyl-CoA to Butyryl-CoA is controlled by the enzyme trans-enoyl-CoA reducatase (Ter) from *Treponema denticola*. The Butyryl-CoA is converted to 3-Ketonhexanoyl-CoA by the enzyme β-ketothiolase (Bktb) from *Ralstonia Eutropha*. 3-Ketonhexanoyl-CoA is converted to 3-Hydroxyhexanoyl-CoA by the enzyme Hbd. Hydroxyhexanoyl-CoA is converted to Trans-hexa-2-enoyl-CoA by the enzyme Crt. Trans-hexa-2-enoyl-CoA is converted to Hexanoyl-CoA by the enzyme Ter. Hexanoyl-CoA, with 3 malonyl-CoAs, is converted to Oleviolic acid (OA) by a Polyketide synthase and cyclase, OA and OAC respectively. OA is then prenylated with the monoterpene geranyl diphosphate to cannabigerolic acid by an Aromatic prenyltransferase, CsPT. Finally, cannabidiolic acid (CBDA) is produced by cyclizing cannabigerolic acid via CBDA synthase (CBDAS). We have engineered this metabolic pathway into *K. marxianus* (a species of yeast) for the production of CBDA (FIG. 8).

There are a few key differences between plant polyketide and terpene biosynthesis when compared to yeast. Yeast does not contain many of the enzymes and fatty acids required for the production of CBDA. Moreover, yeast do not express high levels of geranyl diphosphate (GPP), a chemical required for the production of cannabigerolic acid, the precursor to CBDA. Yet, the inventors through genetic engineering created many of the required enzymes that can be added so the production of GPP was increased. In order to add the required enzymes for CBDA production in yeast the inventors created plasmids that contain the essential genes in the CBDA biosynthetic pathway. The inventors have transformed these genes into *K. marxianus*.

Creation of a Stable *K. marxianus* Strain Producing the Metabolic Pathways for Hexonyl-coA and CBDA Two stable transformations of *K. marxianus* were created utilizing selection for uracil and G418 (Genenticin). The inventors first transformed an auxotrophic *K. marxianus* strain (ATCC 17555 KM5) with 5 different genes needed to produce high levels of hexanoyl-CoA. After functional conformation of the genes required for hexanoyl-CoA the inventors did a second transformation with the genes responsible for CBDA production. The molecular biology methods required for biosynthetic production of CBDA in *K. marxianus* are outlined below.

Gene names Crt, Bktb, MCT1, TeR, Hbd, Erg20p(K179E) were codon optimized, synthesized and subcloned into puc57 and p426 ATCC with the restriction enzymes SpeI and SalI.

Genes Crt, Bktb, MCT1, TeR, Hbd, and Erg20p(K179E) were amplified via PCR using the primers GPD_F and URA_R and all 6 amplicons were electroporated into *K. marxianus* ATCC 17555 KM5 at a concentration of 200 nM and selected onto yeast nitrogen base (YNB) supplemented with amino acid dropout mix (DO supplement—Ura Clonetech 630416) 2% glucose, and 2% Agar plates.

Gene integration and functional gene expression of Crt, Bktb, MCT1, TeR, Hbd, and Erg20p(K179E) was validated by genomic PCR and RT-PCR methods respectively. The final strain produced containing the functional expression of Crt, Bktb, MCT1, TeR, Hbd, and Erg20p(K179E) was labeled kMarxHex1.

Gene names CBDAs, CsPt, OS, and OAC were codon optimized and synthesized by Genscript. The codon optimized gene sequences of CBDAs and CsPt were cloned in frame with a nucleotide sequence containing a self cleaving T2A peptide and designated as CstTCbds. The codon optimized gene sequences of OS and OAC were cloned in frame with a nucleotide sequence containing a self cleaving T2A peptide and designated as OSTOc. CsTCbds and OSTOc were cloned in frame with an *S. cerevisiae* internal ribosomal entry site (IRES), Ure2, into a galactose inducible vector and the final gene sequence pcen/arsGal-OSTOc-IRES-CsTCbds plasmid can be seen below. The plasmid pcen/arsGal-OSTOc-IRES-CsTCbds was used to synthesize a functional gene fragment that expresses the enzymes CBDAs, CsPt, OS, and OAC by using the primers GalI-RES_F, GalIRES_R.

The Gibson Assembly method was used to subclone the PCR fragment from [0057] into the plasmid HO-poly-KanMx4-HO (ATCC 87804) using the primers KmX-IRES_F and KmXIRES_R to create the plasmid pHOOSC-stKnMxHO.

The plasmid pHOOSCstKnMxHO was digested with NotI and transformed into kMarxHex1 using standard electroporation methods. The selection of stable integrants was done with yeast nitrogen base (YNB) supplemented with amino acid dropout mix (DO supplement—Ura Clonetech 630416) 2% glucose, 1 mg/ml G418 (Gibco) and 2% Agar plates.

Gene integration and functional gene expression of pHOOSCstKnMxHO validated by genomic PCR and RT-PCR methods respectively. The final strain produced containing the functional expression of Crt, Bktb, MCT1, TeR, Hbd, Erg20p(K179E) CBDAs, CsPt, OS, and OAC was labeled k.MarxCBDA.

Production of CBDA in *K. marxianus*

To initiate the reconstituted metabolic pathway of CBDA, a colony from *K. marx* CBDA was freshly streaked onto an agar plate from a frozen glycerol stock of k.MarxCBDA. A small culture of VscCBDA was grown in YNBA base (YNB) supplemented with amino acid dropout mix (DO supplement—Ura Clonetech 630416) 2% glucose, 1 mg/ml G418 (Gibco) and 2% Agar plates was grown overnight at 30° C. The overnight culture was transferred to 1 L of YNBA supplemented with base (YNB) supplemented with amino acid dropout mix (DO supplement—Ura Clonetech 630416) 2% glucose, and 1 mg/ml G418 (Gibco) and was grown at 30° C. until mid log phase. Cells were pelleted by centrifugation then washed with 200 ml of phosphate buffered saline (PBS) and repelleted. Pelleted cells were resuspended with 1 L of YNBA supplemented with base (YNB) supplemented with amino acid dropout mix (DO supplement—Ura Clonetech 630416) 2% galactose, and 1 mg/ml G418 (Gibco) and grown at 30° C. overnight.

Processing CBDA for Analysis of Cannabinoid Production

Overnight 1 L cultures were pelleted by centrifugation, re-suspended, washed one time in PBS and pelleted. The process for extracting cannabinoids from the yeast generally follows the following basic steps:

1. Remove the yeast cells from the media by centrifugation or filtration.
2. Lysis the cells using either chemical or mechanical methods or a combination of methods. Mechanical methods can include a French Press or glass bead milling or other standard methods. Chemical methods can include enzymatic cell lysis, solvent cell lysis, or detergent based cell lysis.
3. Perform a liquid-liquid extraction of the cannabinoids form the cell lysate using the appropriate chemical solvent. An appropriate solvent is any solvent where the cannabinoids are highly soluble in this solvent and the solvent is not miscible in water. Examples of this are hexane, ethyl acetate, and cyclohexane. Preferred solvents can be straight or branched alkane chains (C5-C8) work well; mixtures of these solvents can also be use.

Protocol Used for Cannabinoid Extraction from Yeast Cell Lysate

1. After lysising the cells using any mechanical technique, add 1 mL of 4M KCl, pH2.0 to each 1 mL of cell lysate.
2. Add 1-2 mLs of ethyl acetate for each 1 mL of cell lysate.
3. Rigorously mix for 1 min.

4. Centrifuge the mixture for 5 min at 1000×g.
5. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for Cannabinoid Extraction from Growth Media (for Secreted Cannabinoid Samples)
1. Add 1 mL of ethyl acetate for every 1 mL of growth media.
2. Rigorously mix for 1 min.
3. Centrifuge the mixture for 5 min at 1000×g.
4. Remove the top ethyl acetate layer. Cannabinoids are present in this layer.
   a. The ethyl acetate can be removed under vacuum if desired.
   b. Cannabinoids can be further purified through liquid chromatography methods if desired.

Protocol Used for GC-MS Analysis of Cannabinoid Extracts for *k. Marx* CBDA
1. Remove solvent from samples under vacuum.
2. Re-suspend dry samples in either 100 uL of dry hexane or dry ethyl acetate 3. Add 20 uL of N-Methyl-N-(trimethylsilyl) trifluoroacetamide (MSTFA)
4. Briefly mix
5. Heat solution to 60° C. for 10-15 minutes
6. GC-MS Method
   a. Instrument Agilent 6890-5975 GC-MS (Model Number: Agilent 19091S-433)
   b. Column HP-5MS 5% Phenyl Methyl Siloxane
   c. OVEN:
      i. Initial temp: 100° C. (On) Maximum temp: 300° C.
      ii. Initial time: 3.00 min Equilibration time: 0.50 min
      iii. Ramps:

| # | Rate | Final temp | Final time |
|---|------|-----------|------------|
| 1 - | 30.00 | 280 | 1.00 |
| 2 - | 70.00 | 300 | 5.00 |
| 3 - | 0.0 (Off) | | | iv. Post temp: 0° C.
      v. Post time: 0.00 min
      vi. Run time: 15.29 min

What is claimed is:

1. A method for making cannabidiolic acid, the method comprising:

transforming *S. cervisiae* with a first nucleotide sequence comprising the nucleotide sequence of SEQ. ID. NO.1 expressing an acyl-activating enzyme;

transforming the *S. cervisiae* with a second nucleotide sequence comprising the nucleotide sequence of SEQ. ID. NO.22 expressing a mutant prenyltransferase;

transforming the *S. cervisiae* with a third nucleotide sequence comprising the nucleotide sequence of SEQ. ID. NO.25 expressing olivetolic synthase;

transforming the *S. cervisiae* with a fourth nucleotide sequence comprising the nucleotide sequence of SEQ. ID. NO.26 expressing olivetolic acid cyclase;

transforming the *S. cervisiae* with a fifth nucleotide sequence comprising the nucleotide sequence of SEQ. ID. NO.27 expressing aromatic prenyltransferase; and transforming the *S. cervisiae* with a sixth nucleotide sequence comprising the nucleotide sequence of SEQ. ID. NO.28 expressing cannabidiolic acid synthase.

* * * * *

UNITED STATES PATENT AND TRADEMARK OFFICE
CERTIFICATE OF CORRECTION

| | | |
|---|---|---|
| PATENT NO. | : 10,093,949 B2 | |
| APPLICATION NO. | : 15/815651 | |
| DATED | : October 9, 2018 | |
| INVENTOR(S) | : Jason L. Poulos and Anthony N. Farina | |

It is certified that error appears in the above-identified patent and that said Letters Patent is hereby corrected as shown below:

On the Title Page

Item (72) To correct inventor's name from "Anthony N. Farnia" to "Anthony N. Farina".

Signed and Sealed this
Twenty-eighth Day of March, 2023

Katherine Kelly Vidal
*Director of the United States Patent and Trademark Office*

SEQUENCE LISTING

<160> NUMBER OF SEQ ID NOS: 53

<210> SEQ ID NO 1
<211> LENGTH: 7969
<212> TYPE: DNA
<213> ORGANISM: Artificial Sequence
<220> FEATURE:
<223> OTHER INFORMATION: Codon optimized

<400> SEQUENCE: 1

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tcttttttcta    300 ttactcttgg cctcctctag tacactctat atttttttat gcctcggtaa tgattttcat     360 ttttttttt cccctagcgg atgactcttt ttttttctta gcgattggca ttatcacata      420
atgaattata cattatataa agtaatgtga tttcttcgaa gaatatacta aaaaatgagc     480
aggcaagata aacgaaggca aagatgacag agcagaaagc cctagtaaag cgtattacaa     540
atgaaaccaa gattcagatt gcgatctctt taaagggtgg tcccctagcg atagagcact     600
cgatcttccc agaaaaagag gcagaagcag tagcagaaca ggccacacaa tcgcaagtga     660
ttaacgtcca cacaggtata gggtttctgg accatatgat acatgctctg gccaagcatt     720
ccggctggtc gctaatcgtt gagtgcattg gtgacttaca catagacgac catcacacca     780
ctgaagactg cgggattgct ctcggtcaag cttttaaaga ggccctactg gcgcgtggag     840
taaaaaggtt tggatcagga tttgcgcctt tggatgaggc actttccaga gcggtggtag     900
atctttcgaa caggccgtac gcagttgtcg aacttggttt gcaaagggag aaagtaggag     960
atctctcttg cgagatgatc ccgcattttc ttgaaagctt tgcagaggct agcagaatta    1020
ccctccacgt tgattgtctg cgaggcaaga atgatcatca ccgtagtgag agtgcgttca    1080
aggctcttgc ggttgccata agagaagcca cctgcccaa tggtaccaac gatgttccct    1140
```

```
ccaccaaagg tgttcttatg tagtgacacc gattatttaa agctgcagca tacgatatat    1200
atacatgtgt atatatgtat acctatgaat gtcagtaagt atgtatacga acagtatgat    1260
actgaagatg acaaggtaat gcatcattct atacgtgtca ttctgaacga ggcgcgcttt    1320 cctttttttct ttttgctttt tctttttttt tctcttgaac tcgacggatc tatgcggtgt   1380
gaaataccgc acagatgcgt aaggagaaaa taccgcatca ggaaattgta acgttaata    1440 ttttgttaaa attcgcgtta aattttgttt aaatcagctc attttttaac caataggccg    1500
aaatcggcaa aatcccttat aaatcaaaag aatagaccga gatagggttg agtgttgttc    1560
cagtttggaa caagagtcca ctattaaaga acgtggactc caacgtcaaa gggcgaaaaa    1620
ccgtctatca gggcgatggc ccactacgtg aaccatcacc ctaatcaagt ttttgtgggt    1680
cgaggtgccg taaagcacta atcggaacc ctaaagggag ccccgatttt agagcttgac     1740
ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
gatcggtgcg ggcctcttcg ctattacgcc agctggcgaa aggggggatgt gctgcaaggc   1980 gattaagttg ggtaacgcca gggttttccc agtcacgacg ttgtaaaacg acggccagtg    2040
agcgcgcgta atacgactca ctatagggcg aattgggtac cggccgcaaa ttaaagcctt    2100
cgagcgtccc aaaaccttct caagcaaggt tttcagtata atgttacatg cgtacacgcg    2160
tctgtacaga aaaaaagaa aaatttgaaa tataaataac gttcttaata ctaacataac     2220 tataaaaaa taaataggga cctagacttc aggttgtcta actccttcct tttcggttag     2280
agcggatgtg gggggagggc gtgaatgtaa gcgtgacata actaattaca tgactcgagg    2340
tcgactcatt cgaaatgact gaattgttgt ctcaaaactc ttctcatgat cttgtttgtt    2400
gcagttctag gtaaggatga caatgggaca actctagtaa cttttgaataa tgggttcaat   2460 ttcttttgca aacccaagtt aaaggataat ctcaattggt tcaaatcaat ggttgtgtcg    2520
tttgaatcct tcaatacgaa aaatatgacc aattgttctg gaccaccacc caaaggtgga    2580
acaccaatag cagtggttc aaaaactctg tcatctactt cattacagac tctttcgatt     2640
tcgatagaac taattttgat accaccgatg ttcatagtgt catcggctct accgtgtgca    2700
tggtagtaac cgttagaggt caattcgaaa atgtcaccat gtcttctcaa tacttcacca    2760
ttcaaggttg gcatacccctt gaaatagaca tcgtgatgat taccgtttaa caatgttttt   2820
gaggcaccaa acataacagg acctaatgcc aattcaccga tacctggctt attttaggc    2880 attgggtaac cgttcttatc taatatgtac aaggtgcaac ccatacattg ggatgaaaaa    2940
gaacttaaag attgagcttg caaaaatgaa ccagcagaaa aagcaccacc gatttctgta    3000
ccaccacaca tttctataac tggcttgtag ttagctctac ccattaacca caaatattcg    3060
tctacattag aggcttcacc ggatgaagaa agcatcctta tggtggacca atcgtaacct    3120
gaaacacaat ttgtggattt ccatgatctt acaatagatg gtacgacacc caacattgtg    3180
acctttgcat cttgaacaaa tttagcgaaa ccagagacta aaggactacc gttgtacaag    3240
gcaatagatg caccatttaa caaactagca taaaccaacc aaggaccat catccaaccc     3300 aaattagttg gccatactat aacgtcacct tttctaatat ccaaatgaga ccaaccatca    3360
gcagcagcct tcaatggggt ggcttgtgtc caaggaattg cttttggttc acctgtagta    3420
ccactggaga ataagatgtt agtataagca tcaacaggtt gttctctggc agtaaactcg    3480
```

-continued

```
cagttttta actccttggc tctttctaaa aagtaatccc aagatatgtc accatctctc    3540
aattctgcac caatgttaga accactacaa gggataacta ttgccattgg ggatttagct    3600
tcaactactc ttgaatacaa tggtattctc tttttacctc tgatgatgtg atcttgtgtg    3660
aaaattgcct tagctttgga taatctcaat ctagttgaga tttcaggggc ggaaaatgaa    3720
tctgctatag agacaactac gtaaccagcc aatactatgg ccaaatatat aacaacagca    3780
tcaacatgca ttggcatatc gatggctatt gcacaacctt tttctaaacc catttcttcc    3840
aatgcataac caaccaacca aactctcttt ctcaattgat ctaatgtcaa cttattcaaa    3900
ggcaagtcat cgttaccctc gtctctccaa acgatcatag tatcgttcaa tttcttattg    3960
gagtttacgt tcaagcaatt tttagctgag ttcaagtaac caccaggtaa ccattcagaa    4020
ccacctgggt tgttgatgtc atctcttctc aagatacatt ctgggtcctt agagaaacta    4080
attttcattt catccatcaa tactgttctc aatagactt cagggtttct aacagaaaat    4140
tcttggaagt gagaaaaaga agaaattgga tctttgtact ttacacccaa aaattcttta    4200
cctctctttt ccaacaaagc acccaaatta gttgacttga cttttcagg gtctggaatc    4260
caagcaggtg gggctggacc gaaatccttg tagcaaccat aaaacaacat ttggtgtaag    4320
gagaaaggca aatctggtga caagatatgg ttagcgatgt tgatccaagt ttgaggggtt    4380
gcagcaccat aattacaaac gatttctgcc aatctaccat gtaatgtttc tgctacttct    4440
gaggtgatac ccaatgcgat gaaatctgag gcaacgactg aatccaagga cttatagttt    4500
ttacccatac tagttctaga tccgtcgaaa ctaagttctt ggtgttttaa aactaaaaaa    4560
aagactaact ataaaagtag aatttaagaa gtttaagaaa tagatttaca gaattacaat    4620
caatacctac cgtctcttata tacttattag tcaagtaggg gaataatttc agggaactgg    4680
tttaaacctt ttttttcagc ttttttccaaa tcagagagag cagaaggtaa tagaaggtgt    4740
aagaaaatga gatagataca tgcgtgggtc aattgccttg tgtcatcatt tactccaggc    4800
aggttgcatc actccattga ggttgtgccc gttttttgcc tgtttgtgcc ctgttctctg    4860
tagttgcgct aagagaatgg acctatgaac tgatggttgg tgaagaaaac aatattttgg    4920
tgctgggatt cttttttttt ctggatgcca gcttaaaaag cgggctccat tatatttagt    4980
ggatgccagg aataaacctg ttcacccaag caccatcagt gttatatatt ctgtgtaacc    5040
cgccccctat tttggcatgt acgggttaca gcagaattaa aaggctaatt ttttgactaa    5100
ataaagttag gaaaatcact actattaatt atttacgtat tctttgaaat ggcagtattg    5160
ataatgataa actcgagagc tccagctttt gttcccttta gtgagggtta attgcgcgct    5220
tggcgtaatc atggtcatag ctgtttcctg tgtgaaattg ttatccgctc acaattccac    5280
acaacatagg agccggaagc ataaagtgta aagcctgggg tgcctaatga gtgaggtaac    5340
tcacattaat tgcgttgcgc tcactgcccg ctttccagtc gggaaacctg tcgtgccagc    5400
tgcattaatg aatcggccaa cgcgcgggga gaggcggttt gcgtattggg cgctcttccg    5460
cttcctcgct cactgactcg ctgcgctcgg tcgttcggct gcggcgagcg gtatcagctc    5520
actcaaaggc ggtaatacgg ttatccacag aatcagggga taacgcagga agaacatgt    5580
gagcaaaagg ccagcaaaag gccaggaacc gtaaaaaggc cgcgttgctg gcgtttttcc    5640
ataggctccg ccccctgac gagcatcaca aaaatcgacg ctcaagtcag aggtggcgaa    5700
acccgacagg actataaaga taccaggcgt ttccccctgg aagctccctc gtgcgctctc    5760
ctgttccgac cctgccgctt accggatacc tgtccgcctt tctcccttcg ggaagcgtgg    5820
cgctttctca tagctcacgc tgtaggtatc tcagttcggt gtaggtcgtt cgctccaagc    5880
```

```
tgggctgtgt gcacgaaccc cccgttcagc ccgaccgctg cgccttatcc ggtaactatc      5940
gtcttgagtc aacccggta agacacgact tatcgccact ggcagcagcc actggtaaca       6000
ggattagcag agcgaggtat gtaggcggtg ctacagagtt cttgaagtgg tggcctaact      6060
acggctacac tagaaggaca gtatttggta tctgcgctct gctgaagcca gttaccttcg     6120
gaaaaagagt tggtagctct tgatccggca acaaaccac cgctggtagc ggtggttttt     6180
ttgtttgcaa gcagcagatt acgcgcagaa aaaaggatc tcaagaagat cctttgatct      6240
tttctacggg gtctgacgct cagtggaacg aaaactcacg ttaagggatt ttggtcatga     6300
gattatcaaa aaggatcttc acctagatcc ttttaaatta aaaatgaagt tttaaatcaa     6360
tctaaagtat atatgagtaa acttggtctg acagttacca atgcttaatc agtgaggcac    6420
ctatctcagc gatctgtcta tttcgttcat ccatagttgc ctgactcccc gtcgtgtaga     6480
taactacgat acgggagggc ttaccatctg gccccagtgc tgcaatgata ccgcgagacc    6540
cacgctcacc ggctccagat ttatcagcaa taaaccagcc agccggaagg gccgagcgca    6600
gaagtggtcc tgcaacttta tccgcctcca tccagtctat taattgttgc cgggaagcta    6660
gagtaagtag ttcgccagtt aatagtttgc gcaacgttgt tgccattgct acaggcatcg    6720
tggtgtcacg ctcgtcgttt ggtatggctt cattcagctc cggttcccaa cgatcaaggc    6780
gagttacatg atcccccatg ttgtgcaaaa aagcggttag ctccttcggt cctccgatcg    6840
ttgtcagaag taagttggcc gcagtgttat cactcatggt tatggcagca ctgcataatt    6900
ctcttactgt catgccatcc gtaagatgct tttctgtgac tggtgagtac tcaaccaagt    6960
cattctgaga atagtgtatg cggcgaccga gttgctcttg cccggcgtca atacgggata    7020
ataccgcgcc acatagcaga actttaaaag tgctcatcat tggaaaacgt tcttcggggc    7080
gaaaactctc aaggatctta ccgctgttga gatccagttc gatgtaaccc actcgtgcac    7140
ccaactgatc ttcagcatct tttactttca ccagcgtttc tgggtgagca aaaacaggaa    7200
ggcaaaatgc cgcaaaaaag gaataagggc gacacggaaa tgttgaatac tcatactct    7260 tcctttttca atattattga gcatttatc agggttattg tctcatgagc ggatacatat     7320
ttgaatgtat ttagaaaaat aaacaaatag gggttccgcg cacatttccc cgaaaagtgc    7380
cacctgggtc cttttcatca cgtgctataa aaataattat aatttaaatt ttttaatata    7440
aatatataaa ttaaaatag aaagtaaaaa agaaattaa agaaaaata gttttttgttt      7500 tccgaagatg taaaagactc tagggggatc gccaacaaat actacctttt atcttgctct    7560
tcctgctctc aggtattaat gccgaattgt ttcatcttgt ctgtgtagaa gaccacacac    7620
gaaaatcctg tgattttaca ttttacttat cgttaatcga atgtatatct atttaatctg    7680
cttttcttgt ctaataaata tatatgtaaa gtacgctttt tgttgaaatt ttttaaacct    7740
ttgtttattt tttttcttc attccgtaac tcttctacct tctttatta ctttctaaaa     7800 tccaaataca aaacataaaa ataaataaac acagagtaaa ttcccaaatt attccatcat    7860
taaaagatac gaggcgcgtg taagttacag gcaagcgatc cgtcctaaga accattatt    7920 atcatgacat taacctataa aaataggcgt atcacgaggc cctttcgtc              7969
```

<210> SEQ ID NO 2
<211> LENGTH: 10004
<212> TYPE: DNA
<213> ORGANISM: Artificial Sequence
<220> FEATURE:
<223> OTHER INFORMATION: Codon optimized

<400> SEQUENCE: 2

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tcttttcta     300
ttactcttgg cctcctttca attcatcatt ttttttat tctttttt gatttcggtt     360
tctttgaaat ttttttgatt cggtaatctc cgaacagaag gaagaacgaa ggaaggagca     420
cagacttaga ttggtatata tacgcatatg tagtgttgaa gaaacatgaa attgcccagt     480
attcttaacc caactgcaca gaacaaaaac ctgcaggaaa cgaagataaa tcatgtcgaa     540
agctacatat aaggaacgtg ctgctactca tcctagtcct gttgctgcca agctatttaa     600
tatcatgcac gaaaagcaaa caaacttgtg tgcttcattg gatgttcgta ccaccaagga     660
attactggag ttagttgaag cattaggtcc caaaatttgt ttactaaaaa cacatgtgga     720
tatcttgact gatttttcca tggagggcac agttaagccg ctaaaggcat tatccgccaa     780
gtacaatttt ttactcttcg aagacagaaa atttgctgac attggtaata cagtcaaatt     840
gcagtactct gcgggtgtat acagaatagc agaatgggca gacattacga atgcacacgg     900
tgtggtgggc ccaggtattg ttagcggttt gaagcaggcg gcagaagaag taacaaagga     960
acctagaggc cttttgatgt tagcagaatt gtcatgcaag ggctccctat ctactggaga    1020
atatactaag ggtactgttg acattgcgaa gagcgacaaa gattttgtta tcggctttat    1080
tgctcaaaga gacatgggtg gaagagatga aggttacgat tggttgatta tgacacccgg    1140
tgtgggttta gatgacaagg gagacgcatt gggtcaacag tatagaaccg tggatgatgt    1200
ggtctctaca ggatctgaca ttattattgt tggaagagga ctatttgcaa agggaaggga    1260
tgctaaggta gagggtgaac gttacagaaa agcaggctgg gaagcatatt tgagaagatg    1320
cggccagcaa aactaatgac accgattatt taaagctgca gcatacgata tatatacatg    1380
tgtatatatg tataccctatg aatgtcagta agtatgtata cgaacagtat gatactgaag    1440
atgacaaggt aatgcatcat tctatacgtg tcattctgaa cgaggcgcgc tttccttttt    1500
tcttttgct ttttctttt ttttctcttg aactcgacgg atctatgcgg tgtgaaatac    1560
cgcacagatg cgtaaggaga aaataccgca tcaggaaatt gtaaacgtta atattttgtt    1620
aaaattcgcg ttaaattttt gttaaatcag ctcatttttt aaccaatagg ccgaaatcgg    1680
caaaatccct tataaatcaa aagaatagac cgagataggg ttgagtgttg ttccagtttg    1740
gaacaagagt ccactattaa agaacgtgga ctccaacgtc aaagggcgaa aaaccgtcta    1800
tcagggcgat ggcccactac gtgaaccatc accctaatca agttttttgg ggtcgaggtg    1860
ccgtaaagca ctaaatcgga accctaaagg gagcccccga tttagagctt gacggggaaa    1920
gccggcgaac gtggcgagaa aggaagggaa gaaagcgaaa ggagcgggcg ctagggcgct    1980
ggcaagtgta gcggtcacgc tgcgcgtaac caccacaccc gccgcgctta atgcgccgct    2040
acagggcgcg tcgcgccatt cgccattcag gctgcgcaac tgttgggaag ggcgatcggt    2100
gcgggcctct tcgctattac gccagctggc gaaagggggga tgtgctgcaa ggcgattaag    2160
ttgggtaacg ccagggtttt cccagtcacg acgttgtaaa acgacggcca gtgagcgcgc    2220
gtaatacgac tcactatagg gcgaattggg taccggccgc aaattaaagc cttcgagcgt    2280
cccaaaacct tctcaagcaa ggttttcagt ataatgttac atgcgtacac gcgtctgtac    2340
```

```
agaaaaaaaa gaaaaatttg aaatataaat aacgttctta atactaacat aactataaaa    2400
aaataaatag ggacctagac ttcaggttgt ctaactcctt cctttcggt tagagcggat     2460 gtgggggag ggcgtgaatg taagcgtgac ataactaatt acatgactcg aggtcgactt     2520
acttgtcatc gtcatctttg tagtcaatat cgtggtcttt atagtcaccg tcatgatcct    2580
tgtaatcctt tgatctcttg tagaccttat tcaagaaagc tgtcaaaacg tcggctttaa    2640
aacctcttga ttcatcaact tgactaatct ttgcctttaa gtcttagcg atggattctt     2700 cgtattcatg gtacaattgt tcaatcttca aatcattaaa aattttctta cactttgctt    2760
cagcaactga gtccttttta ccgtagtttt catccaaagt ctttctttgt tcggcagatg    2820
ctaattccaa agccttgtta ataacccaac tgcacttatt gtcttgaata tctgtaccga    2880
ttttacctat ttgttctgga gtaccgaaac agtctaagta gtcatcttgg atttggaagt    2940
attcacccaa aggtatcaaa acatctcttg cttgcttcaa gtctttttca tcagtaatac    3000
cagctacgta catagccaag gcgactggca aatagaagga gtaataagca gtttcaaagg    3060
tgacgatgaa tgaatgtttc ttcaaggaaa actttgacaa gtcaacttta tcttcaggtg    3120
cagttatcaa atccatcaat tgacccaatt ctgtttggaa agtaacttcg tggataatt     3180 cggtaatatc gatgtagtac ttttcgtttc tgaaatgtga cttcaacaat ttatagatag    3240
cggcttccaa cataaaagca tcatttatgg ctatttcacc aacttctgga actttgtacc    3300
agcatggttg acctcttctt gttatagact tatccatcat gtcatcggca accaaaaagt    3360
atgcttgcaa caattcaata caccaaccca agatagcgac cttttcgtat tcttcttgac    3420
ctaattgttc aacggttttg ttagacaaga tagcataagt atcaactaca ctcaaacctc    3480
tattcaattt accacctgga gtattgtagt ttaaagagtg agcataccaa tcgcaggctt    3540
ctttaggcat accataagct aacaaactag cgttcaattc ttcaactaac tttgggaata    3600
cgttcaagaa tctttctctt cttatttcct tttctgaagc cataggacct ggattttctt    3660
caacgtcacc acatgttaac aaagaacctc taccttcttc gaaatgactg aattgttgtc    3720
tcaaaactct tctcatgatc ttgtttgttg cagttctagg taaggatgac aatgggacaa    3780
ctctagtaac tttgaataat gggttcaatt tcttttgcaa acccaagtta aaggataatc    3840
tcaattggtt caaatcaatg gttgtgtcgt ttgaatcctt caatacgaaa atatgaccca    3900
attgttctgg accaccaccc aaaggtggaa caccaatagc agtggtttca aaaactctgt    3960
catctacttc attacagact cttcgattt cgatagaact aattttgata ccaccgatgt     4020
tcatagtgtc atcggctcta ccgtgtgcat ggtagtaacc gttagaggtc aattcgaaaa    4080
tgtcaccatg tcttctcaat acttcaccat tcaaggttgg catacccttg aaatagacat    4140
cgtgatgatt accgttaaac aatgttttg aggcaccaaa cataacagga cctaatgcca    4200
attcaccgat acctggctta ttttaggca ttgggtaacc gttcttatct aatatgtaca     4260
aggtgcaacc catacattgg gatgaaaaag aacttaaaga ttgagcttgc aaaaatgaac    4320
cagcagaaaa agcaccaccg atttctgtac caccacacat ttctataact ggcttgtagt    4380
tagctctacc cattaaccac aaatattcgt ctacattaga ggcttcaccg gatgaagaaa    4440
agcatcttat ggtggaccaa tcgtaacctg aaacacaatt tgtggatttc catgatctta    4500
caatagatgg tacgacaccc aacattgtga cctttgcatc ttgaacaaat ttagcgaaac    4560
cagagactaa aggactaccg ttgtacaagg caatagatgc accatttaac aaactagcat    4620
aaaccaacca aggacccatc atccaaccca aattagttgg ccatactata acgtcacctt    4680
```

-continued

```
ttctaatatc caaatgagac caaccatcag cagcagcctt caatggggtg gcttgtgtcc      4740
aaggaattgc ttttggttca cctgtagtac cactggagaa taagatgtta gtataagcat      4800
caacaggttg ttctctggca gtaaactcgc agttttttaaa ctccttggct ctttctaaaa     4860
agtaatccca agatatgtca ccatctctca attctgcacc aatgttagaa ccactacaag      4920
ggataactat tgccattggg gatttagctt caactactct tgaatacaat ggtattctct      4980
ttttacctct gatgatgtga tcttgtgtga aaattgcctt agctttggat aatctcaatc      5040
tagttgagat ttcaggggcg gaaaatgaat ctgctataga gacaactacg taaccagcca      5100
atactatggc caaatatata acaacagcat caacatgcat tggcatatcg atggctattg      5160
cacaaccttt ttctaaaccc atttcttcca atgcataacc aaccaaccaa actctctttc      5220
tcaattgatc taatgtcaac ttattcaaag gcaagtcatc gttaccctcg tctctccaaa      5280
cgatcatagt atcgttcaat ttcttattgg agtttacgtt caagcaattt ttagctgagt      5340
tcaagtaacc accaggtaac cattcagaac cacctgggtt gttgatgtca tctcttctca      5400
agatacattc tgggtcctta gagaaactaa ttttcatttc atccatcaat actgttctcc      5460
aatagacttc agggtttcta acagaaaatt cttggaagtg agaaaaagaa gaaattggat      5520
ctttgtactt tacacccaaa aattctttac ctctcttttc caacaaagca cccaaattag      5580
ttgacttgac tttttcaggg tctggaatcc aagcaggtgg ggctggaccg aaatccttgt      5640
agcaaccata aaacaacatt tggtgtaagg agaaaggcaa atctggtgac aagatatggt      5700
tagcgatgtt gatccaagtt tgaggggttg cagcaccata attacaaacg atttctgcca      5760
atctaccatg taatgtttct gctacttctg aggtgatacc caatgcgatg aaatctgagg      5820
caacgactga atccaaggac ttatagtttt tacccatact agttctagat ccgtcgaaac      5880
taagttcttg gtgttttaaa actaaaaaaa agactaacta taaagtaga  atttaagaag      5940 tttaagaaat agatttacag aattacaatc aataccatcc gtctttatat acttattagt      6000
caagtagggg aataatttca gggaactggt ttaaaccttt ttttttcagct ttttccaaat     6060 cagagagagc agaaggtaat agaaggtgta agaaaatgag atagatacat gcgtgggtca      6120
attgccttgt gtcatcattt actccaggca ggttgcatca ctccattgag ttgtgcccg       6180 tttttttgcct gtttgtgccc tgttctctgt agttgcgcta agagaatgga cctatgaact     6240
gatggttggt gaagaaaaca atattttggt gctgggattc ttttttttttc tggatgccag     6300 cttaaaaagc gggctccatt atatttagtg gatgccagga ataaacctgt tcacccaagc      6360
accatcagtg ttatatattc tgtgtaaccc gccccctatt ttggcatgta cgggttacag      6420
cagaattaaa aggctaattt tttgactaaa taaagttagg aaaatcacta ctattaatta     6480
tttacgtatt ctttgaaatg gcagtattga taatgataaa ctcgagagct ccagcttttg      6540
ttcagttgat tgtatgcttg gtatagcttg aaatattgtg cagaaaaaga aacaaggaag      6600
aaagggaacg agaacaatga cgaggaaaca aaagattaat aattgcaggt ctatttatac      6660
ttgatagcaa gacagcaaac tttttttttat ttcaaattca agtaactgga aggaaggccg      6720
tataccgttg ctcattagag agtagtgtgc gtgaatgaag gaaggaaaaa gtttcgtgtg      6780
cttcgagata cccctcatca gctctggaac aacgacatct gttggtgctg tctttgtcgt      6840 taatttttttc ctttagtgtc ttccatcatt tttttgtcat tgcggatatg gtgagacaac      6900
aacgggggag agagaaaaga aaaaaaaaga aaagaagttg catgcgccta ttattacttc      6960
aatagatggc aaatgaaaa  agggtagtga aacttcgata tgatgatggc tatcaagtct      7020
agggctacag tattagttcg ttatgtacca ccatcaatga ggcagtgtaa ttggtgtagt      7080
```

```
cttgtttagc ccattatgtc ttgtctggta tctgttctat tgtatatctc ccctccgcca    7140
cctacatgtt agggagacca acgaaggtat tataggaatc ccgatgtatg ggtttggttg    7200
ccagaaaaga ggaagtccat attgtacacc cggaaacaac aaaaggatgc gcgcttggcg    7260
taatcatggt catagctgtt tcctgtgtga aattgttatc cgctcacaat tccacacaac    7320
ataggagccg gaagcataaa gtgtaaagcc tggggtgcct aatgagtgag gtaactcaca    7380
ttaattgcgt tgcgctcact gcccgctttc cagtcgggaa acctgtcgtg ccagctgcat    7440
taatgaatcg gccaacgcgc ggggagaggc ggtttgcgta ttgggcgctc ttccgcttcc    7500
tcgctcactg actcgctgcg ctcggtcgtt cggctgcggc gagcggtatc agctcactca    7560
aaggcggtaa tacggttatc cacagaatca ggggataacg caggaaagaa catgtgagca    7620
aaaggccagc aaaaggccag gaaccgtaaa aaggccgcgt tgctggcgtt tttccatagg    7680
ctccgccccc ctgacgagca tcacaaaaat cgacgctcaa gtcagaggtg gcgaaacccg    7740
acaggactat aaagatacca ggcgtttccc cctggaagct ccctcgtgcg ctctcctgtt    7800
ccgaccctgc cgcttaccgg atacctgtcc gcctttctcc cttcgggaag cgtggcgctt    7860
tctcatagct cacgctgtag gtatctcagt tcggtgtagg tcgttcgctc caagctgggc    7920
tgtgtgcacg aaccccccgt tcagcccgac cgctgcgcct tatccggtaa ctatcgtctt    7980
gagtccaacc cggtaagaca cgacttatcg ccactggcag cagccactgg taacaggatt    8040
agcagagcga ggtatgtagg cggtgctaca gagttcttga agtggtggcc taactacggc    8100
tacactagaa ggacagtatt tggtatctgc gctctgctga agccagttac cttcggaaaa    8160
agagttggta gctcttgatc cggcaaacaa accaccgctg gtagcggtgg tttttttgtt    8220
tgcaagcagc agattacgcg cagaaaaaaa ggatctcaag aagatccttt gatcttttct    8280
acggggtctg acgctcagtg gaacgaaaac tcacgttaag ggattttggt catgagatta    8340
tcaaaaagga tcttcaccta gatcctttta aattaaaaat gaagttttaa atcaatctaa    8400
agtatatatg agtaaacttg gtctgacagt taccaatgct taatcagtga ggcacctatc    8460
tcagcgatct gtctatttcg ttcatccata gttgcctgac tccccgtcgt gtagataact    8520
acgatacggg agggcttacc atctggcccc agtgctgcaa tgataccgcg agacccacgc    8580
tcaccggctc cagatttatc agcaataaac cagccagccg gaagggccga gcgcagaagt    8640
ggtcctgcaa ctttatccgc ctccatccag tctattaatt gttgccggga agctagagta    8700
agtagttcgc cagttaatag tttgcgcaac gttgttgcca ttgctacagg catcgtggtg    8760
tcacgctcgt cgtttggtat ggcttcattc agctccggtt cccaacgatc aaggcgagtt    8820
acatgatccc ccatgttgtg caaaaaagcg gttagctcct tcggtcctcc gatcgttgtc    8880
agaagtaagt tggccgcagt gttatcactc atggttatgg cagcactgca taattctctt    8940
actgtcatgc catccgtaag atgcttttct gtgactggtg agtactcaac caagtcattc    9000
tgagaatagt gtatgcggcg accgagttgc tcttgcccgg cgtcaatacg ggataatacc    9060
gcgccacata gcagaacttt aaaagtgctc atcattggaa aacgttcttc ggggcgaaaa    9120
ctctcaagga tcttaccgct gttgagatcc agttcgatgt aacccactcg tgcacccaac    9180
tgatcttcag catcttttac tttcaccagc gtttctgggt gagcaaaaac aggaaggcaa    9240
aatgccgcaa aaaagggaat aagggcgaca cggaaatgtt gaatactcat actcttcctt    9300
tttcaatatt attgaagcat ttatcagggt tattgtctca tgagcggata catatttgaa    9360
tgtatttaga aaaataaaca ataggggtt ccgcgcacat ttccccgaaa agtgccacct    9420
```

```
gggtcctttt catcacgtgc tataaaaata attataattt aaatttttta atataaatat    9480
ataaattaaa aatagaaagt aaaaaaagaa attaaagaaa aaatagtttt tgttttccga    9540
agatgtaaaa gactctaggg ggatcgccaa caaatactac cttttatctt gctcttcctg    9600
ctctcaggta ttaatgccga attgtttcat cttgtctgtg tagaagacca cacacgaaaa    9660
tcctgtgatt ttacatttta cttatcgtta atcgaatgta tatctattta atctgctttt    9720
cttgtctaat aaatatatat gtaaagtacg ctttttgttg aaattttta aacctttgtt    9780
tattttttt tcttcattcc gtaactcttc taccttcttt atttactttc taaaatccaa    9840
atacaaaaca taaaaataaa taaacacaga gtaaattccc aaattattcc atcattaaaa    9900
gatacgaggc gcgtgtaagt tacaggcaag cgatccgtcc taagaaacca ttattatcat    9960
gacattaacc tataaaaata ggcgtatcac gaggcccttt cgtc                    10004

<210> SEQ ID NO 3
<211> LENGTH: 9508
<212> TYPE: DNA
<213> ORGANISM: Artificial Sequence
<220> FEATURE:
<223> OTHER INFORMATION: Codon optimized

<400> SEQUENCE: 3
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcgggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tctttttcta     300
ttactcttgg cctcctaacg acattactat atatataata taggaagcat ttaatagaca     360
gcatcgtaat atatgtgtac tttgcagtta tgacgccaga tggcagtagt ggaagatatt     420
ctttattgaa aaatagcttg tcaccttacg tacaatcttg atccggagct tttctttttt     480
tgccgattaa gaattaattc ggtcgaaaaa agaaaaggag agggccaaga gggagggcat     540
tggtgactat tgagcacgtg agtatacgtg attaagcaca caaaggcagc ttggagtatg     600
tctgttatta atttcacagg tagttctggt ccattggtga agtttgcgg cttgcagagc     660
acagaggccg cagaatgtgc tctagattcc gatgctgact tgctgggtat tatatgtgtg     720
cccaatagaa agagaacaat tgacccggtt attgcaagga aaatttcaag tcttgtaaaa     780
gcatataaaa atagttcagg cactccgaaa tacttggttg gcgtgtttcg taatcaacct     840
aaggaggatg ttttggctct ggtcaatgat tacggcattg atatcgtcca actgcatgga     900
gatgagtcgt ggcaagaata ccaagagttc ctcggttgc cagttattaa agactcgta     960
tttccaaaag actgcaacat actactcagt gcagcttcac agaaacctca ttcgtttatt    1020
cccttgtttg attcagaagc aggtgggaca ggtgaacttt tggattggaa ctcgatttct    1080
gactgggttg gaaggcaaga gagccccgaa agcttacatt ttatgttagc tggtggactg    1140
acgccagaaa atgttggtga tgcgcttaga ttaaatggcg ttattggtgt tgatgtaagc    1200
ggaggtgtgg agacaaatgg tgtaaaagac tctaacaaaa tagcaaattt cgtcaaaaat    1260
gctaagaaat agtgacaccg attatttaaa gctgcagcat acgatatata tacatgtgta    1320
tatatgtata cctatgaatg tcagtaagta tgtatacgaa cagtatgata ctgaagatga    1380
caaggtaatg catcattcta tacgtgtcat tctgaacgag gcgcgctttc cttttttctt    1440
tttgctttt cttttttttt ctcttgaact cgacggatct atgcggtgtg aaataccgca    1500
```

```
cagatgcgta aggagaaaat accgcatcag gaaattgtaa acgttaatat tttgttaaaa    1560
ttcgcgttaa attttgtta aatcagctca ttttttaacc aataggccga aatcggcaaa    1620
atcccttata aatcaaaaga atagaccgag atagggttga gtgttgttcc agtttggaac    1680
aagagtccac tattaaagaa cgtggactcc aacgtcaaag gcgaaaaac cgtctatcag    1740 ggcgatggcc cactacgtga accatcaccc taatcaagtt ttttggggtc gaggtgccgt    1800
aaagcactaa atcggaaccc taaagggagc ccccgattta gagcttgacg gggaaagccg    1860
gcgaacgtgg cgagaaagga agggaagaaa gcgaaaggag cgggcgctag ggcgctggca    1920
agtgtagcgg tcacgctgcg cgtaaccacc acacccgccg cgcttaatgc gccgctacag    1980
ggcgcgtcgc gccattcgcc attcaggctg cgcaactgtt gggaagggcg atcggtgcgg    2040
gcctcttcgc tattacgcca gctggcgaaa ggggatgtg ctgcaaggcg attaagttgg    2100
gtaacgccag ggttttccca gtcacgacgt tgtaaaacga cggccagtga gcgcgcgtaa    2160
tacgactcac tatagggcga attgggtacc ggccgcaaat taaagccttc gagcgtccca    2220
aaaccttctc aagcaaggtt ttcagtataa tgttacatgc gtacacgcgt ctgtacagaa    2280 aaaaagaaa aatttgaaat ataaataacg ttcttaatac taacataact ataaaaaaat    2340
aaatagggac ctagacttca ggttgtctaa ctccttcctt ttcggttaga gcggatgtgg    2400 ggggaggggcg tgaatgtaag cgtgacataa ctaattacat gactcgaggt cgacttacaa    2460
atcttcttca cttattaatt tttgttcgtg gtggtgaggt ggcaaaggtg ggatggattg    2520
ttcgtttctg aaaaagttgt tagggtcggc tttagtcttt actttaacta atctgttgaa    2580 attttacca aagtactttt caccccaaat tcttgcttgt gtatagttat ttggagattc    2640
agggttagtt ttacctaagt ccaaatctct gtagttcaaa tatgccaatc ttgggttttg    2700
actaacgtaa ggtgtagtga agttgtaaac ggatctgacc cagttgatat gcttttcgtt    2760
atcttcttgc ttttcccatg aggctgtgta ccataattca tacatgatac cagctctgtg    2820
aggaaatggt atggctgatt cagatatttc ttccataata ccaccgtatg gatacaaaac    2880
gtacatgccg acacctacat cttcttcgta caacttttcc aatatcttga ccattgcagt    2940
ttcagggatt ggtttcttaa cgtagtccaa tttaatagaa aaagcggtct ttttaccagc    3000
ggatctatcc aacaagattt cctttttgaa gttagcggtg ttgaagttta caacacctga    3060
atagaagatg ttgtgtcta tccaagaaaa ttccttgcaa tctgtctttt taatacccaa    3120
ttctgggaat gacttattca tcaaatcaac caaagaatct acaccaccat ggaaaattga    3180
agaaaaataa ccgtgaacag tggtcttatt tttaccatgg ttatctgtaa tatttttagt    3240
gatgaaatgg gtcatcaaaa ccaagtcctt atcgtacttg taagcgatgt tttgccactt    3300
attaaacaac ttaccaaac cgtggatttc catgttcttt ttgacagaga aaatagtact    3360
tttggaagga acagcgacta acttaatttt ccaagcggca atgataccga aattttcacc    3420
accaccacct cttatggccc aaaacaaatc ttcacccata gactttctgt ccaaaacttt    3480
accatctacg ttaaccaaat gggcgtctat aatattatct gcagctaaac cgtagtttct    3540
catcaatgca ccataaccac caccagaaaa gtgaccaccg acacctactg ttggacagta    3600
accaccaggg aaagaaaagt tttcattctt ttcgttgatc cagtagtaaa cttcacccaa    3660
ggtggcacct gcttctaccc atgctgtttg actgtgaacg tcgatcttta tggaatgcat    3720
atttctcaaa tcgactacaa cgaatggaac ttgtgagatg taagcatgc cttctgcatc    3780 atgaccacct gatctagttc tgatttgcaa acctactttc ttagagcaca atatagaagc    3840
```

```
ttgaatgtga ctaacattgg aaggtgtaac aatgactaaa ggttttggtg tagtgtcaga    3900
agtgaatctc aaattttgga tggtactgtt caaaacggac atgtacaatt gatcatgttg    3960
agtatatata aactttgggt tagcagggtt gtttgggatg tattcggaga aacacttcaa    4020
aaagttttct tgtggatttg cgatggagat ttggatgttg aaggacaaga agaagaagat    4080
tattttacag acgaaccaga aagagaatgc ggagcagttc ataggacctg gattttcttc    4140
aacgtcacca caggtcaaca aagaacctct accttcaata aaaacgtata ccaaatattc    4200
agcgtagtac aatttccaca taaactcgta gaatcttcta cctgcttcag ggtcataatt    4260
tgtcaaagcg aaatctctag tttgcaagat caaccagaaa gccaagatgg catgtgacaa    4320
caacataacg ttagaattaa aggcttgtgg ccaaatgata cctgccaaaa tggctgcgac    4380
gtaacttaac aaaacgatac cggagcagaa caaagtcaaa tttcttgaac cgtacttaga    4440
agccaaggta ctaataccga actttgtgtc accttcaacg tcagaggcat ccttgatcaa    4500
ggctaatgca gaacccatac ttttcatgaa tgccaacaaa aatgtgaatg aaggtctcaa    4560
ttcgaatggc aaacctaaag cagctcttga agcgtagtag aaggtgaagt ttgtgatgat    4620
atgagctaag aaattcaaca aaaggcagt actagggttt tgtttccatc taaaaggtgg     4680
tacgaataga acaataccac cgaagatacc gaaacagtaa ccgaagatgt acaatggacc    4740
acccttcatt ttaattgtga tgatcaaacc gaacaaggct actatgatag acatgatcca    4800
tgcagtattg acggatattt cacctgaagc caaaggcaaa tctggtttgt taattctgtc    4860
gatgtgcaaa tcgtatattt gattaattgt agtggtgaat gaagcgatgc acaagatggc    4920
aactaaaaag aaaaatgcct tgaacatcaa ggaccatgaa attaagttag tgttatgcaa    4980
caattcttta ccgaataaac cgcatgcaca agaagtaaaa gcgattatgg tgtatggtct    5040
ttgcaacttc caacatgctt taccgaagtt caaaattttt gtggcaacag agtgattatc    5100
actttcaggt ggttcagttt gatttgtagt tgcagctctg atagagttct tagctataga    5160
caaactttcg gagcacttat tttgtaagtg aaggacttg gttgaacaat gttttgatgg     5220
aaagttgttg taagagtact taataggtgt ctttggatgt ctgtaacaca acaatgatgt    5280
ttttggattg ttgttgtgag gattcaataa ggtatgatag ttagtttgga aggagaaagt    5340
acagacggat gataaaccca tactagttct agatccgtcg aaactaagtt cttggtgttt    5400
taaaactaaa aaaagactaa actataaaag tagaatttaa gaagtttaag aaatagatt    5460 acagaattac aatcaatacc taccgtcttt atatacttat tagtcaagta ggggaataat    5520
ttcagggaac tggtttaaac cttttttttc agcttttcc aaatcagaga gagcagaagg     5580
taatagaagg tgtaagaaaa tgagatagat acatgcgtgg gtcaattgcc ttgtgtcatc    5640
atttactcca ggcaggttgc atcactccat tgaggttgtg cccgtttttt gcctgtttgt    5700
gccctgttct ctgtagttgc gctaagagaa tggacctatg aactgatggt tggtgaagaa    5760
aacaatattt tggtgctggg attctttttt tttctggatg ccagcttaaa aagcgggctc    5820
cattatattt agtggatgcc aggaataaac ctgttcaccc aagcaccatc agtgttatat    5880
attctgtgta acccgccccc tattttggca tgtacgggtt acagcagaat taaaaggcta    5940
attttttgac taaataaagt taggaaaatc actactatta attatttacg tattctttga    6000
aatggcagta ttgataatga taaactcgag agctccagct tttgttcagt tgattgtatg    6060
cttggtatag cttgaaatat tgtgcagaaa aagaaacaag gaagaaaggg aacgagaaca    6120
atgacgagga aacaaaagat taataattgc aggtctattt atacttgata gcaagacagc    6180
aaactttttt ttatttcaaa ttcaagtaac tggaaggaag gccgtatacc gttgctcatt    6240
```

```
agagagtagt gtgcgtgaat gaaggaagga aaaagtttcg tgtgcttcga gatacccctc    6300
atcagctctg gaacaacgac atctgttggt gctgtctttg tcgttaattt tttcctttag    6360
tgtcttccat catttttttg tcattgcgga tatggtgaga caacaacggg ggagagagaa    6420 aagaaaaaa aagaaaagaa gttgcatgcg cctattatta cttcaataga tggcaaatgg    6480
aaaaagggta gtgaaacttc gatatgatga tggctatcaa gtctagggct acagtattag    6540
ttcgttatgt accaccatca atgaggcagt gtaattggtg tagtcttgtt tagcccatta    6600
tgtcttgtct ggtatctgtt ctattgtata tctcccctcc gccacctaca tgttagggag    6660
accaacgaag gtattatagg aatcccgatg tatgggtttg gttgccagaa aagaggaagt    6720
ccatattgta cacccggaaa caacaaaagg atgcgcgctt ggcgtaatca tggtcatagc    6780
tgtttcctgt gtgaaattgt tatccgctca caattccaca caacatagga gccggaagca    6840
taaagtgtaa agcctggggt gcctaatgag tgaggtaact cacattaatt gcgttgcgct    6900
cactgcccgc tttccagtcg ggaaacctgt cgtgccagct gcattaatga atcggccaac    6960
gcgcggggag aggcggtttg cgtattgggc gctcttccgc ttcctcgctc actgactcgc    7020
tgcgctcggt cgttcggctg cggcgagcgg tatcagctca ctcaaaggcg gtaatacggt    7080
tatccacaga atcaggggat aacgcaggaa agaacatgtg agcaaaaggc cagcaaaagg    7140
ccaggaaccg taaaaaggcc gcgttgctgg cgtttttcca taggctccgc cccccctgacg    7200 agcatcacaa aaatcgacgc tcaagtcaga ggtggcgaaa cccgacagga ctataaagat    7260
accaggcgtt tcccctgga agctccctcg tgcgctctcc tgttccgacc ctgccgctta    7320
ccggatacct gtccgccttt ctcccttcgg gaagcgtggc gctttctcat agctcacgct    7380
gtaggtatct cagttcggtg taggtcgttc gctccaagct gggctgtgtg cacgaacccc    7440
ccgttcagcc cgaccgctgc gccttatccg gtaactatcg tcttgagtcc aacccggtaa    7500
gacacgactt atcgccactg gcagcagcca ctggtaacag gattagcaga gcgaggtatg    7560
taggcggtgc tacagagttc ttgaagtggt ggcctaacta cggctacact agaaggacag    7620
tatttggtat ctgcgctctg ctgaagccag ttaccttcgg aaaaagagtt ggtagctctt    7680
gatccggcaa acaaaccacc gctggtagcg gtggtttttt tgtttgcaag cagcagatta    7740
cgcgcagaaa aaaaggatct caagaagatc ctttgatctt ttctacgggg tctgacgctc    7800
agtggaacga aaactcacgt taagggattt tggtcatgag attatcaaaa aggatcttca    7860
cctagatcct tttaaattaa aaatgaagtt ttaaatcaat ctaaagtata tatgagtaaa    7920
cttggtctga cagttaccaa tgcttaatca gtgaggcacc tatctcagcg atctgtctat    7980
ttcgttcatc catagttgcc tgactccccg tcgtgtagat aactacgata cgggagggct    8040
taccatctgg ccccagtgct gcaatgatac cgcgagaccc acgctcaccg gctccagatt    8100
tatcagcaat aaaccagcca gccggaaggg ccgagcgcag aagtggtcct gcaactttat    8160
ccgcctccat ccagtctatt aattgttgcc gggaagctag agtaagtagt tcgccagtta    8220
atagtttgcg caacgttgtt gccattgcta caggcatcgt ggtgtcacgc tcgtcgtttg    8280
gtatggcttc attcagctcc ggttcccaac gatcaaggcg agttacatga tcccccatgt    8340
tgtgcaaaaa agcggttagc tccttcggtc ctccgatcgt tgtcagaagt aagttggccg    8400
cagtgttatc actcatggtt atggcagcac tgcataattc tcttactgtc atgccatccg    8460
taagatgctt ttctgtgact ggtgagtact caaccaagtc attctgagaa tagtgtatgc    8520
ggcgaccgag ttgctcttgc ccggcgtcaa tacgggataa taccgcgcca catagcagaa    8580
```

```
ctttaaaagt gctcatcatt ggaaaacgtt cttcggggcg aaaactctca aggatcttac    8640
cgctgttgag atccagttcg atgtaaccca ctcgtgcacc caactgatct tcagcatctt    8700
ttactttcac cagcgtttct gggtgagcaa aaacaggaag gcaaaatgcc gcaaaaaagg    8760
gaataagggc gacacggaaa tgttaatac tcatactctt cctttttcaa tattattgaa    8820
gcatttatca gggttattgt ctcatgagcg gatacatatt tgaatgtatt tagaaaaata    8880
aacaaatagg ggttccgcgc acatttcccc gaaaagtgcc acctgggtcc ttttcatcac    8940
gtgctataaa aataattata atttaaattt tttaatataa atatataaat taaaaataga    9000
aagtaaaaaa agaaattaaa gaaaaaatag ttttgttttt ccgaagatgt aaaagactct    9060
agggggatcg ccaacaaata ctacctttta tcttgctctt cctgctctca ggtattaatg    9120
ccgaattgtt tcatcttgtc tgtgtagaag accacacacg aaaatcctgt gattttacat    9180
tttacttatc gttaatcgaa tgtatatcta tttaatctgc ttttcttgtc taataaatat    9240
atatgtaaag tacgcttttt gttgaaattt tttaaaccttt tgtttatttt tttttcttca    9300
ttccgtaact cttctacctt ctttatttac tttctaaaat ccaaatacaa aacataaaaa    9360
taaataaaca cagagtaaat tcccaaatta ttccatcatt aaaagatacg aggcgcgtgt    9420
aagttacagg caagcgatcc gtcctaagaa accattatta tcatgacatt aacctataaa    9480
aataggcgta tcacgaggcc ctttcgtc                                       9508

<210> SEQ ID NO 4
<211> LENGTH: 9505
<212> TYPE: DNA
<213> ORGANISM: Artificial Sequence
<220> FEATURE:
<223> OTHER INFORMATION: Codon optimized

<400> SEQUENCE: 4
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcgggctgg cttaactatg cggcatcaga gcagattgta ctgagagtgc     180
accataaatt cccgtttta gagcttggtg agcgctagga gtcactgcca ggtatcgttt     240
gaacacggca ttagtcaggg aagtcataac acagtccttt cccgcaattt tctttttcta     300
ttactcttgg cctcctaacg acattactat atatataata taggaagcat ttaatagaca     360
gcatcgtaat atatgtgtac tttgcagtta tgacgccaga tggcagtagt ggaagatatt     420
ctttattgaa aaatagcttg tcaccttacg tacaatcttg atccggagct tttctttttt     480
tgccgattaa gaattaattc ggtcgaaaaa agaaaaggag agggccaaga gggagggcat     540
tggtgactat tgagcacgtg agtatacgtg attaagcaca caaaggcagc ttggagtatg     600
tctgttatta atttcacagg tagttctggt ccattggtga agtttgcgg cttgcagagc     660
acagaggccg cagaatgtgc tctagattcc gatgctgact tgctgggtat tatatgtgtg     720
cccaatagaa agagaacaat tgacccggtt attgcaagga aaatttcaag tcttgtaaaa     780
gcatataaaa atagttcagg cactccgaaa tacttggttg cgtgtttcg taatcaacct     840
aaggaggatg ttttggctct ggtcaatgat tacggcattg atatcgtcca actgcatgga     900
gatgagtcgt ggcaagaata ccaagagttc ctcggtttgc cagttattaa aagactcgta     960
tttccaaaag actgcaacat actactcagt gcagcttcac agaaacctca ttcgtttatt    1020
cccttgtttg attcagaagc aggtgggaca ggtgaacttt tggattggaa ctcgatttct    1080
gactgggttg gaaggcaaga gagccccgaa agcttacatt ttatgttagc tggtggactg    1140
```

```
acgccagaaa atgttggtga tgcgcttaga ttaaatggcg ttattggtgt tgatgtaagc    1200
ggaggtgtgg agacaaatgg tgtaaaagac tctaacaaaa tagcaaattt cgtcaaaaat    1260
gctaagaaat agtgacaccg attatttaaa gctgcagcat acgatatata tacatgtgta    1320
tatatgtata cctatgaatg tcagtaagta tgtatacgaa cagtatgata ctgaagatga    1380
caaggtaatg catcattcta tacgtgtcat tctgaacgag gcgcgctttc ctttttttctt    1440 tttgctttt cttttttttt ctcttgaact cgacggatct atgcggtgtg aaataccgca    1500
cagatgcgta aggagaaaat accgcatcag gaaattgtaa acgttaatat tttgttaaaa    1560
ttcgcgttaa attttgtta aatcagctca ttttttaacc aataggccga aatcggcaaa    1620
atcccttata aatcaaaaga atagaccgag atagggttga gtgttgttcc agtttggaac    1680
aagagtccac tattaaagaa cgtggactcc aacgtcaaag ggcgaaaaac cgtctatcag    1740
ggcgatggcc cactacgtga accatcaccc taatcaagtt ttttgggggtc gaggtgccgt    1800 aaagcactaa atcggaaccc taaagggagc ccccgattta gagcttgacg gggaaagccg    1860
gcgaacgtgg cgagaaagga agggaagaaa gcgaaaggag cgggcgctag ggcgctggca    1920
agtgtagcgg tcacgctgcg cgtaaccacc acacccgccg cgcttaatgc gccgctacag    1980
ggcgcgtcgc gccattcgcc attcaggctg cgcaactgtt gggaagggcg atcggtgcgg    2040
gcctcttcgc tattacgcca gctggcgaaa ggggatgtg ctgcaaggcg attaagttgg    2100
gtaacgccag ggttttccca gtcacgacgt tgtaaaacga cggccagtga gcgcgcgtaa    2160
tacgactcac tatagggcga attgggtacc ggccgcaaat taaagccttc gagcgtccca    2220
aaaccttctc aagcaaggtt ttcagtataa tgttacatgc gtacacgcgt ctgtacagaa    2280 aaaaagaaa aatttgaaat ataaataacg ttcttaatac taacataact ataaaaaaat    2340
aaatagggac ctagacttca ggttgtctaa ctccttcctt ttcggttaga gcggatgtgg    2400
ggggagggcg tgaatgtaag cgtgacataa ctaattacat gactcgaggt cgacttacaa    2460
atcttcttca cttattaatt tttgttcgtg tctatgtcta ggtaaaggtg aatggattg    2520 ttcgtttcta aagaagttgt ttgggtcaac caatgtctta accttttacta atctatcgaa    2580 attttttaccg aagtattttt cacccccaaat tctagcttgg gtatagttgt taggattctt    2640
tggatcgtta ataccgatgt ccaaatctct gtagttcaaa tatgccaatc tagggttttt    2700
agaaacgtat ggagtcatga agtttatagat gtttctaatc cagtttaagt gcttttcgtt    2760
atcttcttgc ttttcccatg aacaaatgta ccacaattcg tataagatac cagctctatg    2820
aggaaatgga atgcagatt cactgatttc gtccattata ccaccgtatg gatacaaggc    2880
gtacatgcct gcaccaatat cttcttcgta caatttttct aagatttgga cgaaaactga    2940
ttcaggtatt ggctttttaa cgtagtctaa cttaattta aaggcaccgt ttgacctgc    3000 ggatctatcc aataatattt ctttgttgaa gttgtctgta tcgtagttga caacacctga    3060 ataaagatg atggtgtcga tccaagacaa ttgtctacaa tcagttttct taatacctaa    3120
ttctggaaaa gacttattca tcaagtctac taaggaatcg acaccaccca agaaaactga    3180
agaaaagtat gtgtggatag cagtcttatt tttaccttgg ttatcggtga tgtttcttgt    3240
gatgaaatga gtcatcaaca acaagtcctt atcgtacttg tatgcgatgt tttgccactt    3300
attgaccaat ttaactaatt catggatttc cattatcttt ttgactgaga acatagtaga    3360
ctttggtact gcgactaatc ttatcttcca agcaactatg ataccgaatg attctgcacc    3420
accacctctc aaagcccaaa ataagtcttc acccatagac tttctatcca aaactttacc    3480
```

```
gtgaacattt accaaatgag cgtcgattat gttatcagcg gccaaaccgt agtttctcat   3540
taaaggacca taaccaccac caccaaaatg accacctgcg caaactgttg gacagtaacc   3600
agcagccaat gataagtttt cattcttttc gttaacccag tagtatactt cacccaatgt   3660
tgcaccagct tcaacccaag cagtttgtga gtgtacgtct attttaattg atctcatgtt   3720
tctcaaatca acgataacga atggaacttg ggagatgtat gacatgcctt cactatcatg   3780
accaccggat ctagttctaa tttgcaaacc aaccttttta gaacataaga tagtaccttg   3840
gatgtgagat acatgactag gggttacaat gaccaaaggt tttggagtgg tatcagaagt   3900
gaatctcaaa ttatggattg tactgttcaa gacggacatg tacaatgggt tgttttgagt   3960
gtaaaccaac ttcaaattgg tggcgttatt aggtatgtat tgtgagaagc acttcaaaaa   4020
gttttctctt gggtttgcga tacttgtttg gatgttaaag gaaaagaaaa agaagatgat   4080
cttgcatacg aaccaaaagg agaaagttga acatttcata ggacctggat tttcttcaac   4140
gtcaccacag gtcaacaaag aacctctacc ttcaataaaa acgtatacca aatattcagc   4200
gtagtacaat ttccacataa actcgtagaa tcttctacct gcttcagggt cataatttgt   4260
caaagcgaaa tctctagttt gcaagatcaa ccagaaagcc aagatggcat gtgacaacaa   4320
cataacgtta gaattaaagg cttgtggcca atgatacct gccaaaatgg ctgcgacgta   4380
acttaacaaa acgataccgg agcagaacaa agtcaaattt cttgaaccgt acttagaagc   4440
caaggtacta ataccgaact ttgtgtcacc ttcaacgtca gaggcatcct tgatcaaggc   4500
taatgcagaa cccatacttt tcatgaatgc caacaaaaat gtgaatgaag gtctcaattc   4560
gaatggcaaa cctaaagcag ctcttgaagc gtagtagaag gtgaagtttg tgatgatatg   4620
agctaagaaa ttcaacaaaa aggcagtact agggttttgt ttccatctaa aaggtggtac   4680
ggaatagaca ataccaccga agataccgaa acagtaaccg aagatgtaca atggaccacc   4740
cttcatttta attgtgatga tcaaaccgaa caaggctact atgatagaca tgatccatgc   4800
agtattgacg atatttcac ctgaagccaa aggcaaatct ggtttgttaa ttctgtcgat   4860
gtgcaaatcg tatatttgat taattgtagt ggtgaatgaa gcgatgcaca agatggcaac   4920 taaaagaaa aatgccttga acatcaagga ccatgaaatt aagttagtgt tatgcaacaa   4980
ttctttaccg aataaaccgc atgcacaaga agtaaaagcg attatggtgt atggtctttg   5040
caacttccaa catgctttac cgaagttcaa aatttttgtg gcaacagagt gattatcact   5100
ttcaggtggt tcagtttgat ttgtagttgc agctctgata gagttcttag ctatagacaa   5160
actttcggag cacttatttt gtaagtggaa ggacttggtt gaacaatgtt ttgatggaaa   5220
gttgttgtaa gagtacttaa taggtgtctt tggatgtctg taacacaaca atgatgtttt   5280
tggattgttg ttgtgaggat tcaataaggt atgatagtta gtttggaagg agaaagtaca   5340
gacggatgat aaacccatac tagttctaga tccgtcgaaa ctaagttctt ggtgttttaa   5400
aactaaaaaa aagactaact ataaaagtag aatttaagaa gtttaagaaa tagatttaca   5460
gaattacaat caatacctac cgtctttata tacttattag tcaagtaggg gaataatttc   5520
agggaactgg tttaaacctt ttttttcagc ttttttccaaa tcagagagag cagaaggtaa   5580
tagaaggtgt aagaaaatga gatagataca tgcgtgggtc aattgccttg tgtcatcatt   5640
tactccaggc aggttgcatc actccattga ggttgtgccc gttttttgcc tgtttgtgcc   5700
ctgttctctg tagttgcgct aagagaatgg acctatgaac tgatggttgg tgaagaaaac   5760 aatatttgg tgctgggatt ctttttttt ctggatgcca gcttaaaaag cgggctccat   5820
tatatttagt ggatgccagg aataaacctg ttcacccaag caccatcagt gttatatatt   5880
```

```
ctgtgtaacc cgccccctat tttggcatgt acgggttaca gcagaattaa aaggctaatt    5940
ttttgactaa ataaagttag gaaaatcact actattaatt atttacgtat tctttgaaat    6000
ggcagtattg ataatgataa actcgagagc tccagctttt gttcagttga ttgtatgctt    6060
ggtatagctt gaaatattgt gcagaaaaag aaacaaggaa gaaagggaac gagaacaatg    6120
acgaggaaac aaaagattaa taattgcagg tctatttata cttgatagca agacagcaaa    6180
cttttttta tttcaaattc aagtaactgg aaggaaggcc gtataccgtt gctcattaga    6240
gagtagtgtg cgtgaatgaa ggaaggaaaa agtttcgtgt gcttcgagat acccctcatc    6300
agctctggaa caacgacatc tgttggtgct gtctttgtcg ttaattttt cctttagtgt    6360
cttccatcat ttttttgtca ttgcggatat ggtgagacaa caacggggga gagagaaaag    6420
aaaaaaaag aaaagaagtt gcatgcgcct attattactt caatagatgg caaatggaaa    6480
aagggtagtg aaacttcgat atgatgatgg ctatcaagtc tagggctaca gtattagttc    6540
gttatgtacc accatcaatg aggcagtgta attggtgtag tcttgtttag cccattatgt    6600
cttgtctggt atctgttcta ttgtatatct cccctccgcc acctacatgt tagggagacc    6660
aacgaaggta ttataggaat cccgatgtat gggtttggtt gccagaaaag aggaagtcca    6720
tattgtacac ccggaaacaa caaaaggatg cgcgcttggc gtaatcatgg tcatagctgt    6780
ttcctgtgtg aaattgttat ccgctcacaa ttccacacaa cataggagcc ggaagcataa    6840
agtgtaaagc ctggggtgcc taatgagtga ggtaactcac attaattgcg ttgcgctcac    6900
tgcccgcttt ccagtcggga aacctgtcgt gccagctgca ttaatgaatc ggccaacgcg    6960
cggggagagg cggtttgcgt attgggcgct cttccgcttc ctcgctcact gactcgctgc    7020
gctcggtcgt tcggctgcgg cgagcggtat cagctcactc aaaggcggta atacggttat    7080
ccacagaatc aggggataac gcaggaaaga acatgtgagc aaaaggccag caaaaggcca    7140
ggaaccgtaa aaaggccgcg ttgctggcgt ttttccatag gctccgcccc cctgacgagc    7200
atcacaaaaa tcgacgctca agtcagaggt ggcgaaaccc gacaggacta taaagatacc    7260
aggcgtttcc ccctggaagc tccctcgtgc gctctcctgt tccgaccctg ccgcttaccg    7320
gatacctgtc cgcctttctc ccttcgggaa gcgtggcgct ttctcatagc tcacgctgta    7380
ggtatctcag ttcggtgtag gtcgttcgct ccaagctggg ctgtgtgcac gaaccccccg    7440
ttcagcccga ccgctgcgcc ttatccggta actatcgtct tgagtccaac ccggtaagac    7500
acgacttatc gccactggca gcagccactg gtaacaggat tagcagagcg aggtatgtag    7560
gcggtgctac agagttcttg aagtggtggc ctaactacgg ctacactaga aggacagtat    7620
ttggtatctg cgctctgctg aagccagtta ccttcggaaa aagagttggt agctcttgat    7680
ccggcaaaca aaccaccgct ggtagcggtg gtttttttgt ttgcaagcag cagattacgc    7740
gcagaaaaaa aggatctcaa gaagatcctt tgatctttc tacggggtct gacgctcagt    7800
ggaacgaaaa ctcacgttaa gggattttgg tcatgagatt atcaaaaagg atcttcacct    7860
agatcctttt aaattaaaaa tgaagtttta aatcaatcta agtatatat gagtaaactt    7920
ggtctgacag ttaccaatgc ttaatcagtg aggcacctat ctcagcgatc tgtctatttc    7980
gttcatccat agttgcctga ctccccgtcg tgtagataac tacgatacgg gagggcttac    8040
catctggccc cagtgctgca atgataccgc gagacccacg ctcaccggct ccagatttat    8100
cagcaataaa ccagccagcc ggaagggccg agcgcagaag tggtcctgca actttatccg    8160
cctccatcca gtctattaat tgttgccggg aagctagagt aagtagttcg ccagttaata    8220
```

```
gtttgcgcaa cgttgttgcc attgctacag gcatcgtggt gtcacgctcg tcgtttggta      8280
tggcttcatt cagctccggt tcccaacgat caaggcagt tacatgatcc cccatgttgt       8340
gcaaaaaagc ggttagctcc ttcggtcctc cgatcgttgt cagaagtaag ttggccgcag      8400
tgttatcact catggttatg gcagcactgc ataattctct tactgtcatg ccatccgtaa      8460
gatgcttttc tgtgactggt gagtactcaa ccaagtcatt ctgagaatag tgtatgcggc      8520
gaccgagttg ctcttgcccg gcgtcaatac gggataatac cgcgccacat agcagaactt      8580
taaaagtgct catcattgga aaacgttctt cggggcgaaa actctcaagg atcttaccgc      8640
tgttgagatc cagttcgatg taacccactc gtgcacccaa ctgatcttca gcatctttta      8700
ctttcaccag cgtttctggg tgagcaaaaa caggaaggca aaatgccgca aaaagggaa      8760 taagggcgac acggaaatgt tgaatactca tactcttcct ttttcaatat tattgaagca      8820
tttatcaggg ttattgtctc atgagcggat acatatttga atgtatttag aaaaataaac      8880
aaatagtggt tccgcgcaca tttccccgaa aagtgccacc tgggtccttt tcatcacgtg      8940
ctataaaaat aattataatt taaattttt aatataaata tataaattaa aaatagaaag      9000 taaaaaaga aattaaagaa aaaatagttt ttgttttccg aagatgtaaa agactctagg      9060
gggatcgcca acaaatacta ccttttatct tgctcttcct gctctcaggt attaatgccg      9120
aattgtttca tcttgtctgt gtagaagacc acacacgaaa atcctgtgat tttacatttt      9180
acttatcgtt aatcgaatgt atatctattt aatctgcttt tcttgtctaa taatatata      9240 tgtaaagtac gcttttgtt gaattttttt aaaccttgt ttattttttt ttcttcattc      9300
cgtaactctt ctaccttctt tatttacttt ctaaaatcca aatacaaaac ataaaaataa      9360
ataaacacag agtaaattcc caaattattc catcattaaa agatacgagg cgcgtgtaag      9420
ttacaggcaa gcgatccgtc ctaagaaacc attattatca tgacattaac ctataaaaat      9480
aggcgtatca cgaggccctt tcgtc                                            9505
```

<210> SEQ ID NO 5
<211> LENGTH: 8696
<212> TYPE: DNA
<213> ORGANISM: Artificial Sequence
<220> FEATURE:
<223> OTHER INFORMATION: Codon optimized

<400> SEQUENCE: 5

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgcgtg      120
ttggcgggtg tcgggctgg cttaactatg cggcatcaga gcagattgta ctgagagtgc       180
accataaatt cccgttttaa gagcttggtg agcgctagga gtcactgcca ggtatcgttt      240
gaacacggca ttagtcaggg aagtcataac acagtccttt cccgcaattt tcttttcta       300 ttactcttgg cctcctaact gtgggaatac tcaggtatcg taagatgcaa gagttcgaat      360
ctcttagcaa ccattatttt tttcctcaac ataacgagaa cacacagggg cgctatcgca      420
cagaatcaaa ttcgatgact ggaaattttt tgttaatttc agaggtcgcc tgacgcatat      480
acctttttca actgaaaaat tgggagaaaa aggaaaggtg agaggccgga accggctttt      540
catatagaat agagaagcgt tcatgactaa atgcttgcat cacaatactt gaagttgaca      600 atattatta aggacctatt gttttttcca ataggtggtt agcaatcgtc ttactttcta      660
acttttctta ccttttacat ttcagcaata tatatatata tttcaaggat ataccattct      720
aatgtctgcc cctatgtctg cccctaagaa gatcgtcgtt ttgccaggtg accacgttgg      780
```

```
tcaagaaatc acagccgaag ccattaaggt tcttaaagct atttctgatg ttcgttccaa    840
tgtcaagttc gatttcgaaa atcatttaat tggtggtgct gctatcgatg ctacaggtgt    900
cccacttcca gatgaggcgc tggaagcctc caagaaggtt gatgccgttt tgttaggtgc    960
tgtgggtggt cctaaatggg gtaccggtag tgttagacct gaacaaggtt tactaaaaat   1020
ccgtaaagaa cttcaattgt acgccaactt aagaccatgt aactttgcat ccgactctct   1080
tttagactta tctccaatca agccacaatt tgctaaaggt actgacttcg ttgttgtcag   1140
agaattagtg ggaggtattt actttggtaa gagaaaggaa gacgatggtg atggtgtcgc   1200 tgggatagt gaacaataca ccgttccaga agtgcaaaga atcacaagaa tggccgcttt   1260
catggcccta acatgagc accattgcc tatttggtcc ttggataaag ctaatgtttt   1320
ggcctcttca agattatgga gaaaaactgt ggaggaaacc atcaagaacg aattccctac   1380
attgaaggtt caacatcaat tgattgattc tgccgccatg atcctagtta agaacccaac   1440
ccacctaaat ggtattataa tcaccagcaa catgtttggt gatatcatct ccgatgaagc   1500
ctccgttatc ccaggttcct tgggtttgtt gccatctgcg tccttggcct ctttgccaga   1560
caagaacacc gcatttggtt tgtacgaacc atgccacggt tctgctccag atttgccaaa   1620
gaataaggtt gaccctatcg ccactatctt gtctgctgca atgatgttga aattgtcatt   1680
gaacttgcct gaagaaggta aggccattga agatgcagtt aaaaaggttt tggatgcagg   1740
tatcagaact ggtgatttag gtggttccaa cagtaccacc gaagtcggtg atgctgtcgc   1800
cgaagaagtt aagaaaatcc ttgcttaatg acaccgatta tttaaagctg cagcatacga   1860
tatatataca tgtgtatata tgtataccta tgaatgtcag taagtatgta tacgaacagt   1920
atgatactga agatgacaag gtaatgcatc attctatacg tgtcattctg aacgaggcgc   1980
gctttccttt tttcttttg cttttctctt tttttctct tgaactcgac ggatctatgc   2040
ggtgtgaaat accgcacaga tgcgtaagga gaaataccg catcaggaaa ttgtaaacgt   2100
taatattttg ttaaaattcg cgttaaattt ttgttaaatc agctcatttt ttaaccaata   2160
ggccgaaatc ggcaaaatcc cttataaatc aaaagaatag accgagatag ggttgagtgt   2220
tgttccagtt tggaacaaga gtccactatt aaagaacgtg gactccaacg tcaaagggcg   2280
aaaaaccgtc tatcagggcg atggcccact acgtgaacca tcaccctaat caagttttt   2340 ggggtcgagg tgccgtaaag cactaaatcg gaaccctaaa gggagccccc gatttagagc   2400
ttgacgggga agccggcga acgtggcgag aaaggaaggg aagaaagcga aaggagcggg   2460
cgctagggcg ctggcaagtg tagcggtcac gctgcgcgta accaccacac ccgccgcgct   2520
taatgcgccg ctacagggcg cgtcgcgcca ttcgccattc aggctgcgca actgttggga   2580
agggcgatcg gtgcgggcct cttcgctatt acgccagctg gcgaaagggg gatgtgctgc   2640
aaggcgatta agttgggtaa cgccagggtt ttcccagtca cgacgttgta aaacgacggc   2700
cagtgagcgc gcgtaatacg actcactata gggcgaattg ggtaccggcc gcaaattaaa   2760
gccttcgagc gtcccaaaac cttctcaagc aaggttttca gtataatgtt acatgcgtac   2820
acgcgtctgt acagaaaaaa aagaaaaatt tgaaatataa ataacgttct taatactaac   2880
ataactataa aaaataaat agggacctag acttcaggtt gtctaactcc ttcctttttcg   2940 gttagagcgg atgtgggggg agggcgtgaa tgtaagcgtg acataactaa ttacatgact   3000
cgaggtcgac ttatgcatag tctggaacat cgtaagggta ctttcttggg gtgtaatcga   3060
agatcaacaa tttttcccag aaggatctgt aaacgtcacc aaaaccaacg tgagctggat   3120
```

```
gaatgatgta atcttggata gtttcaactg attcgaaggt tacttcgaca atgtgtgtat    3180
aaccttcttc tttcttttgt gtaacgtctt tacccagta tacatctttc atagcaggta    3240
taatgttgac caaattaacg taggtcttga aaaattcttc cttttgagct tctgtgattt    3300
catctttaaa cttcaatact atcaaatgct tgacggccat aggacctggg ttttcttcaa    3360
cgtcaccaca agttaacaag gaacctctac cttcatattt aattggtact gatctgacaa    3420
ctactctttc gacggtcaaa ccaggaccga aaccaaataa dacaccccat tcaaaaccgt    3480
caccagtagt agatttaccc tcttctaatg atctctttct caattcatcc attacgaaca    3540
agacagtgga tgaagacatg ttaccgtgtt cagataaaac atgtctacta tctacaaact    3600
tttctttctt caaatccaat ttttcttcaa ccttatccaa aatggcttta ccacctggat    3660
gtgttatcca gaaatagag ttccaatctg atacctat aggagtgaat gcttctatca    3720 aacactttc tatgttgtta gagattaaca ttggaacgtc tttgtgcaaa tcgaagatca    3780
aacctgcttc tcttatatga ccaccaattg taccttcaga attaggcaag atggtttgac    3840
ctgtactgac taattcaaat attggtcttt caccaacaga ttcgtcaggt tctgcaccaa    3900
caataacagc agcagcaccg tcaccgaaga tagcttgacc aactaacaat tccaagtcag    3960
aatcacttgg acctctaaac aagcaagcca taatgtcgca acaaacagct aatactctgg    4020 caccccttgtt gttttctgca atatccttag cgattctcaa aacagtacca ccaccgtagc    4080
aacctaattg atacatcatg actctcttaa cggatggtga caaacctaac aatttggcac    4140
agtggtagtc tgcaccaggc atatctgtag tagatgcact tgtaaaaatc aaatgagtga    4200
tctttgactt tggttgaccc cattccttaa tggcttttgc acaagcatct ttacccaatt    4260
taggaacttc gacaactaac atgtcttgtc tggcatccaa tgtttgcatt tcgtgttcta    4320
ccaatcttgg attttgcttc aaatgttctt cgttcaagaa gcagtttctc tttctgatca    4380
tagacttatc acatattttt ctaaactttt ccttcaattg agtcatgtgt tcactcttgg    4440
taactctgaa gtaataatca ggaaattcat cttggatcaa tatgttttct ggttggctg    4500 tacctatggc taatacggag gcaggacctt cggctctcaa atggttcata ctagttctag    4560
atccgtcgaa actaagttct tggtgtttta aaactaaaaa aaagactaac tataaaagta    4620
gaatttaaga agtttaagaa atagattttac agaattacaa tcaatacctta ccgtctttat    4680 atacttatta gtcaagtagg ggaataattt cagggaactg gtttaaacct ttttttttcag    4740 cttttttccaa atcagagaga gcagaaggta atagaaggtg taagaaaatg agatagatac    4800
atgcgtgggt caattgcctt gtgtcatcat ttactccagg caggttgcat cactccattg    4860
aggttgtgcc cgttttttgc ctgtttgtgc cctgttctct gtagttgcgc taagagaatg    4920
gacctatgaa ctgatggttg gtgaagaaaa caatattttg gtgctgggat tcttttttt    4980 tctggatgcc agcttaaaaa gcgggctcca ttatatttag tggatgccag gaataaacct    5040
gttcacccaa gcaccatcag tgttatatat tctgtgtaac ccgccccct ttttggcatg    5100 tacgggttac agcagaatta aaaggctaat tttttgacta aataaagtta ggaaaatcac    5160
tactattaat tatttacgta ttctttgaaa tggcagtatt gataatgata aactcgagag    5220
ctccagcttt tgttcagttg attgtatgct tggtatagct tgaatattg tgcagaaaaa    5280 gaaacaagga agaagggaa cgagaacaat gacgaggaaa caaaagatta ataattgcag    5340
gtctatttat acttgatagc aagacagcaa acttttttt atttcaaatt caagtaactg    5400
gaaggaaggc cgtataccgt tgctcattag agagtagtgt gcgtgaatga aggaaggaaa    5460
aagtttcgtg tgcttcgaga taccctcat cagctctgga acaacgacat ctgttggtgc    5520
```

```
tgtctttgtc gttaattttt tcctttagtg tcttccatca ttttttttgtc attgcggata    5580 tggtgagaca acaacggggg agagagaaaa gaaaaaaaa gaaagaagt tgcatgcgcc       5640 tattattact tcaatagatg gcaaatggaa aaagggtagt gaaacttcga tatgatgatg     5700
gctatcaagt ctagggctac agtattagtt cgttatgtac caccatcaat gaggcagtgt    5760
aattggtgta gtcttgttta gcccattatg tcttgtctgg tatctgttct attgtatatc    5820
tcccctccgc cacctacatg ttagggagac caacgaaggt attataggaa tcccgatgta    5880
tgggtttggt tgccagaaaa gaggaagtcc atattgtaca cccggaaaca acaaaaggat    5940
gcgcgcttgg cgtaatcatg gtcatagctg tttcctgtgt gaaattgtta ccgctcaca    6000 attccacaca acataggagc cggaagcata aagtgtaaag cctggggtgc ctaatgagtg    6060
aggtaactca cattaattgc gttgcgctca ctgcccgctt tccagtcggg aaacctgtcg    6120
tgccagctgc attaatgaat cggccaacgc gcggggagag gcggtttgcg tattgggcgc    6180
tcttccgctt cctcgctcac tgactcgctg cgctcggtcg ttcggctgcg gcgagcggta    6240
tcagctcact caaaggcggt aatacggtta tccacagaat caggggataa cgcaggaaag    6300
aacatgtgag caaaaggcca gcaaaaggcc aggaaccgta aaaaggccgc gttgctggcg    6360 ttttccata ggctccgccc ccctgacgag catcacaaaa atcgacgctc aagtcagagg     6420
tggcgaaacc cgacaggact ataaagatac caggcgtttc ccctggaag ctccctcgtg     6480 cgctctcctg ttccgaccct gccgcttacc ggatacctgt ccgcctttct cccttcggga    6540
agcgtggcgc tttctcatag ctcacgctgt aggtatctca gttcggtgta ggtcgttcgc    6600
tccaagctgg gctgtgtgca cgaaccccc gttcagcccg accgctgcgc cttatccggt     6660
aactatcgtc ttgagtccaa cccggtaaga cacgacttat cgccactggc agcagccact    6720
ggtaacagga ttagcagagc gaggtatgta ggcggtgcta cagagttctt gaagtggtgg    6780
cctaactacg gctacactag aaggacagta tttggtatct gcgctctgct gaagccagtt    6840
accttcggaa aaagagttgg tagctcttga tccggcaaac aaaccaccgc tggtagcggt    6900
ggtttttttg tttgcaagca gcagattacg cgcagaaaaa aaggatctca agaagatcct    6960
ttgatctttt ctacggggtc tgacgctcag tggaacgaaa actcacgtta agggattttg    7020
gtcatgagat tatcaaaaag gatcttcacc tagatccttt taaattaaaa atgaagtttt    7080
aaatcaatct aaagtatata tgagtaaact tggtctgaca gttaccaatg cttaatcagt    7140
gaggcaccta tctcagcgat ctgtctattt cgttcatcca tagttgcctg actccccgtc    7200
gtgtagataa ctacgatacg ggagggctta ccatctggcc ccagtgctgc aatgataccg    7260
cgagacccac gctcaccggc tccagattta tcagcaataa accagccagc cggaagggcc    7320
gagcgcagaa gtggtcctgc aactttatcc gcctccatcc agtctattaa ttgttgccgg    7380
gaagctagag taagtagttc gccagttaat agtttgcgca acgttgttgc cattgctaca    7440
ggcatcgtgg tgtcacgctc gtcgtttggt atggcttcat tcagctccgg ttcccaacga    7500
tcaaggcgag ttacatgatc ccccatgttg tgcaaaaaag cggttagctc cttcggtcct    7560
ccgatcgttg tcagaagtaa gttggccgca gtgttatcac tcatggttat ggcagcactg    7620
cataattctc ttactgtcat gccatccgta agatgctttt ctgtgactgg tgagtactca    7680
accaagtcat tctgagaata gtgtatgcgg cgaccgagtt gctcttgccc ggcgtcaata    7740
cgggataata ccgcgccaca tagcagaact ttaaaagtgc tcatcattgg aaaacgttct    7800
tcggggcgaa aactctcaag gatcttaccg ctgttgagat ccagttcgat gtaacccact    7860
```

| | |
|---|---|
| cgtgcaccca actgatcttc agcatctttt actttcacca gcgtttctgg gtgagcaaaa | 7920 |
| acaggaaggc aaaatgccgc aaaaaaggga ataagggcga cacggaaatg ttgaatactc | 7980 |
| atactcttcc tttttcaata ttattgaagc atttatcagg gttattgtct catgagcgga | 8040 |
| tacatatttg aatgtattta gaaaaataaa caaatagggg ttccgcgcac atttccccga | 8100 |
| aaagtgccac ctgggtcctt ttcatcacgt gctataaaaa taattataat ttaaattttt | 8160 |
| taatataaat atataaatta aaaatagaaa gtaaaaaaag aaattaaaga aaaaatagtt | 8220 |
| tttgttttcc gaagatgtaa aagactctag ggggatcgcc aacaaatact acctttatc | 8280 |
| ttgctcttcc tgctctcagg tattaatgcc gaattgtttc atcttgtctg tgtagaagac | 8340 |
| cacacacgaa atcctgtga ttttacattt tacttatcgt taatcgaatg tatatctatt | 8400 |
| taatctgctt ttcttgtcta ataaatatat atgtaaagta cgcttttgt tgaaatttt | 8460 |
| taaacctttg tttattttt tttcttcatt ccgtaactct tctaccttct ttatttactt | 8520 |
| tctaaaatcc aaatacaaaa cataaaaata aataaacaca gagtaaattc ccaaattatt | 8580 |
| ccatcattaa aagatacgag gcgcgtgtaa gttacaggca agcgatccgt cctaagaaac | 8640 |
| cattattatc atgacattaa cctataaaaa taggcgtatc acgaggccct ttcgtc | 8696 |

<210> SEQ ID NO 6
<211> LENGTH: 4322
<212> TYPE: DNA
<213> ORGANISM: Artificial Sequence
<220> FEATURE:
<223> OTHER INFORMATION: Codon optimized

<400> SEQUENCE: 6

| | |
|---|---|
| aggaaacgaa gataaatctc gagtttatca ttatcaatac tgccatttca aagaatacgt | 60 |
| aaataattaa tagtagtgat tttcctaact ttatttagtc aaaaaattag cctttaatt | 120 |
| ctgctgtaac ccgtacatgc caaataggg ggcgggttac acagaatata taacactgat | 180 |
| ggtgcttggg tgaacaggtt tattcctggc atccactaaa tataatggag cccgcttttt | 240 |
| aagctggcat ccagaaaaaa aaagaatccc agcaccaaaa tattgttttc ttcaccaacc | 300 |
| atcagttcat aggtccattc tcttagcgca actacagaga acagggcaca aacaggcaaa | 360 |
| aaacgggcac aaccctcaatg gagtgatgca acctgcctgg agtaaatgat gacacaaggc | 420 |
| aattgaccca cgcatgtatc tatctcatt tcttacacct tctattacct tctgctctct | 480 |
| ctgatttgga aaaagctgaa aaaaaaggtt taaaccagtt ccctgaaatt attcccctac | 540 |
| ttgactaata agtatataaa gacggtaggt attgattgta attctgtaaa tctatttctt | 600 |
| aaacttctta aattctactt ttatagttag tcttttttt agttttaaaa caccaagaac | 660 |
| ttagtttcga cggatctaga actagtatgg gtaaaaacta aagtccttg gattcagtcg | 720 |
| ttgcctcaga tttcatcgca ttgggtatca cctcagaagt agcagaaaca ttacatggta | 780 |
| gattggcaga aatcgtttgt aattatggtg ctgcaacccc tcaaacttgg atcaacatcg | 840 |
| ctaaccatat cttgtcacca gatttgcctt tctccttaca ccaaatgttg ttttatggtt | 900 |
| gctacaagga tttcggtcca gccccacctg cttggattcc agaccctgaa aaagtcaagt | 960 |
| caactaattt gggtgctttg ttggaaaaga gaggtaaaga atttttgggt gtaaagtaca | 1020 |
| aagatccaat ttcttctttt tctcacttcc aagaatttc tgttagaaac cctgaagtct | 1080 |
| attggagaac agtattgatg gatgaaatga aaattagttt ctctaaggac ccagaatgta | 1140 |
| tcttgagaag agatgacatc aacaacccag gtggttctga atggttacct ggtggttact | 1200 |
| tgaactcagc taaaaattgc ttgaacgtaa actccaataa gaaattgaac gatactatga | 1260 |

```
tcgtttggag agacgagggt aacgatgact tgcctttgaa taagttgaca ttagatcaat     1320
tgagaaagag agtttggttg gttggttatg cattggaaga atgggttta gaaaaaggtt     1380 gtgcaatagc catcgatatg ccaatgcatg ttgatgctgt tgttatatat ttggccatag     1440
tattggctgg ttacgtagtt gtctctatag cagattcatt ttccgcccct gaaatctcaa     1500
ctagattgag attatccaaa gctaaggcaa ttttcacaca agatcacatc atcagaggta     1560
aaaagagaat accattgtat tcaagagtag ttgaagctaa atccccaatg gcaatagtta     1620
tcccttgtag tggttctaac attggtgcag aattgagaga tggtgacata tcttgggatt     1680
actttttaga aagagccaag gagtttaaaa actgcgagtt tactgccaga gaacaacctg     1740
ttgatgctta tactaacatc ttattctcca gtggtactac aggtgaacca aaagcaattc     1800
cttggacaca agccacccca ttgaaggctg ctgctgatgg ttggtctcat ttggatatta     1860
gaaaaggtga cgttatagta tggccaacta atttgggttg gatgatgggt ccttggttgg     1920
tttatgctag tttgttaaat ggtgcatcta ttgccttgta caacggtagt cctttagtct     1980
ctggtttcgc taaatttgtt caagatgcaa aggtcacaat gttgggtgtc gtaccatcta     2040
ttgtaagatc atggaaatcc acaaattgtg tttcaggtta cgattggtcc accataagat     2100
gcttttcttc atccggtgaa gcctctaatg tagacgaata tttgtggtta atgggtagag     2160
ctaactacaa gccagttata gaaatgtgtg gtggtacaga aatcggtggt gcttttctg     2220 ctggttcatt tttgcaagct caatctttaa gttcttttc atcccaatgt atgggttgca     2280
ccttgtacat attagataag aacggttacc caatgcctaa aaataagcca ggtatcggtg     2340
aattggcatt aggtcctgtt atgtttggtg cctcaaaaac attgttaaac ggtaatcatc     2400
acgatgtcta tttcaagggt atgccaacct tgaatggtga agtattgaga agacatggtg     2460
acattttcga attgacctct aacggttact accatgcaca cggtagagcc gatgacacta     2520
tgaacatcgg tggtatcaaa attagttcta tcgaaatcga aagagtctgt aatgaagtag     2580
atgacagagt ttttgaaacc actgctattg gtgttccacc tttgggtggt ggtccagaac     2640
aattggtcat attttcgta ttgaaggatt caaacgacac aaccattgat ttgaaccaat     2700
tgagattatc ctttaacttg ggtttgcaaa agaaattgaa cccattattc aaagttacta     2760
gagttgtccc attgtcatcc ttacctagaa ctgcaacaaa caagatcatg agaagagttt     2820
tgagacaaca attcagtcat ttcgaagaag gtagaggttc tttgttaaca tgtggtgacg     2880
ttgaagaaaa tccaggtcct atggcttcag aaaaggaaat aagaagagaa agattcttga     2940
acgtattccc aaagtttagtt gaagaattga acgctagttt gttagcttat ggtatgccta     3000
aagaagcctg cgattggtat gctcactctt taaactacaa tactccaggt ggtaaattga     3060
atagaggttt gagtgtagtt gatacttatg ctatcttgtc taacaaaacc gttgaacaat     3120
taggtcaaga agaatacgaa aaggtcgcta tcttgggttg gtgtattgaa ttgttgcaag     3180 catactttt ggttgccgat gacatgatgg ataagtctat aacaagaaga ggtcaaccat     3240
gctggtacaa agttccagaa gttggtgaaa tagccataaa tgatgctttt atgttggaag     3300
ccgctatcta taaattgttg aagtcacatt tcagaaacga aaagtactac atcgatatta     3360
ccgaattatt ccacgaagtt actttccaaa cagaattggg tcaattgatg gatttgataa     3420
ctgcacctga agataaagtt gacttgtcaa agttttcctt gaagaaacat tcattcatcg     3480
tcacctttga aactgcttat tactccttct atttgccagt cgccttggct atgtacgtag     3540
ctggtattac tgatgaaaaa gacttgaagc aagcaagaga tgttttgata cctttgggtg     3600
```

| | | |
|---|---|---|
| aatacttcca aatccaagat gactacttag actgtttcgg tactccagaa caaataggta | 3660 | |
| aaatcggtac agatattcaa gacaataagt gcagttgggt tattaacaag gctttggaat | 3720 | |
| tagcatctgc cgaacaaaga aagactttgg atgaaaacta cggtaaaaag gactcagttg | 3780 | |
| ctgaagcaaa gtgtaagaaa attttttaatg atttgaagat tgaacaattg taccatgaat | 3840 | |
| acgaagaatc catcgctaaa gacttaaagg caaagattag tcaagttgat gaatcaagag | 3900 | |
| gttttaaagc cgacgttttg acagctttct tgaataaggt ctacaagaga tcaaaggatt | 3960 | |
| acaaggatca tgacggtgac tataaagacc acgatattga ctacaaagat gacgatgaca | 4020 | |
| agtaagtcga cctcgagtca tgtaattagt tatgtcacgc ttacattcac gccctccccc | 4080 | |
| cacatccgct ctaaccgaaa aggaaggagt tagacaacct gaagtctagg tccctattta | 4140 | |
| ttttttata gttatgttag tattaagaac gttatttata tttcaaattt ttcttttttt | 4200 | |
| tctgtacaga cgcgtgtacg catgtaacat tatactgaaa accttgcttg agaaggtttt | 4260 | |
| gggacgctcg aaggctttaa tttgcgtgac ataactaatt acatgacttg actgattttt | 4320 | |
| cc | 4322 | |

<210> SEQ ID NO 7
<211> LENGTH: 2522
<212> TYPE: DNA
<213> ORGANISM: Artificial Sequence
<220> FEATURE:
<223> OTHER INFORMATION: Codon optimized

<400> SEQUENCE: 7

| | | |
|---|---|---|
| aggaaacgaa gataaatctc gagtttatca ttatcaatac tgccatttca aagaatacgt | 60 | |
| aaataattaa tagtagtgat tttcctaact ttatttagtc aaaaaattag ccttttaatt | 120 | |
| ctgctgtaac ccgtacatgc caaaataggg ggcgggttac acagaatata taacactgat | 180 | |
| ggtgctgggg tgaacaggtt tattcctggc atccactaaa tataatggag cccgcttttt | 240 | |
| aagctggcat ccagaaaaaa aaagaatccc agcaccaaaa tattgttttc ttcaccaacc | 300 | |
| atcagttcat aggtccattc tcttagcgca actacagaga acagggcaca aacaggcaaa | 360 | |
| aaacgggcac aacctcaatg gagtgatgca acctgcctgg agtaaatgat gacacaaggc | 420 | |
| aattgaccca cgcatgtatc tatctcattt tcttacacct tctattacct tctgctctct | 480 | |
| ctgatttgga aaaagctgaa aaaaaaggtt taaaccagtt ccctgaaatt attcccctac | 540 | |
| ttgactaata agtatataaa gacggtaggt attgattgta attctgtaaa tctatttctt | 600 | |
| aaacttctta aattctactt ttatagttag tcttttttt agttttaaaa caccaagaac | 660 | |
| ttagtttcga cggatctaga actagtatga accatttgag agccgaaggt cctgcctccg | 720 | |
| tattagccat aggtacagcc aacccagaaa acatattgat ccaagatgaa tttcctgatt | 780 | |
| attacttcag agttaccaag agtgaacaca tgactcaatt gaaggaaaag tttagaaaaa | 840 | |
| tatgtgataa gtctatgatc agaaagagaa actgcttctt gaacgaagaa catttgaagc | 900 | |
| aaaatccaag attggtagaa cacgaaatgc aaacattgga tgccagacaa gacatgttag | 960 | |
| ttgtcgaagt tcctaaattg ggtaaagatg cttgtgcaaa agccattaag gaatggggtc | 1020 | |
| aaccaaagtc aaagatcact catttgattt ttacaagtgc atctactaca gatatgcctg | 1080 | |
| gtgcagacta ccactgtgcc aaattgttag gtttgtcacc atccgttaag agagtcatga | 1140 | |
| tgtatcaatt aggttgctac ggtggtggta ctgttttgag aatcgctaag gatattgcag | 1200 | |
| aaaacaacaa gggtgccaga gtattagctg tttgttgcga cattatggct tgcttgttta | 1260 | |
| gaggtccaag tgattctgac ttggaattgt tagttggtca agctatcttc ggtgacggtg | 1320 | |

```
ctgctgctgt tattgttggt gcagaacctg acgaatctgt tggtgaaaga ccaatatttg    1380
aattagtcag tacaggtcaa accatcttgc ctaattctga aggtacaatt ggtggtcata    1440
taagagaagc aggtttgatc ttcgatttgc acaaagacgt tccaatgtta atctctaaca    1500
acatagaaaa gtgtttgata gaagcattca ctcctatagg tatctcagat tggaactcta    1560
ttttctggat aacacatcca ggtggtaaag ccatttttgga taaggttgaa gaaaaattgg    1620
atttgaagaa agaaaagttt gtagatagta gacatgtttt atctgaacac ggtaacatgt    1680
cttcatccac tgtcttgttc gtaatggatg aattgagaaa gagatcatta aagagggta    1740 aatctactac tggtgacggt tttgaatggg gtgtcttatt tggtttcggt cctggtttga    1800
ccgtcgaaag agtagttgtc agatcagtac aattaaaata tgaaggtaga ggttccttgt    1860
taacttgtgg tgacgttgaa gaaaacccag gtcctatggc cgtcaagcat ttgatagtat    1920
tgaagtttaa agatgaaatc acagaagctc aaaaggaaga atttttcaag acctacgtta    1980
atttggtcaa cattataacct gctatgaaag atgtatactg gggtaaagac gttacacaaa    2040
agaaagaaga aggttataca cacattgtcg aagtaaccct cgaatcagtt gaaactatcc    2100
aagattacat cattcatcca gctcacgttg gttttggtga cgtttacaga tccttctggg    2160
aaaaattgtt gatcttcgat tacaccccaa gaaagtaccc ttacgatgtt ccagactatg    2220
cataagtcga cctcgagtca tgtaattagt tatgtcacgc ttacattcac gccctccccc    2280
cacatccgct ctaaccgaaa aggaaggagt tagacaacct gaagtctagg tccctattta    2340 ttttttttata gttatgttag tattaagaac gttatttata tttcaaatttt ttctttttt    2400 tctgtacaga cgcgtgtacg catgtaacat tatactgaaa accttgcttg agaaggtttt    2460
gggacgctcg aaggctttaa tttgcgtgac ataactaatt acatgacttg actgattttt    2520
cc                                                                    2522

<210> SEQ ID NO 8
<211> LENGTH: 3887
<212> TYPE: DNA
<213> ORGANISM: Artificial Sequence
<220> FEATURE:
<223> OTHER INFORMATION: Codon optimized

<400> SEQUENCE: 8
aggaaacgaa gataaatctc gagtttatca ttatcaatac tgccatttca aagaatacgt      60
aaataattaa tagtagtgat tttcctaact ttatttagtc aaaaaattag ccttttaatt     120
ctgctgtaac ccgtacatgc caaaataggg ggcgggttac acagaatata taacactgat     180
ggtgctgggt tgaacaggtt tattcctggc atccactaaa tataatggag cccgcttttt     240
aagctggcat ccagaaaaaa aaagaatccc agcaccaaaa tattgttttc ttcaccaacc     300
atcagttcat aggtccattc tcttagcgca actacagaga cagggcaca aacaggcaaa     360 aaacgggcac aacctcaatg gagtgatgca acctgcctgg agtaaatgat gacacaaggc     420
aattgaccca cgcatgtatc tatctcattt tcttacacct tctattacct tctgctctct     480
ctgatttgga aaaagctgaa aaaaaaggtt taaaccagtt ccctgaaatt attcccctac     540
ttgactaata agtatataaa gacggtaggt attgattgta attctgtaaa tctatttctt     600
aaacttctta aattctactt ttatagttag tctttttttt agttttaaaa caccaagaac     660
ttagtttcga cggatctaga actagtatgg gtttatcatc cgtctgtact ttctccttcc     720
aaactaacta tcataccttta ttgaatcctc acaacaacaa tccaaaaaca tcattgttgt     780
```

```
gttacagaca tccaaagaca cctattaagt actcttacaa caactttcca tcaaaacatt    840
gttcaaccaa gtccttccac ttacaaaata agtgctccga aagtttgtct atagctaaga    900
actctatcag agctgcaact acaaatcaaa ctgaaccacc tgaaagtgat aatcactctg    960
ttgccacaaa aattttgaac ttcggtaaag catgttggaa gttgcaaaga ccatacacca   1020
taatcgcttt tacttcttgt gcatgcggtt tattcggtaa agaattgttg cataacacta   1080
acttaatttc atggtccttg atgttcaagg cattttttctt tttagttgcc atcttgtgca   1140
tcgcttcatt caccactaca attaatcaaa tatacgattt gcacatcgac agaattaaca   1200
aaccagattt gccttttggct tcaggtgaaa tatccgtcaa tactgcatgg atcatgtcta   1260
tcatagtagc cttgttcggt ttgatcatca caattaaaat gaagggtggt ccattgtaca   1320
tcttcggtta ctgtttcggt atcttcggtg gtattgtcta ttccgtacca ccttttagat   1380
ggaaacaaaa ccctagtact gccttttttgt tgaatttctt agctcatatc atcacaaact   1440
tcaccttcta ctacgcttca agagctgctt taggtttgcc attcgaattg agaccttcat   1500 tcacatttttt gttggcattc atgaaaagta tgggttctgc attagccttg atcaaggatg   1560
cctctgacgt tgaaggtgac acaaagttcg gtattagtac cttggcttct aagtacggtt   1620
caagaaattt gactttgttc tgctccggta tcgttttgtt aagttacgtc gcagccattt   1680
tggcaggtat catttggcca caagccttta attctaacgt tatgttgttg tcacatgcca   1740
tcttggcttt ctggttgatc ttgcaaacta gagatttcgc tttgacaaat tatgaccctg   1800
aagcaggtag aagattctac gagtttatgt ggaaattgta ctacgctgaa tatttggtat   1860
acgtttttat tgaaggtaga ggttcttttgt tgacctgtgg tgacgttgaa gaaaatccag   1920
gtcctatgaa atgttcaact ttctcctttt ggttcgtatg caagatcatc ttcttttttct   1980 tttcctttaa catccaaaca agtatcgcaa acccaagaga aaacttttttg aagtgcttct   2040 cacaatacat acctaataac gccaccaatt tgaagttggt ttacactcaa aacaacccat   2100
tgtacatgtc cgtcttgaac agtacaatcc ataatttgag attcacttct gataccactc   2160
caaaaccttt ggtcattgta acccctagtc atgtatctca catccaaggt actatcttat   2220
gttctaaaaa ggttggtttg caaattagaa ctagatccgg tggtcatgat agtgaaggca   2280
tgtcatacat ctcccaagtt ccattcgtta tcgttgattt gagaaacatg agatcaatta   2340
aaatagacgt acactcacaa actgcttggg ttgaagctgg tgcaacattg ggtgaagtat   2400
actactgggt taacgaaaag aatgaaaact tatcattggc tgctggttac tgtccaacag   2460
tttgcgcagg tggtcatttt ggtggtggtg gttatggtcc tttaatgaga aactacggtt   2520
tggccgctga taacataatc gacgctcatt tggtaaatgt tcacggtaaa gttttggata   2580
gaaagtctat gggtgaagac ttattttggg ctttgagagg tggtggtgca gaatcattcg   2640
gtatcatagt tgcttggaag ataagattag tcgcagtacc aaagtctact atgttctcag   2700
tcaaaaagat aatggaaatc catgaattag ttaaattggt caataagtgg caaaacatcg   2760
catacaagta cgataaggac ttgttgttga tgactcattt catcacaaga aacatcaccg   2820
ataaccaagg taaaaataag actgctatcc acacatactt tcttcagtt ttcttgggtg   2880 gtgtcgattc cttagtagac ttgatgaata agtctttttcc agaattaggt attaagaaaa   2940
ctgattgtag acaattgtct tggatcgaca ccatcatctt ttattcaggt gttgtcaact   3000
acgatacaga caacttcaac aaagaaatat tattggatag atccgcaggt caaaacggtg   3060
cctttaaaat taagttagac tacgttaaaa agccaatacc tgaatcagtt ttcgtccaaa   3120
tcttagaaaa attgtacgaa gaagatattg gtgcaggcat gtacgccttg tatccatacg   3180
```

```
gtggtataat ggacgaaatc agtgaatctg ccattccatt tcctcataga gctggtatct   3240
tatacgaatt gtggtacatt tgttcatggg aaaagcaaga agataacgaa aagcacttaa   3300
actggattag aaacatctat aacttcatga ctccatacgt ttctaaaaac cctagattgg   3360
catatttgaa ctacagagat ttggacatcg gtattaacga tccaaagaat cctaacaact   3420
atacccaagc tagaatttgg ggtgaaaaat acttcggtaa aaatttcgat agattagtaa   3480
aggttaagac attggttgac ccaaacaact tctttagaaa cgaacaatcc attccacctt   3540
tacctagaca tagacacgaa caaaaattaa taagtgaaga gatttgtaa gtcgacctcg   3600 agtcatgtaa ttagttatgt cacgcttaca ttcacgccct cccccacat ccgctctaac    3660 cgaaaaggaa ggagttagac aacctgaagt ctaggtccct atttattttt ttatagttat   3720
gttagtatta agaacgttat ttatatttca aattttctt tttttctgt acagacgcgt    3780 gtacgcatgt aacattatac tgaaaacctt gcttgagaag gttttgggac gctcgaaggc   3840
tttaatttgc gtgacataac taattacatg acttgactga ttttcc                 3887

<210> SEQ ID NO 9
<211> LENGTH: 8963
<212> TYPE: DNA
<213> ORGANISM: Artificial Sequence
<220> FEATURE:
<223> OTHER INFORMATION: Codon optimized

<400> SEQUENCE: 9
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataaacg acattactat atatataata taggaagcat ttaatagaca gcatcgtaat    240
atatgtgtac tttgcagtta tgacgccaga tggcagtagt ggaagatatt ctttattgaa    300
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga agtttgcgg cttgcagagc acagaggccg    540
cagaatgtgc tctagattcc gatgctgact tgctgggtat tatatgtgtg cccaatagaa    600
agagaacaat tgacccggtt attgcaagga aatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggttttgc cagttattaa aagactcgta tttccaaaag    840
actgcaacat actactcagt gcagcttcac agaaacctca ttcgtttatt cccttgtttg    900
attcagaagc aggtgggaca ggtgaacttt ggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgtta aatcagctcat tttttaacca ataggccgaa   1320
```

```
atcggcaaaa tcccttataa atcaaaagaa tagaccgaga tagggttgag tgttgttcca    1380
gtttggaaca agagtccact attaaagaac gtggactcca acgtcaaagg gcgaaaaacc    1440
gtctatcagg gcgatggccc actacgtgaa ccatcaccct aatcaagttt tttggggtcg    1500
aggtgccgta aagcactaaa tcggaaccct aaagggagcc cccgatttag agcttgacgg    1560
ggaaagccgg cgaacgtggc gagaaaggaa gggaagaaag cgaaaggagc gggcgctagg    1620
gcgctggcaa gtgtagcggt cacgctgcgc gtaaccacca cacccgccgc gcttaatgcg    1680
ccgctacagg gcgcgtcgcg ccattcgcca ttcaggctgc gcaactgttg ggaagggcga    1740
tcggtgcggg cctcttcgct attacgccag ctggcgaaag ggggatgtgc tgcaaggcga    1800
ttaagttggg taacgccagg gttttcccag tcacgacgtt gtaaaacgac ggccagtgag    1860
cgcgcgtaat acgactcact atagggcgaa ttgggtaccg gccgcaaatt aaagccttcg    1920
agcgtcccaa aaccttctca agcaaggttt tcagtataat gttacatgcg tacacgcgtc    1980
tgtacagaaa aaaagaaaa atttgaaata taaataacgt tcttaatact aacataacta    2040
taaaaaaata aatagggacc tagacttcag gttgtctaac tccttccttt tcggttagag    2100
cggatgtggg gggagggcgt gaatgtaagc gtgacataac taattacatg actcgaggtc    2160
gacttacttg tcatcgtcat ctttgtagtc aatatcgtgg tctttatagt caccgtcatg    2220
atccttgtaa tcctttgatc tcttgtagac cttattcaag aaagctgtca aaacgtcggc    2280
tttaaaacct cttgattcat caacttgact aatctttgcc tttaagtctt tagcgatgga    2340
ttcttcgtat tcatggtaca attgttcaat cttcaaatca ttaaaatttt tcttacactt    2400
tgcttcagca actgagtcct ttttaccgta gttttcatcc aaagtctttc tttgttcggc    2460
agatgctaat tccaaagcct tgttaataac ccaactgcac ttattgtctt gaatatctgt    2520
accgatttta cctatttgtt ctggagtacc gaaacagtct aagtagtcat cttggatttg    2580
gaagtattca cccaaaggta tcaaaacatc tcttgcttgc ttcaagtctt tttcatcagt    2640
aataccagct acgtacatag ccaaggcgac tggcaaatag aaggagtaat aagcagtttc    2700
aaaggtgacg atgaatgaat gtttcttcaa ggaaaacttt gacaagtcaa ctttatcttc    2760
aggtgcagtt atcaaatcca tcaattgacc caattctgtt tggaaagtaa cttcgtggaa    2820
taattcggta atatcgatgt agtacttttc gtttctgaaa tgtgacttca acaatttata    2880
gatagcggct ccaacataa aagcatcatt tatggctatt tcaccaactt ctggaacttt    2940
gtaccagcat ggttgacctc ttcttgttat agacttatcc atcatgtcat cggcaaccaa    3000
aaagtatgct tgcaacaatt caatacacca acccaagata gcgaccttt cgtattcttc    3060 ttgacctaat tgttcaacgg ttttgttaga caagatagca taagtatcaa ctacactcaa    3120
acctctattc aatttaccac ctggagtatt gtagtttaaa gagtgagcat accaatcgca    3180
ggcttcttta ggcataccat aagctaacaa actagcgttc aattcttcaa ctaactttgg    3240
gaatacgttc aagaatcttt ctcttcttat ttccttttct gaagccatag gacctggatt    3300 tcttcaacg tcaccacatg ttaacaaaga acctctacct tcttcgaaat gactgaattg    3360
ttgtctcaaa actcttctca tgatcttgtt tgttgcagtt ctaggtaagg atgacaatgg    3420
gacaactcta gtaactttga ataatggtt caatttcttt tgcaaaccca agttaaagga    3480
taatctcaat tggttcaaat caatggttgt gtcgtttgaa tccttcaata cgaaaaatat    3540
gaccaattgt tctggaccac cacccaaagg tggaacacca atagcagtgg tttcaaaaac    3600
tctgtcatct acttcattac agactctttc gatttcgata gaactaattt tgataccacc    3660
gatgttcata gtgtcatcgg ctctaccgtg tgcatggtag taaccgttag aggtcaattc    3720
```

```
gaaaatgtca ccatgtcttc tcaatacttc accattcaag gttggcatac ccttgaaata   3780
gacatcgtga tgattaccgt ttaacaatgt ttttgaggca ccaaacataa caggacctaa   3840
tgccaattca ccgatacctg gcttatttt aggcattggg taaccgttct tatctaatat   3900
gtacaaggtg caacccatac attgggatga aaaagaactt aaagattgag cttgcaaaaa   3960
tgaaccagca gaaaaagcac caccgatttc tgtaccacca cacatttcta taactggctt   4020
gtagttagct ctacccatta accacaaata ttcgtctaca ttagaggctt caccggatga   4080
agaaaagcat cttatggtgg accaatcgta acctgaaaca caatttgtgg atttccatga   4140
tcttacaata gatggtacga cacccaacat tgtgaccttt gcatcttgaa caaatttagc   4200
gaaaccagag actaaaggac taccgttgta caaggcaata gatgcaccat ttaacaaact   4260
agcataaacc aaccaaggac ccatcatcca acccaaatta gttggccata ctataacgtc   4320 acctttcta atatccaaat gagaccaacc atcagcagca gccttcaatg gggtggcttg   4380
tgtccaagga attgcttttg gttcacctgt agtaccactg gagaataaga tgttagtata   4440
agcatcaaca ggttgttctc tggcagtaaa ctcgcagttt ttaaactcct tggctctttc   4500
taaaaagtaa tcccaagata tgtcaccatc tctcaattct gcaccaatgt tagaaccact   4560
acaagggata actattgcca ttggggatttt agcttcaact actcttgaat acaatggtat   4620 tctctttta cctctgatga tgtgatcttg tgtgaaaatt gccttagctt tggataatct   4680
caatctagtt gagatttcag gggcggaaaa tgaatctgct atagagacaa ctacgtaacc   4740
agccaatact atggccaaat atataacaac agcatcaaca tgcattggca tatcgatggc   4800
tattgcacaa cctttttcta aacccatttc ttccaatgca taaccaacca accaaactct   4860
ctttctcaat tgatctaatg tcaacttatt caaaggcaag tcatcgttac cctcgtctct   4920
ccaaacgatc atagtatcgt tcaatttctt attggagttt acgttcaagc aatttttagc   4980
tgagttcaag taaccaccag gtaaccattc agaaccacct gggttgttga tgtcatctct   5040
tctcaagata cattctgggt ccttagagaa actaattttc atttcatcca tcaatactgt   5100
tctccaatag acttcagggt ttctaacaga aaattcttgg aagtgagaaa agaagaaat   5160 tggatctttg tactttacac ccaaaaattc tttacctctc ttttccaaca aagcacccaa   5220
attagttgac ttgactttt cagggtctgg aatccaagca ggtggggctg gaccgaaatc   5280
cttgtagcaa ccataaaaca acatttggtg taaggagaaa ggcaaatctg gtgacaagat   5340
atggttagcg atgttgatcc aagtttgagg ggttgcagca ccataattac aaacgatttc   5400
tgccaatcta ccatgtaatg tttctgctac ttctgaggtg atacccaatg cgatgaaatc   5460
tgaggcaacg actgaatcca aggacttata gtttttaccc atactagttc tagatccgtc   5520
gaaactaagt tcttggtgtt ttaaaactaa aaaaagact aactataaaa gtagaattta   5580
agaagtttaa gaaatagatt tacagaatta caatcaatac ctaccgtctt tatatactta   5640
ttagtcaagt aggggaataa tttcagggaa ctggtttaaa cctttttttt cagcttttc   5700 caaatcagag agagcagaag gtaatagaag gtgtaagaaa atgagataga tacatgcgtg   5760
ggtcaattgc cttgtgtcat catttactcc aggcaggttg catcactcca ttgaggttgt   5820
gcccgttttt tgcctgtttg tgccctgttc tctgtagttg cgctaagaga atggacctat   5880
gaactgatgg ttggtgaaga aaacaatatt ttggtgctgg gattctttt ttttctggat   5940 gccagcttaa aaagcgggct ccattatatt tagtggatgc caggaataaa cctgttcacc   6000
caagcaccat cagtgttata tattctgtgt aacccgcccc ctattttggc atgtacgggt   6060
```

```
tacagcagaa ttaaaaggct aatttttga ctaaataaag ttaggaaaat cactactatt      6120
aattatttac gtattctttg aaatggcagt attgataatg ataaactcga gagctccagc      6180
ttttgttccc tttagtgagg gttaattgcg cgcttggcgt aatcatggtc atagctgttt      6240
cctgtgtgaa attgttatcc gctcacaatt ccacacaaca taggagccgg aagcataaag      6300
tgtaaagcct ggggtgccta atgagtgagg taactcacat taattgcgtt gcgctcactg      6360
cccgctttcc agtcgggaaa cctgtcgtgc cagctgcatt aatgaatcgg ccaacgcgcg      6420
gggagaggcg gtttgcgtat tgggcgctct tccgcttcct cgctcactga ctcgctgcgc      6480
tcggtcgttc ggctgcggcg agcggtatca gctcactcaa aggcggtaat acggttatcc      6540
acagaatcag gggataacgc aggaaagaac atgtgagcaa aaggccagca aaaggccagg      6600
aaccgtaaaa aggccgcgtt gctggcgttt ttccataggc tccgcccccc tgacgagcat      6660
cacaaaaatc gacgctcaag tcagaggtgg cgaaacccga caggactata aagataccag      6720
gcgtttcccc ctggaagctc cctcgtgcgc tctcctgttc cgaccctgcc gcttaccgga      6780
tacctgtccg cctttctccc ttcgggaagc gtggcgcttt ctcatagctc acgctgtagg      6840
tatctcagtt cggtgtaggt cgttcgctcc aagctgggct gtgtgcacga accccccgtt      6900
cagcccgacc gctgcgcctt atccggtaac tatcgtcttg agtccaaccc ggtaagacac      6960
gacttatcgc cactggcagc agccactggt aacaggatta gcagagcgag gtatgtaggc      7020
ggtgctacag agttcttgaa gtggtggcct aactacggct acactagaag gacagtattt      7080
ggtatctgcg ctctgctgaa gccagttacc ttcggaaaaa gagttggtag ctcttgatcc      7140
ggcaaacaaa ccaccgctgg tagcggtggt ttttttgttt gcaagcagca gattacgcgc      7200
agaaaaaaag gatctcaaga agatcctttg atcttttcta cggggtctga cgctcagtgg      7260
aacgaaaact cacgttaagg gattttggtc atgagattat caaaaaggat cttcacctag      7320
atccttttaa attaaaaatg aagttttaaa tcaatctaaa gtatatatga gtaaacttgg      7380
tctgacagtt accaatgctt aatcagtgag gcacctatct cagcgatctg tctatttcgt      7440
tcatccatag ttgcctgact ccccgtcgtg tagataacta cgatacggga gggcttacca      7500
tctggcccca gtgctgcaat gataccgcga gacccacgct caccggctcc agatttatca      7560
gcaataaacc agccagccgg aagggccgag cgcagaagtg gtcctgcaac tttatccgcc      7620
tccatccagt ctattaattg ttgccgggaa gctagagtaa gtagttcgcc agttaatagt      7680
ttgcgcaacg ttgttgccat tgctacaggc atcgtggtgt cacgctcgtc gtttggtatg      7740
gcttcattca gctccggttc ccaacgatca aggcgagtta catgatcccc catgttgtgc      7800
aaaaaagcgg ttagctcctt cggtcctccg atcgttgtca agtaagtt ggccgcagtg      7860 ttatcactca tggttatggc agcactgcat aattctctta ctgtcatgcc atccgtaaga      7920
tgcttttctg tgactggtga gtactcaacc aagtcattct gagaatagtg tatgcggcga      7980
ccgagttgct cttgcccggc gtcaatacgg gataataccg cgccacatag cagaacttta      8040
aaagtgctca tcattggaaa acgttcttcg ggcgaaaac tctcaaggat cttaccgctg      8100
ttgagatcca gttcgatgta acccactcgt gcacccaact gatcttcagc atcttttact      8160
ttcaccagcg tttctgggtg agcaaaaaca ggaaggcaaa atgccgcaaa aaagggaata      8220
agggcgacac ggaaatgttg aatactcata ctcttccttt tcaatatta ttgaagcatt      8280 tatcagggtt attgtctcat gagcggatac atatttgaat gtatttagaa aaataaacaa      8340
ataggggttc cgcgcacatt tccccgaaaa gtgccacctg ggtccttttc atcacgtgct      8400
ataaaaataa ttataattta aatttttaa tataaatata taaattaaaa atagaaagta      8460
```

```
aaaaaagaaa ttaaagaaaa aatagttttt gttttccgaa gatgtaaaag actctagggg      8520
gatcgccaac aaatactacc ttttatcttg ctcttcctgc tctcaggtat taatgccgaa      8580
ttgtttcatc ttgtctgtgt agaagaccac acacgaaaat cctgtgattt tacattttac      8640
ttatcgttaa tcgaatgtat atctatttaa tctgcttttc ttgtctaata aatatatatg      8700
taaagtacgc ttttttgttga aattttttaa accttttgttt attttttttt cttcattccg    8760
taactcttct accttcttta tttactttct aaaatccaaa tacaaaacat aaaaataaat      8820
aaacacagag taaattccca aattattcca tcattaaaag atacgaggcg cgtgtaagtt      8880
acaggcaagc gatccgtcct aagaaaccat tattatcatg acattaacct ataaaaatag      8940
gcgtatcacg aggccctttc gtc                                             8963

<210> SEQ ID NO 10
<211> LENGTH: 7163
<212> TYPE: DNA
<213> ORGANISM: Artificial Sequence
<220> FEATURE:
<223> OTHER INFORMATION: Codon optimized

<400> SEQUENCE: 10
tcgcgcgttt cggtgatgac ggtgaaaacc tctgacacat gcagctcccg gagacggtca       60
cagcttgtct gtaagcggat gccgggagca gacaagcccg tcaggcgcg tcagcgggtg      120 ttggcgggtg tcgggctgg cttaactatg cggcatcaga gcagattgta ctgagagtgc      180
accataaacg acattactat atatataata taggaagcat ttaatagaca gcatcgtaat      240
atatgtgtac tttgcagtta tgacgccaga tggcagtagt ggaagatatt ctttattgaa      300
aaatagcttg tcaccttacg tacaatcttg atccggagct tttcttttt tgccgattaa      360 gaattaattc ggtcgaaaaa agaaaaggag agggccaaga ggggaggcat tggtgactat      420
tgagcacgtg agtatacgtg attaagcaca caaaggcagc ttggagtatg tctgttatta      480
atttcacagg tagttctggt ccattggtga agtttgcgg cttgcagagc acagaggccg      540
cagaatgtgc tctagattcc gatgctgact tgctgggtat tatatgtgtg cccaatagaa      600
agagaacaat tgacccggtt attgcaagga aaatttcaag tcttgtaaaa gcatataaaa      660
atagttcagg cactccgaaa tacttggttg gcgtgtttcg taatcaacct aaggaggatg      720
ttttggctct ggtcaatgat tacggcattg atatcgtcca actgcatgga gatgagtcgt      780
ggcaagaata ccaagagttc ctcggtttgc cagttattaa agactcgta tttccaaaag      840 actgcaacat actactcagt gcagcttcac agaaacctca ttcgtttatt cccttgtttg      900
attcagaagc aggtgggaca ggtgaacttt tggattggaa ctcgatttct gactgggttg      960
gaaggcaaga gagccccgaa agcttacatt ttatgttagc tggtggactg acgccagaaa     1020
atgttggtga tgcgcttaga ttaaatggcg ttattggtgt tgatgtaagc ggaggtgtgg     1080
agacaaatgt tgtaaaagac tctaacaaaa tagcaaattt cgtcaaaaat gctaagaaat     1140
aggttattac tgagtagtat ttatttaagt attgtttgtg cacttgccta tgcggtgtga     1200
aataccgcac agatgcgtaa ggagaaaata ccgcatcagg aaattgtaaa cgttaatatt     1260
ttgttaaaat tcgcgttaaa ttttttgttaa atcagctcat ttttttaacca ataggccgaa     1320 atcggcaaaa tcccttataa atcaaagaa tagaccgaga taggggttgag tgttgttcca     1380 gtttggaaca agagtccact attaaagaac gtggactcca acgtcaaagg gcgaaaaacc     1440
gtctatcagg gcgatggccc actacgtgaa ccatcaccct aatcaagttt tttggggtcg     1500
```

```
aggtgccgta aagcactaaa tcggaaccct aagggagcc ccgatttag agcttgacgg      1560 ggaaagccgg cgaacgtggc gagaaaggaa gggaagaaag cgaaaggagc gggcgctagg      1620
gcgctggcaa gtgtagcggt cacgctgcgc gtaaccacca cacccgccgc gcttaatgcg      1680
ccgctacagg gcgcgtcgcg ccattcgcca ttcaggctgc gcaactgttg ggaagggcga      1740
tcggtgcggg cctcttcgct attacgccag ctggcgaaag ggggatgtgc tgcaaggcga      1800
ttaagttggg taacgccagg gttttcccag tcacgacgtt gtaaaacgac ggccagtgag      1860
cgcgcgtaat acgactcact atagggcgaa ttgggtaccg gccgcaaatt aaagccttcg      1920
agcgtcccaa aaccttctca agcaaggttt tcagtataat gttacatgcg tacacgcgtc      1980
tgtacagaaa aaaagaaaa atttgaaata taaataacgt tcttaatact aacataacta      2040 taaaaaata aatagggacc tagacttcag gttgtctaac tccttccttt tcggttagag      2100
cggatgtggg gggagggcgt gaatgtaagc gtgacataac taattacatg actcgaggtc      2160
gacttatgca tagtctggaa catcgtaagg gtactttctt ggggtgtaat cgaagatcaa      2220
caatttttcc cagaaggatc tgtaaacgtc accaaaacca acgtgagctg gatgaatgat      2280
gtaatcttgg atagtttcaa ctgattcgaa ggttacttcg acaatgtgtg tataaccttc      2340
ttctttcttt tgtgtaacgt cttaccccca gtatacatct ttcatagcag gtataatgtt      2400
gaccaaatta acgtaggtct tgaaaaattc ttccttttga gcttctgtga tttcatcttt      2460
aaacttcaat actatcaaat gcttgacggc cataggacct gggttttctt caacgtcacc      2520
acaagttaac aaggaacctc taccttcata tttaattggt actgatctga caactactct      2580
ttcgacggtc aaaccaggac cgaaaccaaa taagacaccc cattcaaaac cgtcaccagt      2640
agtagattta ccctcttcta atgatctctt tctcaattca tccattacga acaagacagt      2700
ggatgaagac atgttaccgt gttcagataa aacatgtcta ctatctacaa acttttcttt      2760
cttcaaatcc aattttttctt caaccttatc caaaatggct ttaccacctg gatgtgttat      2820
ccagaaaata gagttccaat ctgagatacc tataggagtg aatgcttcta tcaaacactt      2880
ttctatgttg ttagagatta acattggaac gtctttgtgc aaatcgaaga tcaaacctgc      2940
ttctcttata tgaccaccaa ttgtaccttc agaattaggc aagatggttt gacctgtact      3000
gactaattca atattggtc tttcaccaac agattcgtca ggttctgcac caacaataac      3060
agcagcagca ccgtcaccga agatagcttg accaactaac aattccaagt cagaatcact      3120
tggacctcta aacaagcaag ccataatgtc gcaacaaaca gctaatactc tggcacccttt      3180 gttgttttct gcaatatcct tagcgattct caaaacagta ccaccaccgt agcaacctaa      3240
ttgatacatc atgactctct taacggatgg tgacaaacct aacaatttgg cacagtggta      3300
gtctgcacca ggcatatctg tagtagatgc acttgtaaaa atcaaatgag tgatctttga      3360
ctttggttga ccccattcct taatggcttt tgcacaagca tctttacccca atttaggaac      3420 ttcgacaact aacatgtctt gtctggcatc caatgtttgc atttcgtgtt ctaccaatct      3480
tggattttgc ttcaaatgtt cttcgttcaa gaagcagttt ctcttctga tcatagactt      3540 atcacatatt tttctaaact tttccttcaa ttgagtcatg tgttcactct tggtaactct      3600
gaagtaataa tcaggaaatt catcttggat caatatgttt tctgggttgg ctgtacctat      3660
ggctaatacg gaggcaggac cttcggctct caaatggttc atactagttc tagatccgtc      3720
gaaactaagt tcttggtgtt taaaactaa aaaaagact aactataaaa gtagaattta      3780
agaagtttaa gaaatagatt tacagaatta caatcaatac ctaccgtctt tatatactta      3840
ttagtcaagt aggggaataa tttcagggaa ctggtttaaa ccttttttttt cagcttttc      3900
```

```
caaatcagag agagcagaag gtaatagaag gtgtaagaaa atgagataga tacatgcgtg    3960
ggtcaattgc cttgtgtcat catttactcc aggcaggttg catcactcca ttgaggttgt    4020
gcccgttttt tgcctgtttg tgccctgttc tctgtagttg cgctaagaga atggacctat    4080
gaactgatgg ttggtgaaga aaacaatatt ttggtgctgg gattcttttt ttttctggat    4140
gccagcttaa aaagcgggct ccattatatt tagtggatgc caggaataaa cctgttcacc    4200
caagcaccat cagtgttata tattctgtgt aacccgcccc ctattttggc atgtacgggt    4260
tacagcagaa ttaaaaggct aattttttga ctaaataaag ttaggaaaat cactactatt    4320
aattatttac gtattctttg aaatggcagt attgataatg ataaactcga gagctccagc    4380
ttttgttccc tttagtgagg gttaattgcg cgcttggcgt aatcatggtc atagctgttt    4440
cctgtgtgaa attgttatcc gctcacaatt ccacacaaca taggagccgg aagcataaag    4500
tgtaaagcct ggggtgccta atgagtgagg taactcacat taattgcgtt gcgctcactg    4560
cccgctttcc agtcgggaaa cctgtcgtgc cagctgcatt aatgaatcgg ccaacgcgcg    4620
gggagaggcg gtttgcgtat tgggcgctct tccgcttcct cgctcactga ctcgctgcgc    4680
tcggtcgttc ggctgcggcg agcggtatca gctcactcaa aggcggtaat acggttatcc    4740
acagaatcag gggataacgc aggaaagaac atgtgagcaa aaggccagca aaaggccagg    4800
aaccgtaaaa aggccgcgtt gctggcgttt ttccataggc tccgcccccc tgacgagcat    4860
cacaaaaatc gacgctcaag tcagaggtgg cgaaacccga caggactata agataccag    4920 gcgtttcccc ctggaagctc cctcgtgcgc tctcctgttc cgaccctgcc gcttaccgga    4980
tacctgtccg cctttctccc ttcgggaagc gtggcgcttt ctcatagctc acgctgtagg    5040
tatctcagtt cggtgtaggt cgttcgctcc aagctgggct gtgtgcacga accccccgtt    5100
cagcccgacc gctgcgcctt atccggtaac tatcgtcttg agtccaaccc ggtaagacac    5160
gacttatcgc cactggcagc agccactggt aacaggatta gcagagcgag gtatgtaggc    5220
ggtgctacag agttcttgaa gtggtggcct aactacggct acactagaag gacagtattt    5280
ggtatctgcg ctctgctgaa gccagttacc ttcggaaaaa gagttggtag ctcttgatcc    5340
ggcaaacaaa ccaccgctgg tagcggtggt ttttttgttt gcaagcagca gattacgcgc    5400
agaaaaaaag gatctcaaga agatcctttg atcttttcta cggggtctga cgctcagtgg    5460
aacgaaaact cacgttaagg gattttggtc atgagattat caaaaaggat cttcacctag    5520
atccttttaa attaaaaatg aagttttaaa tcaatctaaa gtatatatga gtaaacttgg    5580
tctgacagtt accaatgctt aatcagtgag gcacctatct cagcgatctg tctatttcgt    5640
tcatccatag ttgcctgact ccccgtcgtg tagataacta cgatacggga gggcttacca    5700
tctggcccca gtgctgcaat gataccgcga gacccacgct caccggctcc agatttatca    5760
gcaataaacc agccagccgg aagggccgag cgcagaagtg gtcctgcaac tttatccgcc    5820
tccatccagt ctattaattg ttgccgggaa gctagagtaa gtagttcgcc agttaatagt    5880
ttgcgcaacg ttgttgccat tgctacaggc atcgtggtgt cacgctcgtc gtttggtatg    5940
gcttcattca gctccggttc ccaacgatca aggcgagtta catgatcccc catgttgtgc    6000
aaaaaagcgg ttagctcctt cggtcctccg atcgttgtca gaagtaagtt ggccgcagtg    6060
ttatcactca tggttatggc agcactgcat aattctctta ctgtcatgcc atccgtaaga    6120
tgcttttctg tgactggtga gtactcaacc aagtcattct gagaatagtg tatgcggcga    6180
ccgagttgct cttgcccggc gtcaatacgg gataataccg cgccacatag cagaacttta    6240
```

```
aaagtgctca tcattggaaa acgttcttcg gggcgaaaac tctcaaggat cttaccgctg    6300
ttgagatcca gttcgatgta acccactcgt gcacccaact gatcttcagc atcttttact    6360
ttcaccagcg tttctgggtg agcaaaaaca ggaaggcaaa atgccgcaaa aagggaata     6420 agggcgacac ggaaatgttg aatactcata ctcttccttt ttcaatatta ttgaagcatt    6480
tatcagggtt attgtctcat gagcggatac atatttgaat gtatttagaa aataaacaa     6540 ataggggttc cgcgcacatt tccccgaaaa gtgccacctg ggtcctttt catcacgtgct   6600 ataaaaataa ttataattta aattttttaa tataaatata taaattaaaa atagaaagta    6660
aaaaaagaaa ttaaagaaaa aatagttttt gttttccgaa gatgtaaaag actctagggg    6720
gatcgccaac aaatactacc ttttatcttg ctcttcctgc tctcaggtat taatgccgaa    6780
ttgtttcatc ttgtctgtgt agaagaccac acacgaaaat cctgtgattt tacattttac    6840
ttatcgttaa tcgaatgtat atctatttaa tctgcttttc ttgtctaata aatatatatg    6900
taaagtacgc ttttttgttga aatttttaa acctttgttt atttttttt cttcattccg     6960 taactcttct accttcttta tttactttct aaaatccaaa tacaaaacat aaaaataaat    7020
aaacacagag taaattccca aattattcca tcattaaaag atacgaggcg cgtgtaagtt    7080
acaggcaagc gatccgtcct aagaaaccat tattatcatg acattaaccc ataaaaatag    7140
gcgtatcacg aggccctttc gtc                                           7163

<210> SEQ ID NO 11
<211> LENGTH: 8710
<212> TYPE: DNA
<213> ORGANISM: Artificial Sequence
<220> FEATURE:
<223> OTHER INFORMATION: Codon optimized

<400> SEQUENCE: 11
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tctttttcta     300
ttactcttgg cctcctctag tacactctat atttttttat gcctcggtaa tgattttcat     360 ttttttttt cccctagcgg atgactcttt ttttttctta gcgattggca ttatcacata     420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tccctagcg atagagcact     600 cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctactg gcgcgtggag    840
taaaaaggtt tggatcagga tttgcgcctt ggatgaggc acttccaga gcggtggtag       900 atctttcgaa caggccgtac gcagttgtcg aacttggttt gcaagggag aaagtaggag     960 atctctcttg cgagatgatc ccgcattttc ttgaaagctt tgcagaggct agcagaatta    1020
ccctccacgt tgattgtctg cgaggcaaga atgatcatca ccgtagtgag agtgcgttca    1080
aggctcttgc ggttgccata agagaagcca cctcgcccaa tggtaccaac gatgttccct    1140
```

```
ccaccaaagg tgttcttatg tagtgacacc gattatttaa agctgcagca tacgatatat    1200
atacatgtgt atatatgtat acctatgaat gtcagtaagt atgtatacga acagtatgat    1260
actgaagatg acaaggtaat gcatcattct atacgtgtca ttctgaacga ggcgcgcttt    1320
cctttttcct ttttgctttt tctttttttt tctcttgaac tcgacggatc tatgcggtgt    1380
gaaataccgc acagatgcgt aaggagaaaa taccgcatca ggaaattgta acgttaata    1440 ttttgttaaa attcgcgtta aattttgtt aaatcagctc attttttaac caataggccg    1500
aaatcggcaa aatcccttat aaatcaaaag aatagaccga gatagggttg agtgttgttc    1560
cagtttggaa caagagtcca ctattaaaga acgtggactc caacgtcaaa gggcgaaaaa    1620
ccgtctatca gggcgatggc ccactacgtg aaccatcacc ctaatcaagt ttttgggt      1680 cgaggtgccg taaagcacta atcggaacc ctaaagggag ccccgattt agagcttgac     1740 ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
gatcggtgcg ggcctcttcg ctattacgcc agctggcgaa aggggatgt gctgcaaggc    1980 gattaagttg ggtaacgcca gggttttccc agtcacgacg ttgtaaaacg acggccagtg    2040
agcgcgcgta atacgactca ctatagggcg aattgggtac cggccgcaaa ttaaagcctt    2100
cgagcgtccc aaaaccttct caagcaaggt tttcagtata atgttacatg cgtacacgcg    2160
tctgtacaga aaaaaagaa aaatttgaaa tataaataac gttcttaata ctaacataac     2220
tataaaaaaa taaataggga cctagacttc aggttgtcta actccttcct tttcggttag    2280
agcggatgtg gggggagggc gtgaatgtaa gcgtgacata actaattaca tgactcgagg    2340
tcgacttaca aatcttcttc acttattaat ttttgttcgt gtctatgtct aggtaaaggt    2400
ggaatggatt gttcgtttct aaagaagttg tttgggtcaa ccaatgtctt aacctttact    2460
aatctatcga aattttttacc gaagtatttt tcacccaaa ttctagcttg ggtatagttg     2520
ttaggattct ttggatcgtt aataccgatg tccaaatctc tgtagttcaa atatgccaat    2580
ctagggtttt tagaaacgta tggagtcatg aagttataga tgtttctaat ccagtttaag    2640
tgcttttcgt tatcttcttg cttttcccat gaacaaatgt accacaattc gtataagata    2700
ccagctctat gaggaaatgg aatggcagat tcactgattt cgtccattat accaccgtat    2760
ggatacaagg cgtacatgcc tgcaccaata tcttcttcgt acaatttttc taagatttgg    2820
acgaaaactg attcaggtat tggcttttta acgtagtcta acttaatttt aaaggcaccg    2880
ttttgacctg cggatctatc caataatatt tctttgttga agttgtctgt atcgtagttg    2940
acaacacctg aataaaagat gatggtgtcg atccaagaca attgtctaca atcagttttc    3000
ttaataccta attctggaaa agacttattc atcaagtcta ctaaggaatc gacaccaccc    3060
aagaaaactg aagaaaagta tgtgtggata gcagtcttat ttttaccttg gttatcggtg    3120
atgtttcttg tgatgaaatg agtcatcaac aacaagtcct tatcgtactt gtatgcgatg    3180
ttttgccact tattgaccaa tttaactaat tcatggattt ccattatctt tttgactgag    3240
aacatagtag actttggtac tgcgactaat cttatcttcc aagcaactat gataccgaat    3300
gattctgcac caccacctct caaagcccaa aataagtctt cacccataga ctttctatcc    3360
aaaactttac cgtgaacatt taccaaatga gcgtcgatta tgttatcagc ggccaaaccg    3420
tagtttctca ttaaaggacc ataaccacca ccaccaaaat gaccacctgc gcaaactgtt    3480
```

```
ggacagtaac cagcagccaa tgataagttt tcattcttttt cgttaaccca gtagtatact    3540
tcacccaatg ttgcaccagc ttcaacccaa gcagtttgtg agtgtacgtc tattttaatt    3600
gatctcatgt ttctcaaatc aacgataacg aatggaactt gggagatgta tgacatgcct    3660
tcactatcat gaccaccgga tctagttcta atttgcaaac caaccttttt agaacataag    3720
atagtacctt ggatgtgaga tacatgacta ggggttacaa tgaccaaagg ttttggagtg    3780
gtatcagaag tgaatctcaa attatggatt gtactgttca agacggacat gtacaatggg    3840 ttgtttttgag tgtaaaccaa cttcaaattg gtggcgttat taggtatgta ttgtgagaag    3900
cacttcaaaa agttttctct tgggtttgcg atacttgttt ggatgttaaa ggaaaagaaa    3960
aagaagatga tcttgcatac gaaccaaaag gagaaagttg aacatttcat aggacctgga    4020
ttttcttcaa cgtcaccaca ggtcaacaaa gaacctctac cttcaataaa aacgtatacc    4080
aaatattcag cgtagtacaa tttccacata aactcgtaga atcttctacc tgcttcaggg    4140
tcataatttg tcaaagcgaa atctctagtt tgcaagatca accagaaagc caagatggca    4200
tgtgacaaca acataacgtt agaattaaag cttgtggcc aaatgatacc tgccaaaatg    4260
gctgcgacgt aacttaacaa aacgataccg gagcagaaca aagtcaaatt tcttgaaccg    4320
tacttagaag ccaaggtact aataccgaac tttgtgtcac cttcaacgtc agaggcatcc    4380
ttgatcaagg ctaatgcaga acccatactt ttcatgaatg ccaacaaaaa tgtgaatgaa    4440
ggtctcaatt cgaatggcaa acctaaagca gctcttgaag cgtagtagaa ggtgaagttt    4500
gtgatgatat gagctaagaa attcaacaaa aaggcagtac tagggttttg tttccatcta    4560
aaaggtggta cggaatagac aataccaccg aagataccga aacagtaacc gaagatgtac    4620
aatggaccac ccttcatttt aattgtgatg atcaaaccga acaaggctac tatgatagac    4680
atgatccatg cagtattgac ggatatttca cctgaagcca aaggcaaatc tggtttgtta    4740
attctgtcga tgtgcaaatc gtatatttga ttaattgtag tggtgaatga agcgatgcac    4800
aagatggcaa ctaaaaagaa aaatgccttg aacatcaagg accatgaaat taagttagtg    4860
ttatgcaaca attctttacc gaataaaccg catgcacaag aagtaaaagc gattatggtg    4920 tatggtctttt gcaacttcca acatgcttta ccgaagttca aaattttgt ggcaacagag    4980 tgattatcac tttcaggtgg ttcagtttga tttgtagttg cagctctgat agagttctta    5040
gctatagaca aactttcgga gcacttattt tgtaagtgga aggacttggt tgaacaatgt    5100
tttgatggaa agttgttgta agagtactta ataggtgtct ttggatgtct gtaacacaac    5160
aatgatgttt ttggattgtt gttgtgagga ttcaataagg tatgatagtt agtttggaag    5220
gagaaagtac agacggatga taaacccata ctagttctag atccgtcgaa actaagttct    5280
tggtgtttta aaactaaaaa aaagactaac tataaaagta gaatttaaga agtttaagaa    5340
atagatttac agaattacaa tcaataccta ccgtctttat atacttatta gtcaagtagg    5400
ggaataattt cagggaactg gtttaaacct ttttttttcag cttttttccaa atcagagaga    5460 gcagaaggta atagaaggtg taagaaaatg agatagatac atgcgtgggt caattgcctt    5520
gtgtcatcat ttactccagg caggttgcat cactccattg aggttgtgcc cgttttttgc    5580
ctgtttgtgc cctgttctct gtagttgcgc taagagaatg gacctatgaa ctgatggttg    5640
gtgaagaaaa caatatttg tgtgctgggat tctttttttt tctggatgcc agcttaaaaa    5700
gcgggctcca ttatatttag tggatgccag gaataaacct gttcacccaa gcaccatcag    5760
tgttatatat tctgtgtaac ccgcccccta ttttggcatg tacgggttac agcagaatta    5820
aaaggctaat ttttgacta aataaagtta ggaaaatcac tactattaat tatttacgta    5880
```

```
ttctttgaaa tggcagtatt gataatgata aactcgagag ctccagcttt tgttcccttt    5940
agtgagggtt aattgcgcgc ttggcgtaat catggtcata gctgtttcct gtgtgaaatt    6000
gttatccgct cacaattcca cacaacatag gagccggaag cataaagtgt aaagcctggg    6060
gtgcctaatg agtgaggtaa ctcacattaa ttgcgttgcg ctcactgccc gctttccagt    6120
cgggaaacct gtcgtgccag ctgcattaat gaatcggcca acgcgcgggg agaggcggtt    6180
tgcgtattgg gcgctcttcc gcttcctcgc tcactgactc gctgcgctcg tcgttcggc     6240
tgcggcgagc ggtatcagct cactcaaagg cggtaatacg ttatccaca gaatcagggg     6300
ataacgcagg aaagaacatg tgagcaaaag gccagcaaaa ggccaggaac cgtaaaaagg    6360
ccgcgttgct ggcgtttttc cataggctcc gcccccctga cgagcatcac aaaaatcgac    6420
gctcaagtca gaggtggcga aacccgacag gactataaag ataccaggcg tttcccctg     6480
gaagctccct cgtgcgctct cctgttccga ccctgccgct taccggatac ctgtccgcct    6540
ttctcccttc gggaagcgtg gcgctttctc atagctcacg ctgtaggtat ctcagttcgg    6600
tgtaggtcgt tcgctccaag ctgggctgtg tgcacgaacc ccccgttcag cccgaccgct    6660
gcgccttatc cggtaactat cgtcttgagt ccaacccggt aagacacgac ttatcgccac    6720
tggcagcagc cactggtaac aggattagca gagcgaggta tgtaggcggt gctacagagt    6780
tcttgaagtg gtggcctaac tacggctaca ctagaaggac agtatttggt atctgcgctc    6840
tgctgaagcc agttaccttc ggaaaaagag ttggtagctc ttgatccggc aaacaaacca    6900
ccgctggtag cggtggtttt tttgtttgca agcagcagat tacgcgcaga aaaaaggat     6960
ctcaagaaga tcctttgatc ttttctacgg ggtctgacgc tcagtggaac gaaaactcac    7020
gttaagggat tttggtcatg agattatcaa aaaggatctt cacctagatc ctttaaatt    7080
aaaaatgaag ttttaaatca atctaaagta tatatgagta aacttggtct gacagttacc    7140
aatgcttaat cagtgaggca cctatctcag cgatctgtct atttcgttca tccatagttg    7200
cctgactccc cgtcgtgtag ataactacga tacgggaggg cttaccatct ggccccagtg    7260
ctgcaatgat accgcgagac ccacgctcac cggctccaga tttatcagca ataaaccagc    7320
cagccggaag ggccgagcgc agaagtggtc ctgcaacttt atccgcctcc atccagtcta    7380
ttaattgttg ccgggaagct agagtaagta gttcgccagt taatagtttg cgcaacgttg    7440
ttgccattgc tacaggcatc gtggtgtcac gctcgtcgtt tggtatggct tcattcagct    7500
ccggttccca acgatcaagg cgagttacat gatcccccat gttgtgcaaa aaagcggtta    7560
gctccttcgg tcctccgatc gttgtcagaa gtaagttggc cgcagtgtta tcactcatgg    7620
ttatggcagc actgcataat tctcttactg tcatgccatc cgtaagatgc ttttctgtga    7680
ctggtgagta ctcaaccaag tcattctgag aatagtgtat gcggcgaccg agttgctctt    7740
gcccggcgtc aatacgggat aataccgcgc cacatagcag aactttaaaa gtgctcatca    7800
ttggaaaacg ttcttcgggg cgaaaactct caaggatctt accgctgttg agatccagtt    7860
cgatgtaacc cactcgtgca cccaactgat cttcagcatc ttttactttc accagcgttt    7920
ctgggtgagc aaaaacagga aggcaaaatg ccgcaaaaaa gggaataagg gcgacacgga    7980
aatgttgaat actcatactc ttcctttttc aatattattg aagcatttat cagggttatt    8040
gtctcatgag cggatacata tttgaatgta tttagaaaaa taaacaaata ggggttccgc    8100
gcacatttcc ccgaaaagtg ccacctgggt ccttttcatc acgtgctata aaaataatta    8160
taatttaaat tttttaatat aaatatataa attaaaaata gaaagtaaaa aagaaatta    8220
```

| aagaaaaaat agtttttgtt ttccgaagat gtaaaagact ctaggggat cgccaacaaa | 8280 |
| tactaccttt tatcttgctc ttcctgctct caggtattaa tgccgaattg tttcatcttg | 8340 |
| tctgtgtaga agaccacaca cgaaaatcct gtgatttta c attttactta tcgttaatcg | 8400 |
| aatgtatatc tatttaatct gcttttcttg tctaataaat atatatgtaa agtacgcttt | 8460 |
| ttgttgaaat tttttaaacc tttgtttatt ttttttttctt cattccgtaa ctcttctacc | 8520 |
| ttctttattt actttctaaa atccaaatac aaaacataaa aataaataaa cacagagtaa | 8580 |
| attcccaaat tattccatca ttaaaagata cgaggcgcgt gtaagttaca ggcaagcgat | 8640 |
| ccgtcctaag aaaccattat tatcatgaca ttaacctata aaaataggcg tatcacgagg | 8700 |
| cccttttcgtc | 8710 |

<210> SEQ ID NO 12
<211> LENGTH: 9617
<212> TYPE: DNA
<213> ORGANISM: Artificial Sequence
<220> FEATURE:
<223> OTHER INFORMATION: Codon optimized

<400> SEQUENCE: 12

| ttatcatgac attaacctat aaaaataggc gtatcacgag gccctttcgt ctcgcgcgtt | 60 |
| tcggtgatga cggtgaaaac ctctgacaca tgcagctccc ggagacggtc acagcttgtc | 120 |
| tgtaagcgga tgccgggagc agacaagccc gtcaggcgc gtcagcgggt gttggcgggt | 180 |
| gtcggggctg gcttaactat gcggcatcag agcagattgt actgagagtg caccacgctt | 240 |
| ttcaattcaa ttcatcattt tttttttatt cttttttttg atttcggttt ctttgaaatt | 300 |
| tttttgattc ggtaatctcc gaacagaagg aagaacgaag gaaggagcac agacttagat | 360 |
| tggtatatat acgcatatgt agtgttgaag aaacatgaaa ttgcccagta ttcttaaccc | 420 |
| aactgcacag aacaaaaacc tgcaggaaac gaagataaat catgtcgaaa gctacatata | 480 |
| aggaacgtgc tgctactcat cctagtcctg ttgctgccaa gctatttaat atcatgcacg | 540 |
| aaaagcaaac aaacttgtgt gcttcattgg atgttcgtac caccaaggaa ttactggagt | 600 |
| tagttgaagc attaggtccc aaaatttgtt tactaaaaac acatgtggat atcttgactg | 660 |
| atttttccat ggagggcaca gttaagccgc taaaggcatt atccgccaag tacaattttt | 720 |
| tactcttcga agacagaaaa tttgctgaca ttggtaatac agtcaaattg cagtactctg | 780 |
| cgggtgtata cagaatagca gaatgggcag acattacgaa tgcacacggt gtggtgggcc | 840 |
| caggtattgt tagcggtttg aagcaggcgg cagaagaagt aacaaaggaa cctagaggcc | 900 |
| ttttgatgtt agcagaattg tcatgcaagg ctccctatc tactggagaa atactaagg | 960 |
| gtactgttga cattgcgaag agcgacaaag attttgttat cggctttatt gctcaaagag | 1020 |
| acatgggtgg aagagatgaa ggttacgatt ggttgattat gacacccggt gtgggtttag | 1080 |
| atgacaaggg agacgcattg ggtcaacagt atagaaccgt ggatgatgtg gtctctacag | 1140 |
| gatctgacat tattattgtt ggaagaggac tatttgcaaa gggaaggat gctaaggtag | 1200 |
| agggtgaacg ttacagaaaa gcaggctggg aagcatattt gagaagatgc ggccagcaaa | 1260 |
| actaaaaaac tgtattataa gtaaatgcat gtatactaaa ctcacaaatt agagcttcaa | 1320 |
| tttaattata tcagttatta ccctgcggtg tgaaataccg cacagatgcg taaggagaaa | 1380 |
| ataccgcatc aggaaattgt aaacgttaat attttgttaa aattcgcgtt aaatttttgt | 1440 |
| taaatcagct catttttta ccaataggcc gaaatcggca aaatccctta taaatcaaaa | 1500 |
| gaatagaccg agataggtt gagtgttgtt ccagtttgga acaagagtcc actattaaag | 1560 |

```
aacgtggact ccaacgtcaa agggcgaaaa accgtctatc agggcgatgg cccactacgt   1620
gaaccatcac cctaatcaag ttttttgggg tcgaggtgcc gtaaagcact aaatcggaac   1680
cctaaaggga gcccccgatt tagagcttga cggggaaagc cggcgaacgt ggcgagaaag   1740
gaagggaaga aagcgaaagg agcgggcgct agggcgctgg caagtgtagc ggtcacgctg   1800
cgcgtaacca ccacacccgc cgcgcttaat gcgccgctac agggcgcgtc gcgccattcg   1860
ccattcaggc tgcgcaactg ttgggaaggg cgatcggtgc gggcctcttc gctattacgc   1920
cagctggcga agggggatg tgctgcaagg cgattaagtt gggtaacgcc agggttttcc    1980
cagtcacgac gttgtaaaac gacggccagt gaattgtaat acgactcact atagggcgaa   2040
ttggagctct agtacggatt agaagccgcc gagcgggcga cagccctccg acggaagact   2100
ctcctccgtg cgtcctcgtc ttcaccggtc gcgttcctga aacgcagatg tgcctcgcgc   2160
cgcactgctc cgaacaataa agattctaca atactagctt ttatggttat gaagaggaaa   2220
aattggcagt aacctggccc cacaaacctt caaattaacg aatcaaatta caaccatag    2280 gatgataatg cgattagttt tttagcctta tttctggggt aattaatcag cgaagcgatg   2340 attttgatc tattaacaga tatataaatg gaaaagctgc ataaccactt taactaatac    2400
tttcaacatt ttcagtttgt attacttctt attcaaatgt cataaaagta tcaacaaaaa   2460
attgttaata tacctctata ctttaacgtc aaggagaaaa aacccggat tctagaacta    2520 gtggatcccc catcatgaac catttgagag ccgaaggtcc tgcctccgta ttagccatag   2580
gtacagccaa cccagaaaac atattgatcc aagatgaatt tcctgattat tacttcagag   2640
ttaccaagag tgaacacatg actcaattga ggaaaagtt tagaaaaata tgtgataagt    2700
ctatgatcag aaagagaaac tgcttcttga acgaagaaca tttgaagcaa aatccaagat   2760
tggtagaaca cgaaatgcaa acattggatg ccagacaaga catgttagtt gtcgaagttc   2820
ctaaattggg taaagatgct tgtgcaaaag ccattaagga atgggtcaa ccaaagtcaa    2880 agatcactca tttgatttt acaagtgcat ctactacaga tatgcctggt gcagactacc    2940
actgtgccaa attgttaggt ttgtcaccat ccgttaagag agtcatgatg tatcaattag   3000
gttgctacgg tggtggtact gttttgagaa tcgctaagga tattgcagaa aacaacaagg   3060
gtgccagagt attagctgtt tgttgcgaca ttatggcttg cttgtttaga ggtccaagtg   3120
attctgactt ggaattgtta gttggtcaag ctatcttcgg tgacggtgct gctgctgtta   3180
ttgttggtgc agaacctgac gaatctgttg gtgaaagacc aatatttgaa ttagtcagta   3240
caggtcaaac catcttgcct aattctgaag gtacaattgg tggtcatata agagaagcag   3300
gtttgatctt cgatttgcac aaagacgttc caatgttaat ctctaacaac atagaaaagt   3360
gtttgataga agcattcact cctataggta tctcagattg gaactctatt ttctggataa   3420
cacatccagg tggtaaagcc attttggata aggttgaaga aaaattggat ttgaagaaag   3480
aaaagtttgt agatagtaga catgttttat ctgaacacgg taacatgtct tcatccactg   3540
tcttgttcgt aatggatgaa ttgagaaaga gatcattaga agagggtaaa tctactactg   3600
gtgacggttt tgaatggggt gtcttatttg gtttcggtcc tggtttgacc gtcgaaagag   3660
tagttgtcag atcagtacca attaaatatg aaggtagagg ttccttgtta acttgtggtg   3720
acgttgaaga aaacccaggt cctatggccg tcaagcattt gatagtattg aagtttaaag   3780
atgaaatcac agaagctcaa aaggaagaat ttttcaagac ctacgttaat ttggtcaaca   3840
ttatacctgc tatgaaagat gtatactggg gtaaagacgt tacacaaaag aaagaagaag   3900
```

```
gttatacaca cattgtcgaa gtaaccttcg aatcagttga aactatccaa gattacatca    3960
ttcatccagc tcacgttggt tttggtgacg tttacagatc cttctgggaa aaattgttga    4020
tcttcgatta caccccaaga aagttaaagc caaaataatg ataacgagaa taatatcaag    4080
aataccttag aacaacatcg acaacaacaa caggcatttt cggatatgag tcacgtggag    4140
tattccagaa ttacaaaatt ttttcaagaa caaccactgg agggatatac ccttttctct    4200
cacaggtctg cgccatgggt ttatcatccg tctgtacttt ctccttccaa actaactatc    4260
ataccttatt gaatcctcac aacaacaatc caaaacatc attgttgtgt tacagacatc     4320
caaagacacc tattaagtac tcttacaaca actttccatc aaaacattgt tcaaccaagt    4380
ccttccactt acaaaataag tgctccgaaa gtttgtctat agctaagaac tctatcagag    4440
ctgcaactac aaatcaaact gaaccacctg aaagtgataa tcactctgtt gccacaaaaa    4500
ttttgaactt cggtaaagca tgttggaagt tgcaaagacc atacaccata atcgctttta    4560
cttcttgtgc atgcggttta ttcggtaaag aattgttgca taacactaac ttaatttcat    4620
ggtccttgat gttcaaggca ttttttctttt tagttgccat cttgtgcatc gcttcattca    4680
ccactacaat taatcaaata tacgatttgc acatcgacag aattaacaaa ccagatttgc    4740
ctttggcttc aggtgaaata tccgtcaata ctgcatggat catgtctatc atagtagcct    4800
tgttcggttt gatcatcaca attaaaatga agggtggtcc attgtacatc ttcggttact    4860
gtttcggtat cttcggtggt attgtctatt ccgtaccacc ttttagatgg aaacaaaacc    4920
ctagtactgc cttttttgttg aatttcttag ctcatatcat cacaaacttc accttctact    4980
acgcttcaag agctgcttta ggtttgccat tcgaattgag accttcattc acatttttgt    5040
tggcattcat gaaaagtatg ggttctgcat tagccttgat caaggatgcc tctgacgttg    5100
aaggtgacac aaagttcggt attagtacct tggcttctaa gtacggttca agaaatttga    5160
cttttgtctg ctccggtatc gttttgttaa gttacgtcgc agccattttg gcaggtatca    5220
tttggccaca agcctttaat tctaacgtta tgttgttgtc acatgccatc ttggctttct    5280
ggttgatctt gcaaactaga gatttcgctt tgacaaatta tgaccctgaa gcaggtagaa    5340
gattctacga gtttatgtgg aaattgtact acgctgaata tttggtatac gttttttattg   5400 aaggtagagg ttctttgttg acctgtggtg acgttgaaga aaatccaggt cctatgaaat    5460
gttcaacttt ctccttttgg ttcgtatgca agatcatctt ctttttcttt tccttttaaca    5520 tccaaacaag tatcgcaaac ccaagagaaa acttttttgaa gtgcttctca caatacatac    5580
ctaataacgc caccaatttg aagttggttt cactcaaaa caacccattg tacatgtccg     5640
tcttgaacag tacaatccat aatttgagat tcacttctga taccactcca aaacctttgg    5700
tcattgtaac ccctagtcat gtatctcaca tccaaggtac tatcttatgt tctaaaaagg    5760
ttggtttgca aattagaact agatccggtg gtcatgatag tgaaggcatg tcatacatct    5820
cccaagttcc attcgttatc gttgatttga gaaacatgag atcaattaaa atagacgtac    5880
actcacaaac tgcttgggtt gaagctggtg caacattggg tgaagtatac tactgggtta    5940
acgaaaagaa tgaaaactta tcattggctg ctggttactg tccaacagtt tgcgcaggtg    6000
gtcattttgg tggtggtggt tatggtcctt aatgagaaa ctacggtttg gccgctgata     6060
acataatcga cgctcatttg gtaaatgttc acggtaaagt tttggataga aagtctatgg    6120
gtgaagactt attttgggct ttgagaggtg gtggtgcaga atcattcggt atcatagttg    6180
cttggaagat aagattagtc gcagtaccaa agtctactat gttctcagtc aaaaagataa    6240
tggaaatcca tgaattagtt aaattggtca ataagtggca aaacatcgca tacaagtacg    6300
```

```
ataaggactt gttgttgatg actcatttca tcacaagaaa catcaccgat aaccaaggta   6360
aaaataagac tgctatccac acatactttt cttcagtttt cttgggtggt gtcgattcct   6420
tagtagactt gatgaataag tcttttccag aattaggtat taagaaaact gattgtagac   6480
aattgtcttg gatcgacacc atcatctttt attcaggtgt tgtcaactac gatacagaca   6540
acttcaacaa agaaatatta ttggatagat ccgcaggtca aaacggtgcc tttaaaatta   6600
agttagacta cgttaaaaag ccaatacctg aatcagtttt cgtccaaatc ttagaaaaat   6660
tgtacgaaga agatattggt gcaggcatgt acgccttgta tccatacggt ggtataatgg   6720
acgaaatcag tgaatctgcc attccatttc ctcatagagc tggtatctta tacgaattgt   6780
ggtacatttg ttcatgggaa aagcaagaag ataacgaaaa gcacttaaac tggattagaa   6840
acatctataa cttcatgact ccatacgttt ctaaaaaccc tagattggca tatttgaact   6900
acagagattt ggacatcggt attaacgatc caaagaatcc taacaactat acccaagcta   6960
gaatttgggg tgaaaaatac ttcggtaaaa atttcgatag attagtaaag gttaagacat   7020
tggttgaccc aaacaacttc tttagaaacg aacaatccat tccacctttta cctagacata   7080 gacactgatg ggctgcagga attcgatatc aagcttatcg ataccgtcga cctcgagtca   7140
tgtaattagt tatgtcacgc ttacattcac gccctccccc cacatccgct ctaaccgaaa   7200
aggaaggagt tagacaacct gaagtctagg tccctattta ttttttttata gttatgttag   7260 tattaagaac gttatttata tttcaaattt ttctttttttt tctgtacaga cgcgtgtacg   7320
catgtaacat tatactgaaa accttgcttg agaaggtttt gggacgctcg aaggctttaa   7380
tttgcggccg gtacccagct tttgttccct ttagtgaggg ttaattccga gcttggcgta   7440
atcatggtca tagctgtttc ctgtgtgaaa ttgttatccg ctcacaattc cacacaacat   7500
aggagccgga agcataaagt gtaaagcctg gggtgcctaa tgagtgaggt aactcacatt   7560
aattgcgttg cgctcactgc ccgctttcca gtcgggaaac ctgtcgtgcc agctgcatta   7620
atgaatcggc caacgcgcgg ggagaggcgg tttgcgtatt gggcgctctt ccgcttcctc   7680
gctcactgac tcgctgcgct cggtcgttcg gctgcggcga gcggtatcag ctcactcaaa   7740
ggcggtaata cggttatcca cagaatcagg ggataacgca ggaaagaaca tgtgagcaaa   7800
aggccagcaa aaggccagga accgtaaaaa ggccgcgttg ctggcgtttt tccataggct   7860 cggccccccct gacgagcatc acaaaaatcg acgctcaagt cagaggtggc gaaacccgac   7920
aggactataa agataccagg cgttccccccc tggaagctcc ctcgtgcgct ctcctgttcc   7980
gaccctgccg cttaccggat acctgtccgc ctttctccct tcgggaagcg tggcgctttc   8040
tcaatgctca cgctgtaggt atctcagttc ggtgtaggtc gttcgctcca agctgggctg   8100
tgtgcacgaa ccccccgttc agcccgaccg ctgcgcctta tccggtaact atcgtcttga   8160
gtccaacccg gtaagacacg acttatcgcc actggcagca gccactggta acaggattag   8220
cagagcgagg tatgtaggcg gtgctacaga gttcttgaag tggtggccta actacggcta   8280
cactagaagg acagtatttg gtatctgcgc tctgctgaag ccagttacct tcggaaaaag   8340
agttggtagc tcttgatccg gcaaacaaac caccgctggt agcggtggtt ttttttgtttg   8400 caagcagcag attacgcgca gaaaaaaagg atctcaagaa gatcctttga tcttttctac   8460
ggggtctgac gctcagtgga acgaaaactc acgttaaggg attttggtca tgagattatc   8520
aaaaaggatc ttcacctaga tccttttaaa ttaaaaatga agttttaaat caatctaaag   8580
tatatatgag taaacttggt ctgacagtta ccaatgctta atcagtgagg cacctatctc   8640
```

-continued

| | |
|---|---|
| agcgatctgt ctatttcgtt catccatagt tgcctgactg cccgtcgtgt agataactac | 8700 |
| gatacgggag ggcttaccat ctggcccag tgctgcaatg ataccgcgag acccacgctc | 8760 |
| accggctcca gatttatcag caataaacca gccagccgga agggccgagc gcagaagtgg | 8820 |
| tcctgcaact ttatccgcct ccatccagtc tattaattgt tgccgggaag ctagagtaag | 8880 |
| tagttcgcca gttaatagtt tgcgcaacgt tgttgccatt gctacaggca tcgtggtgtc | 8940 |
| acgctcgtcg tttggtatgg cttcattcag ctccggttcc caacgatcaa ggcgagttac | 9000 |
| atgatccccc atgttgtgaa aaaagcggtt agctccttc ggtcctccga tcgttgtcag | 9060 |
| aagtaagttg gccgcagtgt tatcactcat ggttatggca gcactgcata attctcttac | 9120 |
| tgtcatgcca tccgtaagat gcttttctgt gactggtgag tactcaacca agtcattctg | 9180 |
| agaatagtgt atgcggcgac cgagttgctc ttgcccggcg tcaatacggg ataataccgc | 9240 |
| gccacatagc agaactttaa aagtgctcat cattggaaaa cgttcttcgg ggcgaaaact | 9300 |
| ctcaaggatc ttaccgctgt tgagatccag ttcgatgtaa cccactcgtg cacccaactg | 9360 |
| atcttcagca tcttttactt tcaccagcgt ttctgggtga gcaaaaacag gaaggcaaaa | 9420 |
| tgccgcaaaa aagggaataa gggcgacacg gaaatgttga atactcatac tcttcctttt | 9480 |
| tcaatattat tgaagcattt atcagggtta ttgtctcatg agcggataca tatttgaatg | 9540 |
| tatttagaaa aataaacaaa taggggttcc gcgcacattt ccccgaaaag tgccacctga | 9600 |
| cgtctaagaa accatta | 9617 |

<210> SEQ ID NO 13
<211> LENGTH: 7879
<212> TYPE: DNA
<213> ORGANISM: Artificial Sequence
<220> FEATURE:
<223> OTHER INFORMATION: Codon optimized

<400> SEQUENCE: 13

| | |
|---|---|
| aacctataaa aataggcgta tcacgaggcc ctttcgtctc gcgcgtttcg gtgatgacgg | 60 |
| tgaaaacctc tgacacatgc agctcccgga cggtcaca gcttgtctgt aagcggatgc | 120 |
| cgggagcaga caagcccgtc agggcgcgtc agcgggtgtt ggcgggtgtc ggggctggct | 180 |
| taactatgcg gcatcagagc agattgtact gagagtgcac cacgcttttc aattcaattc | 240 |
| atcattttt ttttattctt tttttgatt tcggtttctt tgaaattttt ttgattcggt | 300 |
| aatctccgaa cagaaggaag aacgaaggaa ggagcacaga cttagattgg tatatatacg | 360 |
| catatgtagt gttgaagaaa catgaaattg cccagtattc ttaacccaac tgcacagaac | 420 |
| aaaaacctgc aggaaacgaa gataaatcat gtcgaaagct acatataagg aacgtgctgc | 480 |
| tactcatcct agtcctgttg ctgccaagct atttaatatc atgcacgaaa agcaaacaaa | 540 |
| cttgtgtgct tcattggatg ttcgtaccac caaggaatta ctggagttag ttgaagcatt | 600 |
| aggtcccaaa atttgtttac taaaaacaca tgtggatatc ttgactgatt tttccatgga | 660 |
| gggcacagtt aagccgctaa aggcattatc cgccaagtac aattttttac tcttcgaaga | 720 |
| cagaaaattt gctgacattg gtaatacagt caaattgcag tactctgcgg gtgtatacag | 780 |
| aatagcagaa tgggcagaca ttacgaatgc acacggtgtg gtgggccag gtattgttag | 840 |
| cggtttgaag caggcggcag aagaagtaac aaaggaacct agaggccttt tgatgttagc | 900 |
| agaattgtca tgcaagggct ccctatctac tggagaatat actaagggta ctgttgacat | 960 |
| tgcgaagagc gacaaagatt ttgttatcgg ctttattgct caaagagaca tgggtggaag | 1020 |
| agatgaaggt tacgattggt tgattatgac acccggtgtg ggtttagatg acaagggaga | 1080 |

```
cgcattgggt caacagtata gaaccgtgga tgatgtggtc tctacaggat ctgacattat    1140
tattgttgga agaggactat ttgcaaaggg aagggatgct aaggtagagg gtgaacgtta    1200
cagaaaagca ggctgggaag catatttgag aagatgcggc cagcaaaact aaaaaactgt    1260
attataagta aatgcatgta tactaaactc acaaattaga gcttcaattt aattatatca    1320
gttattaccc tgcggtgtga aataccgcac agatgcgtaa ggagaaaata ccgcatcagg    1380
aaattgtaaa cgttaatatt ttgttaaaat tcgcgttaaa tttttgttaa atcagctcat    1440 ttttaacca ataggccgaa atcggcaaaa tcccttataa atcaaaagaa tagaccgaga    1500
tagggttgag tgttgttcca gtttggaaca agagtccact attaaagaac gtggactcca    1560
acgtcaaagg gcgaaaaacc gtctatcagg gcgatggccc actacgtgaa ccatcaccct    1620
aatcaagttt tttggggtcg aggtgccgta aagcactaaa tcggaaccct aaagggagcc    1680
cccgatttag agcttgacgg ggaaagccgg cgaacgtggc gagaaaggaa gggaagaaag    1740
cgaaaggagc gggcgctagg gcgctggcaa gtgtagcggt cacgctgcgc gtaaccacca    1800
cacccgccgc gcttaatgcg ccgctacagg gcgcgtcgcg ccattcgcca ttcaggctgc    1860
gcaactgttg ggaagggcga tcggtgcggg cctcttcgct attacgccag ctggcgaagg    1920
ggggatgtgc tgcaaggcga ttaagttggg taacgccagg gttttcccag tcacgacgtt    1980
gtaaaacgac ggccagtgaa ttgtaatacg actcactata gggcgaattg gagctctagt    2040
acggattaga agccgccgag cgggcgacag ccctccgacg gaagactctc ctccgtgcgt    2100
cctcgtcttc accggtcgcg ttcctgaaac gcagatgtgc ctcgcgccgc actgctccga    2160
acaataaaga ttctacaata ctagctttta tggttatgaa gaggaaaaat tggcagtaac    2220
ctggccccac aaaccttcaa attaacgaat caaattaaca accataggat gataatgcga    2280
ttagtttttt agccttattt ctggggtaat taatcagcga agcgatgatt tttgatctat    2340
taacagatat ataaatggaa aagctgcata accactttaa ctaatacttt caacattttc    2400
agtttgtatt acttcttatt caaatgtcat aaaagtatca acaaaaaatt gttaatatac    2460
ctctatactt taacgtcaag gagaaaaaac cccggattct agaactagtg gatcatgaac    2520
catttgagag ccgaaggtcc tgcctccgta ttagccatag gtacagccaa cccagaaaac    2580
atattgatcc aagatgaatt tcctgattat tacttcagag ttaccaagag tgaacacatg    2640
actcaattga aggaaaagtt tagaaaaata tgtgataagt ctatgatcag aaagagaaac    2700
tgcttcttga acgaagaaca tttgaagcaa aatccaagat tggtagaaca cgaaatgcaa    2760
acattggatg ccagacaaga catgttagtt gtcgaagttc ctaaattggg taaagatgct    2820
tgtgcaaaag ccattaagga atggggtcaa ccaaagtcaa agatcactca tttgattttt    2880
acaagtgcat ctactacaga tatgcctggt gcagactacc actgtgccaa attgttaggt    2940
ttgtcaccat ccgttaagag agtcatgatg tatcaattag gttgctacgg tggtggtact    3000
gttttgagaa tcgctaagga tattgcagaa aacaacaagg gtgccagagt attagctgtt    3060
tgttgcgaca ttatggcttg cttgtttaga ggtccaagtg attctgactt ggaattgtta    3120
gttggtcaag ctatcttcgg tgacggtgct gctgctgtta ttgttggtgc agaacctgac    3180
gaatctgttg gtgaaagacc aatatttgaa ttagtcagta caggtcaaac catcttgcct    3240
aattctgaag gtacaattgg tggtcatata agagaagcag gtttgatctt cgatttgcac    3300
aaagacgttc caatgttaat ctctaacaac atagaaagt gtttgataga agcattcact    3360
cctataggta tctcagattg gaactctatt ttctggataa cacatccagg tggtaaagcc    3420
```

```
attttggata aggttgaaga aaaattggat ttgaagaaag aaaagtttgt agatagtaga    3480
catgttttat ctgaacacgg taacatgtct catccactg tcttgttcgt aatggatgaa     3540
ttgagaaaga gatcattaga agagggtaaa tctactactg gtgacggttt tgaatggggt    3600
gtcttatttg gtttcggtcc tggtttgacc gtcgaaagag tagttgtcag atcagtacca    3660
attaaatatg aaggtagagg ttccttgtta acttgtggtg acgttgaaga aacccaggt     3720
cctatggccg tcaagcattt gatagtattg aagtttaaag atgaaatcac agaagctcaa    3780
aaggaagaat ttttcaagac ctacgttaat ttggtcaaca ttatacctgc tatgaaagat    3840
gtatactggg gtaaagacgt tacacaaaag aaagaagaag ttatacaca cattgtcgaa     3900
gtaaccttcg aatcagttga aactatccaa gattacatca ttcatccagc tcacgttggt    3960
tttggtgacg tttacagatc cttctgggaa aaattgttga tcttcgatta cacccccaaga   4020
aagtgataac gagaataata tcaagaatac cttagaacaa catcgacaac aacaacaggc    4080
attttcggat atgagtcacg tggagtattc cagaattaca aaattttttc aagaacaacc    4140
actggaggga tataccctt tctctcacag gtctgcgcca tgggtttatc atccgtctgt     4200
actttctcct tccaaactaa ctatcatacc ttattgaatc ctcacaacaa caatccaaaa    4260
acatcattgt tgtgttacag acatccaaag acacctatta agtactctta caacaacttt    4320
ccatcaaaac attgttcaac caagtccttc cacttacaaa ataagtgctc cgaaagtttg    4380
tctatagcta agaactctat cagagctgca actacaaatc aaactgaacc acctgaaagt    4440
gataatcact ctgttgccac aaaaattttg aacttcggta agcatgttg gaagttgcaa     4500
agaccataca ccataatcgc ttttacttct tgtgcatgcg ttttattcgg taagaattg     4560
ttgcataaca ctaacttaat ttcatggtcc ttgatgttca aggcattttt cttttttagtt   4620
gccatcttgt gcatcgcttc attcaccact acaattaatc aaatatacga tttgcacatc    4680
gacagaatta acaaaccaga tttgcctttg gcttcaggtg aaatatccgt caatactgca    4740
tggatcatgt ctatcatagt agccttgttc ggtttgatca tcacaattaa aatgaagggt    4800
ggtccattgt acatcttcgg ttactgtttc ggtatcttcg gtggtatgt ctattccgta     4860
ccaccttta gatggaaaca aaaccctagt actgccttt tgttgaatt cttagctcat       4920
atcatcacaa acttcacctt ctactacgct tcaagagctg ctttaggttt gccattcgaa    4980
ttgagacctt cattcacatt tttgttggca ttcatgaaaa gtatgggttc tgcattagcc    5040
ttgatcaagg atgcctctga cgttgaaggt gacacaaagt tcggtattag taccttggct    5100
tctaagtacg gttcaagaaa tttgactttg ttctgctccg gtatcgtttt gttaagttac    5160
gtcgcagcca ttttggcagg tatcatttgg ccacaagcct taattctaa cgttatgttg     5220
ttgtcacatg ccatcttggc ttttctggttg atcttgcaaa ctagagattt cgctttgaca   5280
aattatgacc ctgaagcagg tagaagattc tacgagttta tgtggaaatt gtactacgct    5340
gaatatttgg tatacgtttt tatttaacga taccgtcgac ctcgagtcat gtaattagtt    5400
atgtcacgct tacattcacg ccctcccccc acatccgctc taaccgaaaa ggaaggagtt    5460
agacaacctg aagtctaggt ccctatttat tttttatag ttatgttagt attaagaacg     5520
ttatttatat ttcaaatttt tctttttttt ctgtacagac gcgtgtacgc atgtaacatt    5580
atactgaaaa ccttgcttga aaggttttg ggacgctcga aggctttaat ttgcggccgg     5640
tacccagctt ttgttccctt tagtgagggt taattccgag cttggcgtaa tcatggtcat    5700
agctgtttcc tgtgtgaaat tgttatccgc tcacaattcc acacaacata ggagccggaa    5760
gcataaagtg taaagcctgg ggtgcctaat gagtgaggta actcacatta attgcgttgc    5820
```

```
gctcactgcc cgctttccag tcgggaaacc tgtcgtgcca gctgcattaa tgaatcggcc    5880
aacgcgcggg gagaggcggt ttgcgtattg ggcgctcttc cgcttcctcg ctcactgact    5940
cgctgcgctc ggtcgttcgg ctgcggcgag cggtatcagc tcactcaaag gcggtaatac    6000
ggttatccac agaatcaggg gataacgcag gaaagaacat gtgagcaaaa ggccagcaaa    6060
aggccaggaa ccgtaaaaag gccgcgttgc tggcgttttt ccataggctc ggcccccctg    6120
acgagcatca caaaaatcga cgctcaagtc agaggtggcg aaacccgaca ggactataaa    6180
gataccaggc gttccccct ggaagctccc tcgtgcgctc tcctgttccg accctgccgc    6240
ttaccggata cctgtccgcc tttctccctt cgggaagcgt ggcgctttct caatgctcac    6300
gctgtaggta tctcagttcg gtgtaggtcg ttcgctccaa gctgggctgt gtgcacgaac    6360
cccccgttca gcccgaccgc tgcgccttat ccggtaacta tcgtcttgag tccaacccgg    6420
taagacacga cttatcgcca ctggcagcag ccactggtaa caggattagc agagcgaggt    6480
atgtaggcgg tgctacagag ttcttgaagt ggtggcctaa ctacggctac actagaagga    6540
cagtatttgg tatctgcgct ctgctgaagc cagttacctt cggaaaaaga gttggtagct    6600
cttgatccgg caaacaaacc accgctggta gcggtggttt ttttgtttgc aagcagcaga    6660
ttacgcgcag aaaaaaagga tctcaagaag atcctttgat cttttctacg ggtctgacg    6720 ctcagtggaa cgaaaactca cgttaaggga ttttggtcat gagattatca aaaaggatct    6780
tcacctagat ccttttaaat taaaaatgaa gttttaaatc aatctaaagt atatatgagt    6840
aaacttggtc tgacagttac caatgcttaa tcagtgaggc acctatctca gcgatctgtc    6900
tatttcgttc atccatagtt gcctgactgc ccgtcgtgta gataactacg atacgggagg    6960
gcttaccatc tggccccagt gctgcaatga taccgcgaga cccacgctca ccggctccag    7020
atttatcagc aataaaccag ccagccggaa gggccgagcg cagaagtggt cctgcaactt    7080
tatccgcctc catccagtct attaattgtt gccgggaagc tagagtaagt agttcgccag    7140
ttaatagttt gcgcaacgtt gttgccattg ctacaggcat cgtggtgtca cgctcgtcgt    7200
ttggtatggc ttcattcagc tccggttccc aacgatcaag gcgagttaca tgatccccca    7260
tgttgtgaaa aaaagcggtt agctccttcg gtcctccgat cgttgtcaga agtaagttgg    7320
ccgcagtgtt atcactcatg gttatggcag cactgcataa ttctcttact gtcatgccat    7380
ccgtaagatg cttttctgtg actggtgagt actcaaccaa gtcattctga atagtgta     7440 tgcggcgacc gagttgctct tgcccggcgt caatacggga taataccgcg ccacatagca    7500
gaactttaaa agtgctcatc attggaaaac gttcttcggg gcgaaaactc tcaaggatct    7560
taccgctgtt gagatccagt tcgatgtaac ccactcgtgc acccaactga tcttcagcat    7620
cttttacttt caccagcgtt tctgggtgag caaaaacagg aaggcaaaat gccgcaaaaa    7680
agggaataag ggcgacacgg aaatgttgaa tactcatact cttcctttt caatattatt     7740 gaagcattta tcagggttat tgtctcatga gcggatacat atttgaatgt atttagaaaa    7800
ataaacaaat aggggttccg cgcacatttc cccgaaaagt gccacctgac gtctaagaaa    7860
ccattattat catgacatt                                                 7879
```

<210> SEQ ID NO 14
<211> LENGTH: 3353
<212> TYPE: DNA
<213> ORGANISM: Artificial Sequence
<220> FEATURE:
<223> OTHER INFORMATION: Codon optimized

<400> SEQUENCE: 14

```
actagtatgg gtaaaaacta taagtccttg gattcagtcg ttgcctcaga tttcatcgca      60
ttgggtatca cctcagaagt agcagaaaca ttacatggta gattggcaga atcgtttgt     120
aattatggtg ctgcaacccc tcaaacttgg atcaacatcg ctaaccatat cttgtcacca    180
gatttgcctt tctccttaca ccaaatgttg ttttatggtt gctacaagga tttcggtcca    240
gccccacctg cttggattcc agaccctgaa aaagtcaagt caactaattt gggtgctttg    300
ttggaaaaga gaggtaaaga attttttgggt gtaaagtaca aagatccaat ttcttctttt   360
tctcacttcc aagaattttc tgttagaaac cctgaagtct attggagaac agtattgatg    420
gatgaaatga aaattagttt ctctaaggac ccagaatgta tcttgagaag agatgacatc    480
aacaacccag gtggttctga atggttacct ggtggttact tgaactcagc taaaaattgc    540
ttgaacgtaa actccaataa gaaattgaac gatactatga tcgtttggag agacgagggt    600
aacgatgact tgcctttgaa taagttgaca ttagatcaat tgagaaagag agtttggttg    660
gttggttatg cattggaaga atgggtttta gaaaaaggtt gtgcaatagc catcgatatg    720
ccaatgcatg ttgatgctgt tgttatatat ttggccatag tattggctgg ttacgtagtt    780
gtctctatag cagattcatt ttccgcccct gaaatctcaa ctagattgag attatccaaa    840
gctaaggcaa ttttcacaca agatcacatc atcagaggta aaagagaat accattgtat    900
tcaagagtag ttgaagctaa atccccaatg gcaatagtta tcccttgtag tggttctaac    960
attggtgcag aattgagaga tggtgacata tcttgggatt actttttaga aagagccaag   1020
gagtttaaaa actgcgagtt tactgccaga gaacaacctg ttgatgctta tactaacatc   1080
ttattctcca gtggtactac aggtgaacca aaagcaattc cttggacaca agccaccccca  1140
ttgaaggctg ctgctgatgg ttggtctcat ttggatatta gaaaaggtga cgttatagta   1200
tggccaacta atttgggttg gatgatgggt ccttggttgg tttatgctag tttgttaaat   1260
ggtgcatcta ttgccttgta caacggtagt cctttagtct ctggtttcgc taaatttgtt   1320
caagatgcaa aggtcacaat gttgggtgtc gtaccatcta ttgtaagatc atggaaatcc   1380
acaaattgtg tttcaggtta cgattggtcc accataagat gcttttcttc atccggtgaa   1440
gcctctaatg tagacgaata tttgtggtta atgggtagag ctaactacaa gccagttata   1500
gaaatgtgtg gtggtacaga aatcggtggt gcttttttctg ctggttcatt tttgcaagct   1560
caatctttaa gttcttttttc atcccaatgt atgggttgca ccttgtacat attagataag   1620
aacggttacc caatgcctaa aaataagcca ggtatcggtg aattggcatt aggtcctgtt   1680
atgtttggtg cctcaaaaac attgttaaac ggtaatcatc acgatgtcta tttcaagggt   1740
atgccaacct tgaatggtga agtattgaga agacatggtg acattttcga attgaccctct   1800
aacggttact accatgcaca cggtagagcc gatgacacta tgaacatcgg tggtatcaaa   1860
attagttcta tcgaaatcga aagagtctgt aatgaagtag atgacagagt ttttgaaacc   1920
actgctattg gtgttccacc tttgggtggt ggtccagaac aattggtcat attttttcgta  1980
ttgaaggatt caaacgacac aaccattgat ttgaaccaat tgagattatc ctttaacttg   2040
ggtttgcaaa agaaattgaa cccattattc aaagttacta gagttgtccc attgtcatcc   2100
ttacctagaa ctgcaacaaa caagatcatg agaagagttt tgagacaaca attcagtcat   2160
ttcgaagaag gtagaggttc tttgttaaca tgtggtgacg ttgaagaaaa tccaggtcct   2220
atggcttcag aaaaggaaat aagaagagaa agattcttga acgtattccc aaagttagtt   2280
gaagaattga acgctagttt gttagcttat ggtatgccta agaagcctg cgattggtat    2340
```

```
gctcactctt taaactacaa tactccaggt ggtaaattga atagaggttt gagtgtagtt    2400
gatacttatg ctatcttgtc taacaaaacc gttgaacaat taggtcaaga agaatacgaa    2460
aaggtcgcta tcttggggttg gtgtattgaa ttgttgcaag catactttt ggttgccgat    2520 gacatgatgg ataagtctat aacaagaaga ggtcaaccat gctggtacaa agttccagaa    2580
gttggtgaaa tagccataaa tgatgctttt atgttggaag ccgctatcta taaattgttg    2640
aagtcacatt tcagaaacga aaagtactac atcgatatta ccgaattatt ccacgaagtt    2700
actttccaaa cagaattggg tcaattgatg gatttgataa ctgcacctga agataaagtt    2760
gacttgtcaa agttttcctt gaagaaacat tcattcatcg tcacctttga aactgcttat    2820
tactccttct atttgccagt cgccttggct atgtacgtag ctggtattac tgatgaaaaa    2880
gacttgaagc aagcaagaga tgttttgata cctttgggtg aatacttcca aatccaagat    2940
gactacttag actgtttcgg tactccagaa caaataggta aaatcggtac agatattcaa    3000
gacaataagt gcagttgggt tattaacaag gctttggaat tagcatctgc cgaacaaaga    3060
aagactttgg atgaaaacta cggtaaaaag gactcagttg ctgaagcaaa gtgtaagaaa    3120 attttaatg atttgaagat tgaacaattg taccatgaat acgaagaatc catcgctaaa    3180
gacttaaagg caaagattag tcaagttgat gaatcaagag gttttaaagc cgacgttttg    3240
acagctttct tgaataaggt ctacaagaga tcaaaggatt acaaggatca tgacggtgac    3300
tataaagacc acgatattga ctacaaagat gacgatgaca agtaagcggc cgc           3353

<210> SEQ ID NO 15
<211> LENGTH: 1553
<212> TYPE: DNA
<213> ORGANISM: Artificial Sequence
<220> FEATURE:
<223> OTHER INFORMATION: Codon optimized

<400> SEQUENCE: 15
actagtatga accatttgag agccgaaggt cctgcctccg tattagccat aggtacagcc      60
aacccagaaa acatattgat ccaagatgaa tttcctgatt attacttcag agttaccaag     120
agtgaacaca tgactcaatt gaaggaaaag tttagaaaaa tatgtgataa gtctatgatc     180
agaaagagaa actgcttctt gaacgaagaa catttgaagc aaaatccaag attggtagaa     240
cacgaaatgc aaacattgga tgccagacaa gacatgttag ttgtcgaagt tcctaaattg     300
ggtaaagatg cttgtgcaaa agccattaag gaatggggtc aaccaaagtc aaagatcact     360
catttgattt ttacaagtgc atctactaca gatatgcctg gtgcagacta ccactgtgcc     420
aaattgttag gtttgtcacc atccgttaag agagtcatga tgtatcaatt aggttgctac     480
ggtggtggta ctgttttgag aatcgctaag gatattgcag aaaacaacaa gggtgccaga     540
gtattagctg tttgttgcga cattatggct tgcttgttta gaggtccaag tgattctgac     600
ttggaattgt tagttggtca agctatcttc ggtgacggtg ctgctgctgt tattgttggt     660
gcagaacctg acgaatctgt tggtgaaaga ccaatatttg aattagtcag tacaggtcaa     720
accatcttgc ctaattctga aggtacaatt ggtggtcata taagagaagc aggtttgatc     780
ttcgatttgc acaaagacgt tccaatgtta atctctaaca catagaaaaa gtgttttgata     840 gaagcattca ctcctatagg tatctcagat tggaactcta ttttctggat aacacatcca     900
ggtggtaaag ccattttgga taaggttgaa gaaaaattgg atttgaagaa agaaaagttt     960
gtagatagta gacatgtttt atctgaacac ggtaacatgt cttcatccac tgtccttgttc    1020
```

```
gtaatggatg aattgagaaa gagatcatta aagagggta aatctactac tggtgacggt    1080
tttgaatggg gtgtcttatt tggtttcggt cctggtttga ccgtcgaaag agtagttgtc    1140
agatcagtac caattaaata tgaaggtaga ggttccttgt taacttgtgg tgacgttgaa    1200
gaaaacccag gtcctatggc cgtcaagcat tgatagtat tgaagtttaa agatgaaatc    1260
acagaagctc aaaaggaaga atttttcaag acctacgtta atttggtcaa cattatacct    1320
gctatgaaag atgtatactg gggtaaagac gttacacaaa agaaagaaga aggttataca    1380
cacattgtcg aagtaaccct cgaatcagtt gaaactatcc aagattacat cattcatcca    1440
gctcacgttg gttttggtga cgtttacaga tccttctggg aaaaattgtt gatcttcgat    1500
tacaccccaa gaaagtaccc ttacgatgtt ccagactatg cataagcggc cgc           1553

<210> SEQ ID NO 16
<211> LENGTH: 2918
<212> TYPE: DNA
<213> ORGANISM: Artificial Sequence
<220> FEATURE:
<223> OTHER INFORMATION: Codon optimized

<400> SEQUENCE: 16
actagtatgg gtttatcatc cgtctgtact ttctccttcc aaactaacta tcataccta     60 ttgaatcctc acaacaacaa tccaaaaaca tcattgttgt gttacagaca tccaaagaca    120
cctattaagt actcttacaa caactttcca tcaaaacatt gttcaaccaa gtccttccac    180
ttacaaaata gtgctccga aagtttgtct atagctaaga actctatcag agctgcaact    240
acaaatcaaa ctgaaccacc tgaaagtgat aatcactctg ttgccacaaa aattttgaac    300
ttcggtaaag catgttggaa gttgcaaaga ccatacacca taatcgcttt tacttcttgt    360
gcatgcggtt tattcggtaa agaattgttg cataacacta acttaatttc atggtccttg    420
atgttcaagg cattttttctt tttagttgcc atcttgtgca tcgcttcatt caccactaca    480
attaatcaaa tatacgattt gcacatcgac agaattaaca aaccagattt gcctttggct    540
tcaggtgaaa tatccgtcaa tactgcatgg atcatgtcta tcatagtagc cttgttcggt    600
ttgatcatca caattaaaat gaagggtggt ccattgtaca tcttcggtta ctgtttcggt    660
atcttcggtg gtattgtcta ttccgtacca ccttttagat ggaaacaaaa ccctagtact    720
gcctttttgt tgaatttctt agctcatatc atcacaaact tcaccttcta ctacgcttca    780
agagctgctt taggtttgcc attcgaattg agaccttcat tcacatttt gttggcattc    840 atgaaaagta tgggttctgc attagccttg atcaaggatg cctctgacgt tgaaggtgac    900
acaaagttcg gtattagtac cttggcttct aagtacggtt caagaaattt gactttgttc    960
tgctccggta tcgttttgtt aagttacgtc gcagccattt tggcaggtat catttggcca   1020
caagccttta attctaacgt tatgttgttg tcacatgcca tcttggcttt ctggttgatc   1080
ttgcaaacta gagatttcgc tttgacaaat tatgaccctg aagcaggtag aagattctac   1140
gagtttatgt ggaaattgta ctacgctgaa tatttggtat acgttttttat tgaaggtaga   1200 ggttctttgt tgacctgtgg tgacgttgaa gaaaatccag gtcctatgaa atgttcaact   1260
ttctcctttt ggttcgtatg caagatcatc ttcttttct tttcctttaa catccaaaca    1320
agtatcgcaa acccaagaga aaacttttg aagtgcttct cacaatacat acctaataac    1380
gccaccaatt tgaagttggt ttacactcaa acaacccat tgtacatgtc cgtcttgaac    1440
agtacaatcc ataatttgag attcacttct gataccactc caaaaccttt ggtcattgta   1500 accccctagtc atgtatctca catccaaggt actatcttat gttctaaaaa ggttggtttg    1560
```

-continued

```
caaattagaa ctagatccgg tggtcatgat agtgaaggca tgtcatacat ctcccaagtt      1620
ccattcgtta tcgttgattt gagaaacatg agatcaatta aaatagacgt acactcacaa      1680
actgcttggg ttgaagctgg tgcaacattg ggtgaagtat actactgggt taacgaaaag      1740
aatgaaaact tatcattggc tgctggttac tgtccaacag tttgcgcagg tggtcatttt      1800
ggtggtggtg gttatggtcc tttaatgaga aactacggtt tggccgctga taacataatc      1860
gacgctcatt tggtaaatgt tcacggtaaa gttttggata gaaagtctat gggtgaagac      1920
ttatttgggg ctttgagagg tggtggtgca gaatcattcg gtatcatagt tgcttggaag      1980
ataagattag tcgcagtacc aaagtctact atgttctcag tcaaaaagat aatggaaatc      2040
catgaattag ttaaattggt caataagtgg caaaacatcg catacaagta cgataaggac      2100
ttgttgttga tgactcattt catcacaaga aacatcaccg ataaccaagg taaaaataag      2160
actgctatcc acacatactt ttcttcagtt ttcttgggtg gtgtcgattc cttagtagac      2220
ttgatgaata agtcttttcc agaattaggt attaagaaaa ctgattgtag acaattgtct      2280
tggatcgaca ccatcatctt ttattcaggt gttgtcaact acgatacaga caacttcaac      2340
aaagaaatat tattggatag atccgcaggt caaaacggtg cctttaaaat taagttagac      2400
tacgttaaaa agccaatacc tgaatcagtt ttcgtccaaa tcttagaaaa attgtacgaa      2460
gaagatattg gtgcaggcat gtacgccttg tatccatacg tggtataat ggacgaaatc       2520 agtgaatctg ccattccatt tcctcataga gctggtatct tatacgaatt gtggtacatt      2580
tgttcatggg aaaagcaaga agataacgaa aagcacttaa actggattag aaacatctat      2640
aacttcatga ctccatacgt ttctaaaaac cctagattgg catatttgaa ctacagagat      2700
ttggacatcg gtattaacga tccaaagaat cctaacaact ataccaagc tagaatttgg       2760 ggtgaaaaat acttcggtaa aaatttcgat agattagtaa aggttaagac attggttgac      2820
ccaaacaact tctttagaaa cgaacaatcc attccacctt tacctagaca tagacacgaa      2880
caaaaattaa taagtgaaga agatttgtaa gcggccgc                              2918
```

<210> SEQ ID NO 17
<211> LENGTH: 167
<212> TYPE: DNA
<213> ORGANISM: Artificial Sequence
<220> FEATURE:
<223> OTHER INFORMATION: Codon optimized

<400> SEQUENCE: 17

```
agccaaaata atgataacga gaataatatc aagaatacct tagaacaaca tcgacaacaa       60
caacaggcat tttcggatat gagtcacgtg gagtattcca gaattacaaa attttttcaa      120
gaacaaccac tggagggata tacccttttc tctcacaggt ctgcgcc                    167
```

<210> SEQ ID NO 18
<211> LENGTH: 1518
<212> TYPE: DNA
<213> ORGANISM: Artificial Sequence
<220> FEATURE:
<223> OTHER INFORMATION: Codon optimized

<400> SEQUENCE: 18

```
atggtttcca atcacttgtt tgacgcaatg agagccgctg cccctggtaa cgccccttc       60 ataagaatag ataatactag aacttggaca tacgatgacg cctttgcttt atctggtaga     120
atagcatcag ctatggatgc tttgggtatc agaccaggtg acagagtcgc agttcaagta     180
```

```
gaaaaatccg ctgaagcatt gatcttgtat ttggcttgtt tgagaagtgg tgcagtttat      240
ttgccattga atactgccta cacattagct gaattggatt acttcatagg tgacgcagaa      300
cctagattgg ttgtagtcgc ctcttcagcc agagctggtg tagaaacaat tgctaaacca      360
agaggtgcaa tagtcgaaac cttagatgct gctggttctg gtagtttgtt agatttggcc      420
agagacgaac ctgctgattt tgttgacgct tcaagatcag ccgatgactt agccgctatt      480
ttgtacacct ctggtactac aggtagatca aagggtgcta tgttgactca tggtaatttg      540
ttgtcaaacg cattaacctt gagagatttc tggagagtta ctgccggtga cagattaatc      600
cacgctttgc caattttca tactcacggt ttattcgttg ctaccaacgt aactttgtta      660
gcaggtgcct ccatgttctt gttgagtaag ttcgatccag aagaaatatt atctttgatg      720
cctcaagcta ctatgttgat gggtgtccca acattctacg ttagattgtt acaatcacct      780
agattagata agcaagctgt tgcaaacatc agattgttta tatccggtag tgctccattg      840
ttagcagaaa cccatactga atttcaagca agaacaggtc acgccatttt agaaagatac      900
ggtatgacag aaaccaatat gaacacttct aacccttatg aaggtaaaag aatagctggt      960
acagttggtt ttccattgcc tgatgtcaca gttagagtaa ccgacccagc cactggttta     1020
gctttgccac ctgaacaaac tggtatgatc gaaattaaag gtccaaacgt ttttaagggt     1080
tactggagaa tgcctgaaaa gactgctgct gagtttactg ctgatggttt ctttatctct     1140
ggtgacttag gtaaaattga tagagacggt tatgtccata ttgttggtcg tggtaaagat     1200
ttggttatat ccggtggtta acatctac cctaaggaag tagaaggtga aatagatcaa     1260
atcgaaggtg ttgtagaatc agctgtaata ggtgtcccac atcctgattt tggtgaaggt     1320
gttacagcag tcgttgtaag aaaaccaggt gctgcattag atgaaaaggc aattgtttct     1380
gccttacaag acagattggc tagatacaag caaccaaaga gaataatctt cgcagaagat     1440
ttgcctagaa atactatggg taaagtacaa aagaacatct tgagacaaca atacgccgac     1500
ttatacacca gaacctga                                                   1518

<210> SEQ ID NO 19
<211> LENGTH: 2092
<212> TYPE: DNA
<213> ORGANISM: Artificial Sequence
<220> FEATURE:
<223> OTHER INFORMATION: Codon optimized

<400> SEQUENCE: 19
actagtatgg tttatcatc cgtctgtact ttctccttcc aaactaacta tcataccttla       60 ttgaatcctc acaacaacaa tccaaaaaca tcattgttgt gttacagaca tccaaagaca      120
cctattaagt actcttacaa caactttcca tcaaaacatt gttcaaccaa gtccttccac      180
ttacaaaata agtgctccga aagtttgtct atagctaaga actctatcag agctgcaact      240
acaaatcaaa ctgaaccacc tgaaagtgat aatcactctg ttgccacaaa attttgaac      300 ttcggtaaag catgttggaa gttgcaaaga ccatacacca taatcgcttt tacttcttgt      360
gcatgcggtt tattcggtaa agaattgttg cataacacta acttaatttc atggtcctat      420
gaactgctcc gcattctctt tctggttcgt ctgtaaaata atcttcttct tcttgtcctt      480
caacatccaa atctccatcg caaatccaca agaaaacttt tgaagtgtt ctccgaata       540 catcccaaac aaccctgcta acccaaagtt tatatatact caacatgatc aattgtacat      600
gtccgttttg aacagtacca tccaaaattt tgagattcact tctgacacta caccaaaacc      660
tttagtcatt gttacaccct ccaatgttag tcacattcaa gcttctatat tgtgctctaa      720
```

```
gaaagtaggt tgcaaatca gaactagatc aggtggtcat gatgcagaag gcatgtctta      780
catctcacaa gttccattcg ttgtagtcga tttgagaaat atgcattcca taaagatcga      840
cgttcacagt caaacagcat gggtagaagc aggtgccacc ttgggtgaag tttactactg      900
gatcaacgaa aagaatgaaa acttttcttt ccctggtggt tactgtccaa cagtaggtgt      960
cggtggtcac ttttctggtg gtggttatgg tgcattgatg agaaactacg gtttagctgc     1020
agataatatt atagacgccc atttggttaa cgtagatggt aaagttttgg acagaaagtc     1080
tatgggtgaa gatttgtttt gggccataag aggtggtggt ggtgaaaatt cggtatcat      1140 tgccgcttgg aaaattaagt tagtcgctgt tccttccaaa agtactattt tctctgtcaa     1200
aaagaacatg gaaatccacg gtttggttaa gttgtttaat aagtggcaaa acatcgctta     1260
caagtacgat aaggacttgg ttttgatgac ccatttcatc actaaaaata ttacagataa     1320
ccatggtaaa aataagacca ctgttcacgg ttattttttct tcaatttttcc atggtggtgt     1380 agattctttg gttgatttga tgaataagtc attcccagaa ttgggtatta aaaagacaga     1440
ttgcaaggaa ttttcttgga tagacacaac catcttctat tcaggtgttg taaacttcaa     1500
caccgctaac ttcaaaaagg aaatcttgtt ggatagatcc gctggtaaaa agaccgcttt     1560
ttctattaaa ttggactacg ttaagaaacc aatccctgaa actgcaatgg tcaagatatt     1620
ggaaaagttg tacgaagaag atgtaggtgt cggcatgtac gtttttgtatc catacggtgg     1680 tattatggaa gaaatatctg aatcagccat accatttcct cacagagctg gtatcatgta     1740
tgaattatgg tacacagcct catgggaaaa gcaagaagat aacgaaaagc atatcaactg     1800
ggtcagatcc gtttacaact tcactacacc ttacgttagt caaaacccaa gattggcata     1860
tttgaactac agagatttgg acttaggtaa aactaacccct gaatctccaa ataactatac     1920
acaagcaaga atttggggtg aaaagtactt tggtaaaaat ttcaacagat tagttaaagt     1980
aaagactaaa gccgacccta caacttttt cagaaacgaa caatccatcc cacctttgcc     2040
acctcaccac cacgaacaaa aattaataag tgaagaagat ttgtaagtcg ac             2092
```

<210> SEQ ID NO 20
<211> LENGTH: 7904
<212> TYPE: DNA
<213> ORGANISM: Artificial Sequence
<220> FEATURE:
<223> OTHER INFORMATION: Codon optimized

<400> SEQUENCE: 20

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc      180
accatatcga ctacgtcgta aggccgtttc tgacagagta aaattcttga gggaactttc      240
accattatgg gaaatggttc aagaaggtat tgacttaaac tccatcaaat ggtcaggtca      300
ttgagtgttt tttatttgtt gtattttttt tttttagag aaaatcctcc aatatcaaat      360
taggaatcgt agtttcatga ttttctgtta cacctaactt tttgtgtggt gccctcctcc      420
ttgtcaatat taatgttaaa gtgcaattct ttttccttat cacgttgagc cattagtatc      480
aatttgctta cctgtattcc tttactatcc tcctttttct ccttcttgat aaatgtatgt      540
agattgcgta tatagtttcg tctaccctat gaacatattc catttgtaa tttcgtgtcg      600 tttctattat gaatttcatt tataaagttt atgtacaaat atcataaaaa aagagaatct      660
```

```
ttttaagcaa ggattttctt aacttcttcg gcgacagcat caccgacttc ggtggtactg       720
ttggaaccac ctaaatcacc agttctgata cctgcatcca aaacctttt aactgcatct        780 tcaatggcct taccttcttc aggcaagttc aatgacaatt tcaacatcat tgcagcagac      840
aagatagtgg cgatagggtc aaccttattc tttggcaaat ctggagcaga accgtggcat      900
ggttcgtaca aaccaaatgc ggtgttcttg tctggcaaag aggccaagga cgcagatggc      960
aacaaaccca aggaacctgg gataacggag gcttcatcgg agatgatatc accaaacatg     1020
ttgctggtga ttataatacc atttaggtgg gttgggttct taactaggat catggcggca     1080
gaatcaatca attgatgttg aaccttcaat gtagggaatt cgttcttgat ggtttcctcc     1140
acagtttttc tccataatct tgaagaggcc aaaacattag ctttatccaa ggaccaaata     1200
ggcaatggtg gctcatgttg tagggccatg aaagcggcca ttcttgtgat tctttgcact     1260
tctggaacgg tgtattgttc actatcccaa gcgacaccat caccatcgtc ttcctttctc     1320
ttaccaaagt aaatacctcc cactaattct ctgacaacaa cgaagtcagt acctttagca     1380
aattgtggct tgattggaga taagtctaaa agagagtcgg atgcaaagtt acatggtctt     1440
aagttggcgt acaattgaag ttctttacgg attttttagta aaccttgttc aggtctaaca    1500
ctaccggtac cccatttagg accacccaca gcacctaaca aaacggcatc aaccttcttg     1560
gaggcttcca gcgcctcatc tggaagtggg acacctgtag catcgatagc agcaccacca     1620
attaaatgat tttcgaaatc gaacttgaca ttggaacgaa catcagaaat gctttaaga     1680 accttaatgg cttcggctgt gatttcttga ccaacgtggt cacctggcaa acgacgatc     1740 ttcttagggg cagacatagg ggcagacatt agaatgtat atccttgaaa tatatatata     1800
tattgctgaa atgtaaaagg taagaaaagt tagaaagtaa gacgattgct aaccacctat     1860
tggaaaaaac aataggtcct taaataatat tgtcaacttc aagtattgtg atgcaagcat     1920
ttagtcatga acgcttctct attctatatg aaaagccggt tccggcctct cacctttcct     1980
ttttctccca atttttcagt tgaaaaaggt atatgcgtca ggcgacctct gaaattaaca     2040
aaaaatttcc agtcatcgaa tttgattctg tgcgatagcg cccctgtgtg ttctcgttat     2100
gttgaggaaa aaaataatgg ttgctaagag attcgaactc ttgcatctta cgatacctga     2160
gtattcccac agttaactgc ggtcaagata tttcttgaat caggcgcctt agaccgctcg     2220
gccaaacaac caattacttg ttgagaaata gagtataatt atcctataaa tataacgttt     2280
ttgaacacac atgaacaagg aagtacagga caattgattt tgaagagaat gtggattttg    2340
atgtaattgt tgggattcca tttttaataa ggcaataata ttaggtatgt ggatatacta     2400
gaagttctcc tcgagggtcg atatgcggtg tgaaataccg cacagatgcg taaggagaaa     2460
ataccgcatc aggaaattgt aaacgttaat attttgttaa aattcgcgtt aaattttgt      2520 taaatcagct cattttttaa ccaataggcc gaaatcggca aatcccctta taaatcaaaa     2580
gaatagaccg agatagggtt gagtgttgtt ccagtttgga acaagagtcc actattaaag     2640
aacgtggact ccaacgtcaa agggcgaaaa accgtctatc agggcgatgg cccactacgt     2700
gaaccatcac cctaatcaag ttttttgggg tcgaggtgcc gtaaagcact aaatcggaac     2760
cctaaaggga gcccccgatt tagagcttga cggggaaagc cggcgaacgt ggcgagaaag     2820
gaagggaaga aagcgaaagg agcgggcgct agggcgctgg caagtgtagc ggtcacgctg     2880
cgcgtaacca ccacacccgc cgcgcttaat gcgccgctac agggcgcgtc gcgccattcg     2940
ccattcaggc tgcgcaactg ttgggaaggg cgatcggtgc gggcctcttc gctattacgc     3000
cagctggcga aggggggatg tgctgcaagg cgattaagtt gggtaacgcc agggttttcc     3060
```

```
cagtcacgac gttgtaaaac gacggccagt gaattgtaat acgactcact atagggcgaa    3120
ttggagctct agtacggatt agaagccgcc gagcgggcga cagccctccg acggaagact    3180
ctcctccgtg cgtcctcgtc ttcaccggtc gcgttcctga aacgcagatg tgcctcgcgc    3240
cgcactgctc cgaacaataa agattctaca atactagctt ttatggttat gaagaggaaa    3300
aattggcagt aacctggccc cacaaacctt caaattaacg aatcaaatta caaccatag    3360 gatgataatg cgattagttt tttagcctta tttctggggt aattaatcag cgaagcgatg    3420
atttttgatc tattaacaga tatataaatg gaaaagctgc ataaccactt taactaatac    3480
tttcaacatt ttcagtttgt attacttctt attcaaatgt cataaaagta tcaacaaaaa    3540
attgttaata tacctctata ctttaacgtc aaggagaaaa accccggat tctagaacta    3600 gtggatcccc catcacaagt ttgtacaaaa aagctgaacg agaacgtaa aatgatataa    3660 atatcaatat attaaattag attttgcata aaaaacagac tacataatac tgtaaaacac    3720
aacatatcca gtcactatgg cggccgcatt aggcacccca ggctttacac tttatgcttc    3780
cggctcgtat aatgtgtgga ttttgagtta ggatccgtcg agattttcag gagctaagga    3840
agctaaaatg gagaaaaaaa tcactggata taccaccgtt gatatatccc aatggcatcg    3900
taaagaacat tttgaggcat ttcagtcagt tgctcaatgt acctataacc agaccgttca    3960
gctggatatt acggcctttt aaagaccgt aaagaaaaat aagcacaagt tttatccggc    4020
ctttattcac attcttgccc gcctgatgaa tgctcatccg gaattccgta tggcaatgaa    4080
agacggtgag ctggtgatat gggatagtgt tcacccttgt tacaccgttt tccatgagca    4140
aactgaaacg ttttcatcgc tctggagtga ataccacgac gatttccggc agtttctaca    4200
catatattcg caagatgtgg cgtgttacgg tgaaaacctg gcctatttcc ctaaagggtt    4260
tattgagaat atgtttttcg tctcagccaa tccctgggtg agtttcacca gttttgattt    4320
aaacgtggcc aatatggaca acttcttcgc cccgttttc accatgggca aatattatac    4380
gcaaggcgac aaggtgctga tgccgctggc gattcaggtt catcatgccg tctgtgatgg    4440
cttccatgtc ggcagaatgc ttaatgaatt acaacagtac tgcgatgagt ggcagggcgg    4500
ggcgtaaacg ccgcgtggat ccggcttact aaaagccaga taacagtatg cgtatttgcg    4560
cgctgatttt tgcggtataa gaatatatac tgatatgtat acccgaagta tgtcaaaaag    4620
aggtatgcta tgaagcagcg tattacagtg acagttgaca cgacagcta tcagttgctc    4680 aaggcatata tgatgtcaat atctccggtc tggtaagcac aaccatgcag aatgaagccc    4740
gtcgtctgcg tgccgaacgc tggaaagcgg aaaatcagga agggatgct gaggtcgccc    4800 ggtttattga aatgaacggc tcttttgctg acgagaacag gggctggtga atgcagttt    4860 aaggtttaca cctataaaag agagagccgt tatcgtctgt tgtggatgt acagagtgat    4920 attattgaca cgcccgggcg acggatggtg atcccctgg ccagtgcacg tctgctgtca    4980
gataaagtct cccgtgaact ttacccggtg gtgcatatcg gggatgaaag ctggcgcatg    5040
atgaccaccg atatggccag tgtgccggtc tccgttatcg gggaagaagt ggctgatctc    5100
agccaccgcg aaaatgacat caaaaacgcc attaacctga tgttctgggg aataaaatg    5160 tcaggctccc ttatacacag ccagtctgca ggtcgaccat agtgactgga tatgttgtgt    5220
tttacagtat tatgtagtct gttttttatg caaaatctaa tttaatatat tgatatttat    5280
atcattttac gtttctcgtt cagctttctt gtacaaagtg gtgatgggct gcaggaattc    5340
gatatcaagc ttatcgatac cgtcgacctc gagtcatgta attagttatg tcacgcttac    5400
```

```
attcacgccc tcccccaca tccgctctaa ccgaaaagga aggagttaga caacctgaag      5460
tctaggtccc tatttatttt tttatagtta tgttagtatt aagaacgtta tttatatttc      5520
aaattttct ttttttctg tacagacgcg tgtacgcatg taacattata ctgaaaacct      5580
tgcttgagaa ggttttggga cgctcgaagg ctttaatttg cggccggtac ccagcttttg      5640
ttcccttag tgagggttaa ttccgagctt ggcgtaatca tggtcatagc tgtttcctgt      5700
gtgaaattgt tatccgctca caattccaca acatagga gccggaagca taagtgtaa      5760
agcctgggt gcctaatgag tgaggtaact cacattaatt gcgttgcgct cactgcccgc      5820
tttccagtcg ggaaacctgt cgtgccagct gcattaatga atcggccaac gcgcggggag      5880
aggcggtttg cgtattgggc gctcttccgc ttcctcgctc actgactcgc tgcgctcggt      5940
cgttcggctg cggcgagcgg tatcagctca ctcaaaggcg gtaataccggt tatccacaga      6000
atcaggggat aacgcaggaa agaacatgtg agcaaaaggc cagcaaaagg ccaggaaccg      6060
taaaaaggcc gcgttgctgg cgttttcca taggctcggc cccctgacg agcatcacaa      6120
aaatcgacgc tcaagtcaga ggtggcgaaa cccgacagga ctataaagat accaggcgtt      6180
ccccctgga agctccctcg tgcgctctcc tgttccgacc ctgccgctta ccggatacct      6240
gtccgcctt ctcccttcgg gaagcgtggc gctttctcaa tgctcacgct gtaggtatct      6300
cagttcggtg taggtcgttc gctccaagct gggctgtgtg cacgaacccc ccgttcagcc      6360
cgaccgctgc gccttatccg gtaactatcg tcttgagtcc aacccggtaa gacacgactt      6420
atcgccactg gcagcagcca ctggtaacag gattagcaga gcgaggtatg taggcggtgc      6480
tacagagttc ttgaagtggt ggcctaacta cggctacact agaaggacag tatttggtat      6540
ctgcgctctg ctgaagccag ttaccttcgg aaaaagagtt ggtagctctt gatccggcaa      6600
acaaaccacc gctggtagcg gtggtttttt tgtttgcaag cagcagatta cgcgcagaaa      6660
aaaaggatct caagaagatc ctttgatctt ttctacgggg tctgacgctc agtggaacga      6720
aaactcacgt taagggattt tggtcatgag attatcaaaa aggatcttca cctagatcct      6780
tttaaattaa aaatgaagtt ttaaatcaat ctaaagtata tatgagtaaa cttggtctga      6840
cagttaccaa tgcttaatca gtgaggcacc tatctcagcg atctgtctat ttcgttcatc      6900
catagttgcc tgactgcccg tcgtgtagat aactacgata cgggagggct taccatctgg      6960
ccccagtgct gcaatgatac cgcgagaccc acgctcaccg gctccagatt tatcagcaat      7020
aaaccagcca gccggaaggg ccgagcgcag aagtggtcct gcaactttat ccgcctccat      7080
ccagtctatt aattgttgcc gggaagctag agtaagtagt tcgccagtta atagtttgcg      7140
caacgttgtt gccattgcta caggcatcgt ggtgtcacgc tcgtcgtttg gtatggcttc      7200
attcagctcc ggttcccaac gatcaaggcg agttacatga tcccccatgt tgtgaaaaaa      7260
agcggttagc tccttcggtc ctccgatcgt tgtcagaagt aagttggccg cagtgttatc      7320
actcatggtt atggcagcac tgcataattc tcttactgtc atgccatccg taagatgctt      7380
ttctgtgact ggtgagtact caaccaagtc attctgagaa tagtgtatgc ggcgaccgag      7440
ttgctcttgc ccggcgtcaa tacgggataa taccgcgcca catagcagaa ctttaaaagt      7500
gctcatcatt ggaaaacgtt cttcggggcg aaaactctca aggatcttac cgctgttgag      7560
atccagttcg atgtaaccca ctcgtgcacc caactgatct tcagcatctt ttactttcac      7620
cagcgtttct gggtgagcaa aaacaggaag gcaaaatgcc gcaaaaaagg gaataagggc      7680
gacacggaaa tgttgaatac tcatactctt ccttttcaa tattattgaa gcatttatca      7740
gggttattgt ctcatgagcg gatacatatt tgaatgtatt tagaaaaata aacaaatagg      7800
```

<210> SEQ ID NO 21
<211> LENGTH: 6773
<212> TYPE: DNA
<213> ORGANISM: Artificial Sequence
<220> FEATURE:
<223> OTHER INFORMATION: Codon optimized

<400> SEQUENCE: 21

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accacgcttt tcaattcaat tcatcatttt ttttttattc tttttttttga tttcggtttc    240
tttgaaattt ttttgattcg gtaatctccg aacagaagga agaacgaagg aaggagcaca    300
gacttagatt ggtatatata cgcatatgta gtgttgaaga acatgaaatt gcccagtat     360
tcttaaccca actgcacaga acaaaaacct gcaggaaacg aagataaatc atgtcgaaag    420
ctacatataa ggaacgtgct gctactcatc ctagtcctgt tgctgccaag ctatttaata    480
tcatgcacga aaagcaaaca aacttgtgtg cttcattgga tgttcgtacc accaaggaat    540
tactggagtt agttgaagca ttaggtccca aaatttgttt actaaaaaca catgtggata    600
tcttgactga ttttccatg gagggcacag ttaagccgct aaaggcatta tccgccaagt     660
acaatttttt actcttcgaa gacagaaaat tgctgacat tggtaataca gtcaaattgc     720
agtactctgc gggtgtatac agaatagcag aatgggcaga cattacgaat gcacacggtg    780
tggtgggccc aggtattgtt agcggtttga agcaggcggc agaagaagta acaaaggaac    840
ctagaggcct tttgatgtta gcagaattgt catgcaaggg ctccctatct actggagaat    900
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag ggaagggatg   1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta acgttaata ttttgttaaa attcgcgtta    1380
aatttttgtt aaatcagctc attttttaac caataggccg aaatcggcaa atcccttat    1440
aaatcaaaag aatagaccga datagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttgggt cgaggtgccg taaagcacta    1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa ggggggatgt gctgcaaggc gattaagttg ggtaacgcca   1920
```

```
gggttttccc agtcacgacg ttgtaaaacg acggccagtg aattgtaata cgactcacta    1980
tagggcgaat ggagctcta gtacggatta gaagccgccg agcgggcgac agccctccga     2040
cggaagactc tcctccgtgc gtcctcgtct tcaccggtcg cgttcctgaa acgcagatgt    2100
gcctcgcgcc gcactgctcc gaacaataaa gattctacaa tactagcttt tatggttatg    2160
aagaggaaaa attggcagta acctggcccc acaaaccttc aaattaacga atcaaattaa    2220
caaccatagg atgataatgc gattagtttt ttagccttat ttctggggta attaatcagc    2280
gaagcgatga tttttgatct attaacagat atataaatgg aaaagctgca taaccacttt    2340
aactaatact ttcaacattt tcagtttgta ttacttctta ttcaaatgtc ataaaagtat    2400
caacaaaaaa ttgttaatat acctctatac tttaacgtca aggagaaaaa accccggatt    2460
ctagaactag tggatccccc atcacaagtt tgtacaaaaa agctgaacga aaacgtaaa     2520 atgatataaa tatcaatata ttaaattaga ttttgcataa aaaacagact acataatact    2580
gtaaaacaca acatatccag tcactatggc ggccgcatta ggcacccag gctttacact     2640 ttatgcttcc ggctcgtata atgtgtggat ttgagttag gatccgtcga gattttcagg     2700
agctaaggaa gctaaaatgg agaaaaaaat cactggatat accaccgttg atatatccca    2760
atggcatcgt aaagaacatt tgaggcatt tcagtcagtt gctcaatgta cctataacca     2820
gaccgttcag ctggatatta cggccttttt aaagaccgta agaaaaata agcacaagtt    2880 ttatccggcc tttattcaca ttcttgcccg cctgatgaat gctcatccgg aattccgtat    2940
ggcaatgaaa gacggtgagc tggtgatatg ggatagtgtt caccctgtt acaccgtttt    3000 ccatgagcaa actgaaacgt tttcatcgct ctggagtgaa taccacgacg atttccggca    3060
gtttctacac atatattcgc aagatgtggc gtgttacggt gaaaacctgg cctatttccc    3120
taaagggttt attgagaata tgttttttcgt ctcagccaat ccctgggtga gtttcaccag   3180
ttttgattta aacgtggcca atatggacaa cttcttcgcc cccgttttca ccatgggcaa    3240
atattatacg caaggcgaca aggtgctgat gccgctggcg attcaggttc atcatgccgt    3300
ctgtgatggc ttccatgtcg cagaatgct taatgaatta caacagtact gcgatgagtg    3360
gcagggcggg gcgtaaacgc cgcgtggatc cggcttacta aaagccagat aacagtatgc    3420
gtatttgcgc gctgattttt gcggtataag aatatatact gatatgtata cccgaagtat    3480
gtcaaaaaga ggtatgctat gaagcagcgt attacagtga cagttgacag cgacagctat    3540
cagttgctca aggcatatat gatgtcaata tctccggtct ggtaagcaca accatgcaga    3600
atgaagcccg tcgtctgcgt gccgaacgct ggaaagcgga aaatcaggaa gggatggctg    3660
aggtcgcccg gtttattgaa atgaacggct cttttgctga cgagaacagg ggctggtgaa    3720
atgcagttta aggtttacac ctataaaaga gagagccgtt atcgtctgtt tgtggatgta    3780
cagagtgata ttattgacac gcccgggcga cggatggtga tcccctggc cagtgcacgt    3840 ctgctgtcag ataaagtctc ccgtgaactt taccggtgg tgcatatcgg ggatgaaagc    3900
tggcgcatga tgaccaccga tatggccagt gtgccggtct ccgttatcgg ggaagaagtg    3960
gctgatctca gccaccgcga aaatgacatc aaaaacgcca ttaacctgat gttctgggga    4020
atataaatgt caggctccct tatacacagc cagtctgcag gtcgaccata gtgactggat    4080
atgttgtgtt ttacagtatt atgtagtctg ttttttatgc aaaatctaat ttaatatatt    4140
gatatttata tcattttacg tttctcgttc agctttcttg tacaaagtgg tgatgggctg    4200
caggaattcg atatcaagct tatcgatacc gtcgacctcg agtcatgtaa ttagttatgt    4260
cacgcttaca ttcacgccct cccccacat ccgctctaac cgaaaaggaa ggagttagac    4320
```

```
aacctgaagt ctaggtccct atttattttt ttatagttat gttagtatta agaacgttat    4380
ttatatttca aattttttctt ttttttctgt acagacgcgt gtacgcatgt aacattatac    4440
tgaaaacctt gcttgagaag gttttgggac gctcgaaggc tttaatttgc ggccggtacc    4500
cagcttttgt tccctttagt gagggttaat tccgagcttg gcgtaatcat ggtcatagct    4560
gtttcctgtg tgaaattgtt atccgctcac aattccacac aacataggag ccggaagcat    4620
aaagtgtaaa gcctggggtg cctaatgagt gaggtaactc acattaattg cgttgcgctc    4680
actgcccgct ttccagtcgg gaaacctgtc gtgccagctg cattaatgaa tcggccaacg    4740
cgcggggaga ggcggtttgc gtattgggcg ctcttccgct tcctcgctca ctgactcgct    4800
gcgctcggtc gttcggctgc ggcgagcggt atcagctcac tcaaaggcgg taatacggtt    4860
atccacagaa tcaggggata acgcaggaaa gaacatgtga gcaaaaggcc agcaaaaggc    4920
caggaaccgt aaaaaggccg cgttgctggc gtttttccat aggctcggcc cccctgacga    4980
gcatcacaaa aatcgacgct caagtcagag gtggcgaaac ccgacaggac tataaagata    5040
ccaggcgttc cccctggaa gctccctcgt gcgctctcct gttccgaccc tgccgcttac    5100
cggatacctg tccgcctttc tcccttcggg aagcgtggcg ctttctcaat gctcacgctg    5160
taggtatctc agttcggtgt aggtcgttcg ctccaagctg ggctgtgtgc acgaaccccc    5220
cgttcagccc gaccgctgcg ccttatccgg taactatcgt cttgagtcca acccggtaag    5280
acacgactta tcgccactgg cagcagccac tggtaacagg attagcagag cgaggtatgt    5340
aggcggtgct acagagttct tgaagtggtg gcctaactac ggctacacta aaggacagt    5400
atttggtatc tgcgctctgc tgaagccagt taccttcgga aaaagagttg gtagctcttg    5460
atccggcaaa caaaccaccg ctggtagcgg tggttttttt gtttgcaagc agcagattac    5520
gcgcagaaaa aaaggatctc aagaagatcc tttgatcttt tctacggggt ctgacgctca    5580
gtggaacgaa aactcacgtt aagggatttt ggtcatgaga ttatcaaaaa ggatcttcac    5640
ctagatcctt ttaaattaaa aatgaagttt taaatcaatc taaagtatat atgagtaaac    5700
ttggtctgac agttaccaat gcttaatcag tgaggcacct atctcagcga tctgtctatt    5760
tcgttcatcc atagttgcct gactgcccgt cgtgtagata actacgatac gggagggctt    5820
accatctggc cccagtgctg caatgatacc gcgagaccca cgctcaccgg ctccagattt    5880
atcagcaata accagccag ccggaagggc cgagcgcaga agtggtcctg caactttatc    5940
cgcctccatc cagtctatta attgttgccg ggaagctaga gtaagtagtt cgccagttaa    6000
tagtttgcgc aacgttgttg ccattgctac aggcatcgtg gtgtcacgct cgtcgtttgg    6060
tatggcttca ttcagctccg gttcccaacg atcaaggcga gttacatgat cccccatgtt    6120
gtgaaaaaaa gcggttagct ccttcggtcc tccgatcgtt gtcagaagta agttggccgc    6180
agtgttatca ctcatggtta tggcagcact gcataattct cttactgtca tgccatccgt    6240
aagatgcttt tctgtgactg gtgagtactc aaccaagtca ttctgagaat agtgtatgcg    6300
gcgaccgagt tgctcttgcc cggcgtcaat acgggataat accgcgccac atagcagaac    6360
tttaaaagtg ctcatcattg gaaaacgttc ttcggggcga aaactctcaa ggatcttacc    6420
gctgttgaga tccagttcga tgtaacccac tcgtgcaccc aactgatctt cagcatcttt    6480
tactttcacc agcgtttctg ggtgagcaaa aacaggaagg caaaatgccg caaaaaaggg    6540
aataagggcg acacggaaat gttgaatact catactcttc ctttttcaat attattgaag    6600
catttatcag ggttattgtc tcatgagcgg atacatattt gaatgtattt agaaaaataa    6660
```

| | | | | |
|---|---|---|---|---|
| acaaataggg | gttccgcgca | catttccccg | aaaagtgcca | cctgacgtct | aagaaaccat | 6720 |
| tattatcatg | acattaacct | ataaaaatag | gcgtatcacg | aggcccttc | gtc | 6773 |

<210> SEQ ID NO 22
<211> LENGTH: 7690
<212> TYPE: DNA
<213> ORGANISM: Artificial Sequence
<220> FEATURE:
<223> OTHER INFORMATION: Codon optimized

<400> SEQUENCE: 22

| | | | | | |
|---|---|---|---|---|---|
| ttatcatgac | attaacctat | aaaaataggc | gtatcacgag | gccctttcgt | ctcgcgcgtt | 60 |
| tcggtgatga | cggtgaaaac | ctctgacaca | tgcagctccc | ggagacggtc | acagcttgtc | 120 |
| tgtaagcgga | tgccgggagc | agacaagccc | gtcaggcgc | gtcagcgggt | gttggcgggt | 180 |
| gtcgggctg | gcttaactat | gcggcatcag | agcagattgt | actgagagtg | caccacgctt | 240 |
| ttcaattcaa | ttcatcattt | ttttttatt | ctttttttg | atttcggttt | ctttgaaatt | 300 |
| tttttgattc | ggtaatctcc | gaacagaagg | aagaacgaag | gaaggagcac | agacttagat | 360 |
| tggtatatat | acgcatatgt | agtgttgaag | aaacatgaaa | ttgcccagta | ttcttaaccc | 420 |
| aactgcacag | aacaaaaacc | tgcaggaaac | gaagataaat | catgtcgaaa | gctacatata | 480 |
| aggaacgtgc | tgctactcat | cctagtcctg | ttgctgccaa | gctatttaat | atcatgcacg | 540 |
| aaaagcaaac | aaacttgtgt | gcttcattgg | atgttcgtac | caccaaggaa | ttactggagt | 600 |
| tagttgaagc | attaggtccc | aaaatttgtt | tactaaaaac | acatgtggat | atcttgactg | 660 |
| atttttccat | ggagggcaca | gttaagccgc | taaaggcatt | atccgccaag | tacaattttt | 720 |
| tactcttcga | agacagaaaa | tttgctgaca | ttggtaatac | agtcaaattg | cagtactctg | 780 |
| cgggtgtata | cagaatagca | gaatgggcag | acattacgaa | tgcacacggt | gtggtgggcc | 840 |
| caggtattgt | tagcggtttg | aagcaggcgg | cagaagaagt | aacaaaggaa | cctagaggcc | 900 |
| ttttgatgtt | agcagaattg | tcatgcaagg | gctccctatc | tactggagaa | tatactaagg | 960 |
| gtactgttga | cattgcgaag | agcgacaaag | attttgttat | cggctttatt | gctcaaagag | 1020 |
| acatgggtgg | aagagatgaa | ggttacgatt | ggttgattat | gacacccggt | gtgggtttag | 1080 |
| atgacaaggg | agacgcattg | ggtcaacagt | atagaaccgt | ggatgatgtg | gtctctacag | 1140 |
| gatctgacat | tattattgtt | ggaagaggac | tatttgcaaa | gggaagggat | gctaaggtag | 1200 |
| agggtgaacg | ttacagaaaa | gcaggctggg | aagcatattt | gagaagatgc | ggccagcaaa | 1260 |
| actaaaaaac | tgtattataa | gtaaatgcat | gtatactaaa | ctcacaaatt | agagcttcaa | 1320 |
| tttaattata | tcagttatta | ccctgcggtg | tgaaataccg | cacagatgcg | taaggagaaa | 1380 |
| ataccgcatc | aggaaattgt | aaacgttaat | attttgttaa | aattcgcgtt | aaatttttgt | 1440 |
| taaatcagct | cattttttaa | ccaataggcc | gaaatcggca | aaatccctta | taaatcaaaa | 1500 |
| gaatagaccg | agatagggtt | gagtgttgtt | ccagtttgga | acaagagtcc | actattaaag | 1560 |
| aacgtggact | ccaacgtcaa | agggcgaaaa | accgtctatc | agggcgatgg | cccactacgt | 1620 |
| gaaccatcac | cctaatcaag | ttttttgggg | tcgaggtgcc | gtaaagcact | aaatcggaac | 1680 |
| cctaaaggga | gcccccgatt | tagagcttga | cggggaaagc | cggcgaacgt | ggcgagaaag | 1740 |
| gaagggaaga | aagcgaaagg | agcgggcgct | agggcgctgg | caagtgtagc | ggtcacgctg | 1800 |
| cgcgtaacca | ccacacccgc | cgcgcttaat | gcgccgctac | agggcgcgtc | gcgccattcg | 1860 |
| ccattcaggc | tgcgcaactg | ttgggaaggg | cgatcggtgc | gggcctcttc | gctattacgc | 1920 |
| cagctggcga | aggggggatg | tgctgcaagg | cgattaagtt | gggtaacgcc | agggttttcc | 1980 |

```
cagtcacgac gttgtaaaac gacggccagt gaattgtaat acgactcact atagggcgaa    2040
ttggagctct agtacggatt agaagccgcc gagcgggcga cagccctccg acggaagact    2100
ctcctccgtg cgtcctcgtc ttcaccggtc gcgttcctga aacgcagatg tgcctcgcgc    2160
cgcactgctc cgaacaataa agattctaca atactagctt ttatggttat gaagaggaaa    2220
aattggcagt aacctggccc cacaaacctt caaattaacg aatcaaatta acaaccatag    2280
gatgataatg cgattagttt tttagcctta tttctggggt aattaatcag cgaagcgatg    2340
atttttgatc tattaacaga tatataaatg gaaaagctgc ataaccactt taactaatac    2400
tttcaacatt ttcagtttgt attacttctt attcaaatgt cataaaagta tcaacaaaaa    2460
attgttaata tacctctata ctttaacgtc aaggagaaaa accccggat tctagaacta     2520 gtggatcccc catcatggtt tccaatcact tgtttgacgc aatgagagcc gctgcccctg    2580
gtaacgcccc tttcataaga atagataata ctagaacttg gacatacgat gacgcctttg    2640
ctttatctgg tagaatagca tcagctatgg atgctttggg tatcagacca ggtgacagag    2700
tcgcagttca agtagaaaaa tccgctgaag cattgatctt gtatttggct tgtttgagaa    2760
gtggtgcagt ttatttgcca ttgaatactg cctacacatt agctgaattg gattacttca    2820
taggtgacgc agaacctaga ttggttgtag tcgcctcttc agccagagct ggtgtagaaa    2880
caattgctaa accaagaggt gcaatagtcg aaaccttaga tgctgctggt tctggtagtt    2940
tgttagattt ggccagagac gaacctgctg attttgttga cgcttcaaga tcagccgatg    3000
acttagccgc tattttgtac acctctggta ctacaggtag atcaaagggt gctatgttga    3060
ctcatggtaa tttgttgtca aacgcattaa ccttgagaga tttctggaga gttactgccg    3120
gtgacagatt aatccacgct ttgccaattt ttcatactca cggtttattc gttgctacca    3180
acgtaacttt gttagcaggt gcctccatgt tcttgttgag taagttcgat ccagaagaaa    3240
tattatcttt gatgcctcaa gctactatgt tgatgggtgt cccaacattc tacgttagat    3300
tgttacaatc acctagatta gataagcaag ctgttgcaaa catcagattg tttatatccg    3360
gtagtgctcc attgttagca gaaacccata ctgaatttca agcaagaaca ggtcacgcca    3420
ttttagaaag atacggtatg acagaaacca atatgaacac ttctaaccct tatgaaggta    3480
aaagaatagc tggtacagtt ggttttccat tgcctgatgt cacagttaga gtaaccgacc    3540
cagccactgg tttagctttg ccacctgaac aaactggtat gatcgaaatt aaaggtccaa    3600
acgtttttaa gggttactgg agaatgcctg aaaagactgc tgctgagttt actgctgatg    3660
gtttctttat ctctggtgac ttaggtaaaa ttgatagaga cggttatgtc catattgttg    3720
gtcgtggtaa agatttggtt atatccggtg gttataacat ctaccctaag aagtagaag    3780 gtgaaataga tcaaatcgaa ggtgttgtag aatcagctgt aataggtgtc ccacatcctg    3840
attttggtga aggtgttaca gcagtcgttg taagaaaacc aggtgctgca ttagatgaaa    3900 aggcaaattgt ttctgcctta caagacagat tggctagata caagcaacca aagagaataa    3960
tcttcgcaga agatttgcct agaaatacta tgggtaaagt acaaaagaac atcttgagac    4020
aacaatacgc cgacttatac accagaaccg aaggtagagg ttctttgtta acatgtggtg    4080
acgttgaaga aaatccaggt cctatggctt cagaaaagga ataagaaga gaaagattct     4140 tgaacgtatt cccaaagtta gttgaagaat tgaacgctag tttgttagct tatggtatgc    4200
ctaaagaagc ctgcgattgg tatgctcact ctttaaacta caatactcca ggtggtaaat    4260
tgaatagagg tttgagtgta gttgatactt atgctatctt gtctaacaaa accgttgaac    4320
```

```
aattaggtca agaagaatac gaaaaggtcg ctatcttggg ttggtgtatt gaattgttgc    4380
aagcatactt tttggttgcc gatgacatga tggataagtc tataacaaga agaggtcaac    4440
catgctggta caaagttcca gaagttggtg aaatagccat aaatgatgct tttatgttgg    4500
aagccgctat ctataaattg ttgaagtcac atttcagaaa cgaaaagtac tacatcgata    4560
ttaccgaatt attccacgaa gttactttcc aaacagaatt gggtcaattg atggatttga    4620
taactgcacc tgaagataaa gttgacttgt caaagttttc cttgaagaaa cattcattca    4680
tcgtcacctt tgaaactgct tattactcct tctatttgcc agtcgccttg gctatgtacg    4740
tagctggtat tactgatgaa aaagacttga agcaagcaag agatgttttg atacctttgg    4800
gtgaatactt ccaaatccaa gatgactact tagactgttt cggtactcca gaacaaatag    4860
gtaaaatcgg tacagatatt caagacaata agtgcagttg ggttattaac aaggctttgg    4920
aattagcatc tgccgaacaa agaaagactt tggatgaaaa ctacggtaaa aaggactcag    4980
ttgctgaagc aaagtgtaag aaaattttta atgatttgaa gattgaacaa ttgtaccatg    5040
aatacgaaga atccatcgct aaagacttaa aggcaaagat tagtcaagtt gatgaatcaa    5100
gaggttttaa agccgacgtt ttgacagctt tcttgaataa ggtctacaag agatcaaagt    5160
gatgggctgc aggaattcga tatcaagctt atcgataccg tcgacctcga gtcatgtaat    5220
tagttatgtc acgcttacat tcacgccctc cccccacatc cgctctaacc gaaaaggaag    5280
gagttagaca acctgaagtc taggtcccta tttattttt tatagttatg ttagtattaa    5340
gaacgttatt tatatttcaa attttctttt tttttctgta cagacgcgtg tacgcatgta    5400
acattatact gaaaaccttg cttgagaagg ttttgggacg ctcgaaggct ttaatttgcg    5460
gccggtaccc agcttttgtt ccctttagtg agggttaatt ccgagcttgg cgtaatcatg    5520
gtcatagctg tttcctgtgt gaaattgtta tccgctcaca attccacaca ataggagc    5580 cggaagcata aagtgtaaag cctggggtgc ctaatgagtg aggtaactca cattaattgc    5640
gttgcgctca ctgcccgctt tccagtcggg aaacctgtcg tgccagctgc attaatgaat    5700
cggccaacgc gcggggagag gcggtttgcg tattgggcgc tcttccgctt cctcgctcac    5760
tgactcgctg cgctcggtcg ttcggctgcg gcgagcggta tcagctcact caaaggcggt    5820
aatacggtta tccacagaat caggggataa cgcaggaaag aacatgtgag caaaaggcca    5880
gcaaaaggcc aggaaccgta aaaaggccgc gttgctggcg tttttccata ggctcggccc    5940
ccctgacgag catcacaaaa atcgacgctc aagtcagagg tggcgaaacc cgacaggact    6000
ataaagatac caggcgttcc ccctggaag ctccctcgtg cgctctcctg ttccgaccct    6060
gccgcttacc ggatacctgt ccgcctttct cccttcggga agcgtggcgc tttctcaatg    6120
ctcacgctgt aggtatctca gttcggtgta ggtcgttcgc tccaagctgg gctgtgtgca    6180 cgaaccccc gttcagcccg accgctgcgc cttatccggt aactatcgtc ttgagtccaa    6240 cccgtaaga cacgacttat cgccactggc agcagccact ggtaacagga ttagcagagc    6300
gaggtatgta ggcggtgcta cagagttctt gaagtggtgg cctaactacg gctacactag    6360
aaggacagta tttggtatct gcgctctgct gaagccagtt accttcggaa aaagagttgg    6420
tagctcttga tccggcaaac aaaccaccgc tggtagcggt ggtttttttg tttgcaagca    6480
gcagattacg cgcagaaaaa aaggatctca agaagatcct ttgatctttt ctacggggtc    6540
tgacgctcag tggaacgaaa actcacgtta agggattttg gtcatgagat tatcaaaaag    6600
gatcttcacc tagatccttt taaattaaaa atgaagtttt aaatcaatct aaagtatata    6660
tgagtaaact tggtctgaca gttaccaatg cttaatcagt gaggcaccta tctcagcgat    6720
```

```
ctgtctattt cgttcatcca tagttgcctg actgcccgtc gtgtagataa ctacgatacg    6780
ggagggctta ccatctggcc ccagtgctgc aatgataccg cgagacccac gctcaccggc    6840
tccagattta tcagcaataa accagccagc cggaagggcc gagcgcagaa gtggtcctgc    6900
aactttatcc gcctccatcc agtctattaa ttgttgccgg gaagctagag taagtagttc    6960
gccagttaat agtttgcgca acgttgttgc cattgctaca ggcatcgtgg tgtcacgctc    7020
gtcgtttggt atggcttcat tcagctccgg ttcccaacga tcaaggcgag ttacatgatc    7080
ccccatgttg tgaaaaaaag cggttagctc cttcggtcct ccgatcgttg tcagaagtaa    7140
gttggccgca gtgttatcac tcatggttat ggcagcactg cataattctc ttactgtcat    7200
gccatccgta agatgctttt ctgtgactgg tgagtactca accaagtcat tctgagaata    7260
gtgtatgcgg cgaccgagtt gctcttgccc ggcgtcaata cgggataata ccgcgccaca    7320
tagcagaact ttaaaagtgc tcatcattgg aaaacgttct cggggcgaaa actctcaag    7380 gatcttaccg ctgttgagat ccagttcgat gtaaccccact cgtgcaccca actgatcttc    7440
agcatctttt actttcacca gcgtttctgg gtgagcaaaa acaggaaggc aaaatgccgc    7500
aaaaaaggga ataagggcga cacggaaatg ttgaatactc atactcttcc ttttcaata    7560 ttattgaagc atttatcagg gttattgtct catgagcgga tacatatttg aatgtattta    7620
gaaaaataaa caataggggg ttccgcgcac atttccccga aaagtgccac ctgacgtcta    7680
agaaaccatt                                                          7690
```

<210> SEQ ID NO 23
<211> LENGTH: 2163
<212> TYPE: DNA
<213> ORGANISM: Artificial Sequence
<220> FEATURE:
<223> OTHER INFORMATION: Codon optimized

<400> SEQUENCE: 23

```
atgggtaaaa actataagtc cttggattca gtcgttgcct cagatttcat cgcattgggt      60
atcacctcag aagtagcaga aacattacat ggtagattgg cagaaatcgt ttgtaattat    120
ggtgctgcaa cccctcaaac ttggatcaac atcgctaacc atatcttgtc accagatttg    180
cctttctcct tacaccaaat gttgttttat ggttgctaca aggatttcgg tccagcccca    240
cctgcttgga ttccagaccc tgaaaaagtc aagtcaacta atttgggtgc tttgttggaa    300
aagagaggta agaattttt gggtgtaaag tacaaagatc caatttcttc tttttctcac    360
ttccaagaat tttctgttag aaaccctgaa gtcattggaa acagtatt gatggatgaa    420 atgaaaatta gtttctctaa ggacccagaa tgtatcttga agagagatga catcaacaac    480
ccaggtggtt ctgaatggtt acctggtggt tacttgaact cagctaaaaa ttgcttgaac    540
gtaaactcca ataagaaatt gaacgatact atgatcgttt ggagagacga gggtaacgat    600
gacttgcctt tgaataagtt gacattagat caattgagaa agagagtttg gttggttggt    660
tatgcattgg aagaaatggg tttagaaaaa ggttgtgcaa tagccatcga tatgccaatg    720
catgttgatg ctgttgttat atatttggcc atagtattgg ctggttacgt agttgtctct    780
atagcagatt cattttccgc ccctgaaatc tcaactagat tgagattatc caaagctaag    840
gcaattttca cacaagatca catcatcaga ggtaaaaaga gaataccatt gtattcaaga    900
gtagttgaag ctaaatcccc aatggcaata gttatcccctt gtagtggttc taacattggt    960
gcagaattga gagatggtga catatcttgg gattactttt tagaaagagc caaggagttt   1020
```

```
aaaaactgcg agtttactgc cagagaacaa cctgttgatg cttatactaa catcttattc    1080
tccagtggta ctacaggtga accaaaagca attccttgga cacaagccac cccattgaag    1140
gctgctgctg atggttggtc tcatttggat attagaaaag gtgacgttat agtatggcca    1200
actaatttgg gttggatgat gggtccttgg ttggttttatg ctagtttgtt aaatggtgca    1260
tctattgcct tgtacaacgg tagtccttta gtctctggtt tcgctaaatt tgttcaagat    1320
gcaaaggtca caatgttggg tgtcgtacca tctattgtaa gatcatggaa atccacaaat    1380
tgtgtttcag gttacgattg gtccaccata agatgctttt cttcatccgg tgaagcctct    1440
aatgtagacg aatatttgtg gttaatgggt agagctaact acaagccagt tatagaaatg    1500
tgtggtggta cagaaatcgg tggtgctttt tctgctggtt cattttttgca agctcaatct    1560 ttaagttctt tttcatccca atgtatgggt tgcaccttgt acatattaga taagaacggt    1620
tacccaatgc ctaaaaataa gccaggtatc ggtgaattgg cattaggtcc tgttatgttt    1680
ggtgcctcaa aaacattgtt aaacggtaat catcacgatg tctatttcaa gggtatgcca    1740
accttgaatg gtgaagtatt gagaagacat ggtgacattt cgaattgac ctctaacggt    1800 tactaccatg cacacggtag agccgatgac actatgaaca tcggtggtat caaaattagt    1860
tctatcgaaa tcgaaagagt ctgtaatgaa gtagatgaca gagttttttga aaccactgct    1920 attggtgttc cacctttggg tggtggtcca gaacaattgg tcatattttt cgtattgaag    1980
gattcaaacg acacaaccat tgatttgaac caattgagat tatccttta cttgggtttg    2040 caaaagaaat tgaacccatt attcaaagtt actagagttg tcccattgtc atccttacct    2100
agaactgcaa caaacaagat catgagaaga gttttgagac aacaattcag tcatttcgaa    2160
tga                                                                  2163
```

<210> SEQ ID NO 24
<211> LENGTH: 1059
<212> TYPE: DNA
<213> ORGANISM: Artificial Sequence
<220> FEATURE:
<223> OTHER INFORMATION: Codon optimized

<400> SEQUENCE: 24

```
atggcttcag aaaaggaaat aagaagagaa agattcttga acgtattccc aaagttagtt      60
gaagaattga acgctagttt gttagcttat ggtatgccta agaagcctg cgattggtat     120 gctcactctt taaactacaa tactccaggt ggtaaattga atagaggttt gagtgtagtt     180
gatacttatg ctatcttgtc taacaaaacc gttgaacaat taggtcaaga gaatacgaa     240 aaggtcgcta tcttgggttg gtgtattgaa ttgttgcaag catacttttt ggttgccgat     300
gacatgatgg ataagtctat aacaagaaga ggtcaaccat gctggacaa agttccagaa     360 gttggtgaaa tagccataaa tgatgctttt atgttggaag ccgctatcta taaattgttg     420
aagtcacatt tcagaaacga aaagtactac atcgatatta ccgaattatt ccacgaagtt     480
actttccaaa cagaattggg tcaattgatg gatttgataa ctgcacctga agataaagtt     540
gacttgtcaa agttttcctt gaagaaacat tcattcatcg tcacctttga aactgcttat     600
tactccttct atttgccagt cgccttggct atgtacgtag ctggtattac tgatgaaaaa     660
gacttgaagc aagcaagaga tgtttttgata cctttgggtg aatacttcca aatccaagat     720
gactacttag actgtttcgg tactccagaa caaataggta aaatcggtac agatattcaa     780
gacaataagt gcagttgggt tattaacaag gctttggaat tagcatctgc cgaacaagga     840
aagactttgg atgaaaacta cggtaaaaag gactcagttg ctgaagcaaa gtgtaagaaa     900
```

```
attttttaatg atttgaagat tgaacaattg taccatgaat acgaagaatc catcgctaaa    960
gacttaaagg caaagattag tcaagttgat gaatcaagg  gttttaaagc cgacgttttg   1020
acagctttct tgaataaggt ctacaagaga tcaaagtag                          1059
```

<210> SEQ ID NO 25
<211> LENGTH: 1158
<212> TYPE: DNA
<213> ORGANISM: Artificial Sequence
<220> FEATURE:
<223> OTHER INFORMATION: Codon optimized

<400> SEQUENCE: 25

```
atgaaccatt tgagagccga aggtcctgcc tccgtattag ccataggtac agccaaccca     60
gaaaacatat tgatccaaga tgaatttcct gattattact tcagagttac caagagtgaa    120
cacatgactc aattgaagga aaagtttaga aaaatatgtg ataagtctat gatcagaaag    180
agaaactgct tcttgaacga agaacatttg aagcaaaatc caagattggt agaacacgaa    240
atgcaaacat ggatgccag  acaagacatg ttagttgtcg aagttcctaa attgggtaaa    300
gatgcttgtg caaaagccat taggaatgg  ggtcaaccaa agtcaaagat cactcatttg    360
atttttacaa gtgcatctac tacagatatg cctggtgcag actaccactg tgccaaattg    420
ttaggtttgt caccatccgt taagagagtc atgatgtatc aattaggttg ctacggtggt    480
ggtactgttt tgagaatcgc taaggatatt gcagaaaaca caagggtgc  cagagtatta    540 gctgtttgtt gcgacattat ggcttgcttt tttagaggtc caagtgattc tgacttggaa    600 tgttagttg  gtcaagctat cttcggtgac ggtgctgctg ctgttattgt tggtgcagaa    660
cctgacgaat ctgttggtga aagaccaata tttgaattag tcagtacagg tcaaaccatc    720
ttgcctaatt ctgaaggtac aattggtggt catataagag aagcaggttt gatcttcgat    780
ttgcacaaag acgttccaat gttaatctct aacaacatag aaaagtgttt gatagaagca    840
ttcactccta taggtatctc agattggaac tctatttttct ggataacaca tccaggtggt    900
aaagccattt ggataaggt  tgaagaaaaa ttggatttga agaaagaaaa gtttgtagat    960
agtagacatg tttatctga  acacggtaac atgtcttcat ccactgtctt gttcgtaatg   1020
gatgaattga aaagagatc  attagaagag ggtaaatcta ctactggtga cggttttgaa   1080
tggggtgtct tatttggttt cggtcctggt ttgaccgtcg aaagagtagt tgtcagatca   1140
gtaccaatta aatattag                                                1158
```

<210> SEQ ID NO 26
<211> LENGTH: 315
<212> TYPE: DNA
<213> ORGANISM: Artificial Sequence
<220> FEATURE:
<223> OTHER INFORMATION: Codon optimized

<400> SEQUENCE: 26

```
atggccgtca agcatttgat agtattgaag tttaaagatg aaatcacaga agctcaaaag     60
gaagaatttt tcaagaccta cgttaatttg gtcaacatta tacctgctat gaaagatgta    120
tactggggta aagacgttac acaaaagaaa gaagaaggtt atacacacat tgtcgaagta    180
accttcgaat cagttgaaac tatccaagat tacatcattc atccagctca cgttggtttt    240
ggtgacgttt acagatccct ctgggaaaaa ttgttgatct tcgattacac cccaagaaag    300
ttaaagccaa ataa                                                     315
```

<210> SEQ ID NO 27
<211> LENGTH: 1188
<212> TYPE: DNA
<213> ORGANISM: Artificial Sequence
<220> FEATURE:
<223> OTHER INFORMATION: Codon optimized

<400> SEQUENCE: 27

```
atgggtttat catccgtctg tactttctcc ttccaaacta actatcatac cttattgaat      60
cctcacaaca acaatccaaa acatcattg ttgtgttaca gacatccaaa gacacctatt     120
aagtactctt acaacaactt ccatcaaaa cattgttcaa ccaagtcctt ccacttacaa     180
aataagtgct ccgaaagttt gtctatagct aagaactcta tcagagctgc aactacaaat    240
caaactgaac cacctgaaag tgataatcac tctgttgcca caaaattttt gaacttcggt    300
aaagcatgtt ggaagttgca agaccatac accataatcg cttttacttc ttgtgcatgc    360
ggtttattcg gtaaagaatt gttgcataac actaacttaa tttcatggtc cttgatgttc    420
aaggcatttt tcttttagt tgccatcttg tgcatcgctt cattcaccac tacaattaat    480
caaatatacg atttgcacat cgacagaatt aacaaaccag atttgccttt ggcttcaggt    540
gaaatatccg tcaatactgc atggatcatg tctatcatag tagccttgtt cggttttgatc   600
atcacaatta aaatgaaggg tggtccattg tacatcttcg ttactgtttt cggtatcttc    660
ggtggtattg tctattccgt accacctttt agatggaaac aaaaccctag tactgccttt    720
ttgttgaatt tcttagctca tatcatcaca aacttcacct tctactacgc ttcaagagct    780
gctttaggtt tgccattcga attgagacct tcattcacat ttttgttggc attcatgaaa    840
agtatgggtt ctgcattagc cttgatcaag gatgcctctg acgttgaagg tgacacaaag    900
ttcggtatta gtaccttggc ttctaagtac ggttcaagaa atttgacttt gttctgctcc    960
ggtatcgttt tgttaagtta cgtcgcagcc attttggcag gtatcatttg gccacaagcc   1020
tttaattcta acgttatgtt gttgtcacat gccatcttgg ctttctggtt gatcttgcaa   1080
actagagatt tcgctttgac aaattatgac cctgaagcag gtagaagatt ctacgagttt   1140
atgtggaaat gtactacgc tgaatatttg gtatacgttt ttattttag                1188
```

<210> SEQ ID NO 28
<211> LENGTH: 1635
<212> TYPE: DNA
<213> ORGANISM: Artificial Sequence
<220> FEATURE:
<223> OTHER INFORMATION: Codon optimized

<400> SEQUENCE: 28

```
atgaaatgtt caactttctc cttttggttc gtatgcaaga tcatcttctt tttcttttcc     60
tttaacatcc aaacaagtat cgcaaaccca agagaaaact ttttgaagtg cttctcacaa    120
tataccctaa taacgccac caatttgaag ttggtttaca ctcaaaacaa cccattgtac    180
atgtccgtct gaacagtac aatccataat ttgagattca cttctgatac cactccaaaa    240
ccttttggtca ttgtaacccc tagtcatgta tctcacatcc aaggtactat cttatgttct    300
aaaaaggttg gtttgcaaat tagaactaga tccggtggtc atgatagtga aggcatgtca    360
tacatctccc aagttccatt cgttatcgtt gatttgagaa acatgagatc aattaaaata    420
gacgtacact cacaaactgc ttgggttgaa gctggtgcaa cattgggtga agtatactac    480
tgggttaacg aaaagaatga aaacttatca ttggctgctg ttactgtcc aacagtttgc    540
gcaggtggtc attttggtgg tggtggttat ggtcctttaa tgagaaacta cggtttggcc    600
```

-continued

```
gctgataaca taatcgacgc tcatttggta aatgttcacg gtaaagtttt ggatagaaag    660
tctatgggtg aagacttatt tgggctttg agaggtggtg gtgcagaatc attcggtatc    720
atagttgctt ggaagataag attagtcgca gtaccaaagt ctactatgtt ctcagtcaaa    780
aagataatgg aaatccatga attagttaaa ttggtcaata agtggcaaaa catcgcatac    840
aagtacgata aggacttgtt gttgatgact catttcatca caagaaacat caccgataac    900
caaggtaaaa ataagactgc tatccacaca tactttcttt cagttttctt gggtggtgtc    960
gattccttag tagacttgat gaataagtct tttccagaat taggtattaa gaaaactgat   1020
tgtagacaat tgtcttggat cgacaccatc atctttattt caggtgttgt caactacgat   1080
acagacaact tcaacaaaga aatattattg gatagatccg caggtcaaaa cggtgccttt   1140
aaaattaagt tagactacgt taaaaagcca atacctgaat cagttttcgt ccaaatctta   1200
gaaaaattgt acgaagaaga tattggtgca ggcatgtacg ccttgtatcc atacggtggt   1260
ataatggacg aaatcagtga atctgccatt ccatttcctc atagagctgg tatcttatac   1320
gaattgtggt acatttgttc atgggaaaag caagaagata cgaaaagca cttaaactgg   1380 attagaaaca tctataactt catgactcca tacgtttcta aaaaccctag attggcatat   1440
ttgaactaca gagatttgga catcggtatt aacgatccaa agaatcctaa caactatacc   1500
caagctagaa tttggggtga aaatacttc ggtaaaaatt tcgatagatt agtaaaggtt   1560
aagacattgg ttgacccaaa caacttctt agaaacgaac aatccattcc accttttacct  1620 agacatagac actga                                                   1635
```

<210> SEQ ID NO 29
<211> LENGTH: 1638
<212> TYPE: DNA
<213> ORGANISM: Artificial Sequence
<220> FEATURE:
<223> OTHER INFORMATION: Codon optimized

<400> SEQUENCE: 29

```
atgaactgct ccgcattctc tttctggttc gtctgtaaaa taatcttctt cttcttgtcc    60
ttcaacatcc aaatctccat cgcaaatcca aagaaaaact ttttgaagtg tttctccgaa   120
tacatcccaa acaaccctgc taacccaaag tttatatata ctcaacatga tcaattgtac   180
atgtccgttt tgaacagtac catccaaaat ttgagattca cttctgacac tacaccaaaa   240
cctttagtca ttgttacacc ttccaatgtt agtcacattc aagcttctat attgtgctct   300
aagaaagtag gtttgcaaat cagaactaga tcaggtggtc atgatgcaga aggcatgtct   360
tacatctcac aagttccatt cgttgtagtc gatttgagaa atatgcattc cataaagatc   420
gacgttcaca gtcaaacagc atgggtagaa gcaggtgcca ccttgggtga agtttactac   480
tggatcaacg aaaagaatga aaacttttct ttccctggtg gttactgtcc aacagtaggt   540
gtcggtggtc acttttctgg tggtggttat ggtgcattga tgagaaacta cggtttagct   600
gcagataata ttatagacgc ccatttggtt aacgtagatg gtaaagtttt ggacagaaag   660
tctatgggtg aagatttgtt tgggccata agaggtggtg gtggtgaaaa tttcggtatc   720
attgccgctt ggaaaattaa gttagtcgct gttccttcca aagtactat tttctctgtc   780 aaaaagaaca tggaaatcca cggtttggtt aagttgttta ataagtggca aaacatcgct   840
tacaagtacg ataaggactt ggttttgatg acccatttca tcactaaaaa tattacagat   900
aaccatggta aaataagac cactgttcac ggttattttt cttcaatttt ccatggtggt   960
```

```
gtagattctt tggttgattt gatgaataag tcattcccag aattgggtat taaaaagaca    1020
gattgcaagg aattttcttg gatagacaca accatcttct attcaggtgt tgtaaacttc    1080
aacaccgcta acttcaaaaa ggaaatcttg ttggatagat ccgctggtaa aaagaccgct    1140
ttttctatta aattggacta cgttaagaaa ccaatccctg aaactgcaat ggtcaagata    1200
ttggaaaagt tgtacgaaga agatgtaggt gtcggcatgt acgttttgta tccatacggt    1260
ggtattatgg aagaaatatc tgaatcagcc ataccatttc ctcacagagc tggtatcatg    1320
tatgaattat ggtacacagc ctcatgggaa aagcaagaag ataacgaaaa gcatatcaac    1380
tgggtcagat ccgtttacaa cttcactaca ccttacgtta gtcaaaaccc aagattggca    1440
tatttgaact acagagattt ggacttaggt aaaactaacc ctgaatctcc aaataactat    1500
acacaagcaa gaatttgggg tgaaaagtac tttggtaaaa atttcaacag attagttaaa    1560
gtaaagacta agccgaccc taacaacttt ttcagaaacg aacaatccat cccacctttg    1620
ccacctcacc accactaa                                                  1638

<210> SEQ ID NO 30
<211> LENGTH: 42
<212> TYPE: DNA
<213> ORGANISM: Artificial Sequence
<220> FEATURE:
<223> OTHER INFORMATION: Primer

<400> SEQUENCE: 30
aggaaacgaa gataaatctc gagtttatca ttatcaatac tg                       42

<210> SEQ ID NO 31
<211> LENGTH: 37
<212> TYPE: DNA
<213> ORGANISM: Artificial Sequence
<220> FEATURE:
<223> OTHER INFORMATION: Primer

<400> SEQUENCE: 31
ggaaaaatca gtcaaggcaa attaaagcct tcgagcg                             37

<210> SEQ ID NO 32
<211> LENGTH: 27
<212> TYPE: DNA
<213> ORGANISM: Artificial Sequence
<220> FEATURE:
<223> OTHER INFORMATION: Primer

<400> SEQUENCE: 32
gatgggggat ccactagttc tagaatc                                        27

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
tgatgggctg caggaattcg atatc                                          25

<210> SEQ ID NO 34
<211> LENGTH: 38
<212> TYPE: DNA
<213> ORGANISM: Artificial Sequence
<220> FEATURE:
<223> OTHER INFORMATION: Primer
```

<400> SEQUENCE: 34
gaactagtgg atccccatc atgaaccatt tgagagcc					38

<210> SEQ ID NO 35
<211> LENGTH: 32
<212> TYPE: DNA
<213> ORGANISM: Artificial Sequence
<220> FEATURE:
<223> OTHER INFORMATION: Primer

<400> SEQUENCE: 35
tattttggct ttaactttct tggggtgtaa tc					32

<210> SEQ ID NO 36
<211> LENGTH: 43
<212> TYPE: DNA
<213> ORGANISM: Artificial Sequence
<220> FEATURE:
<223> OTHER INFORMATION: Primer

<400> SEQUENCE: 36
agaaagttaa agccaaaata atgataacga gaataatatc aag					43

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
ataaacccat ggcgcagacc tgtgagag					28

<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38
ggtctgcgcc atgggtttat catccgtc					28

<210> SEQ ID NO 39
<211> LENGTH: 41
<212> TYPE: DNA
<213> ORGANISM: Artificial Sequence
<220> FEATURE:
<223> OTHER INFORMATION: Primer

<400> SEQUENCE: 39
cgaattcctg cagcccatca gtgtctatgt ctaggtaaag g					41

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
tgatgggctg caggaattcg atatc					25

<210> SEQ ID NO 41

<211> LENGTH: 27
<212> TYPE: DNA
<213> ORGANISM: Artificial Sequence
<220> FEATURE:
<223> OTHER INFORMATION: Primer

<400> SEQUENCE: 41
gatgggggat ccactagttc tagaatc                                    27

<210> SEQ ID NO 42
<211> LENGTH: 33
<212> TYPE: DNA
<213> ORGANISM: Artificial Sequence
<220> FEATURE:
<223> OTHER INFORMATION: Primer

<400> SEQUENCE: 42
caccagaacc gaaggtagag gttctttgtt aac                             33

<210> SEQ ID NO 43
<211> LENGTH: 45
<212> TYPE: DNA
<213> ORGANISM: Artificial Sequence
<220> FEATURE:
<223> OTHER INFORMATION: Primer

<400> SEQUENCE: 43
cgaattcctg cagcccatca ctttgatctc ttgtagacct tattc                45

<210> SEQ ID NO 44
<211> LENGTH: 42
<212> TYPE: DNA
<213> ORGANISM: Artificial Sequence
<220> FEATURE:
<223> OTHER INFORMATION: Primer

<400> SEQUENCE: 44
gaactagtgg atcccccatc atggtttcca atcacttgtt tg                   42

<210> SEQ ID NO 45
<211> LENGTH: 29
<212> TYPE: DNA
<213> ORGANISM: Artificial Sequence
<220> FEATURE:
<223> OTHER INFORMATION: Primer

<400> SEQUENCE: 45
ctctaccttc ggttctggtg tataagtcg                                  29

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
gatccactag ttctagaatc cg                                         22

<210> SEQ ID NO 47
<211> LENGTH: 35
<212> TYPE: DNA
<213> ORGANISM: Artificial Sequence
<220> FEATURE:
<223> OTHER INFORMATION: Primer

<400> SEQUENCE: 47

-continued

<210> SEQ ID NO 48
<211> LENGTH: 28
<212> TYPE: DNA
<213> ORGANISM: Artificial Sequence
<220> FEATURE:
<223> OTHER INFORMATION: Primer

<400> SEQUENCE: 48
tcgttatcac tttcttgggg tgtaatcg                                        28

<210> SEQ ID NO 49
<211> LENGTH: 36
<212> TYPE: DNA
<213> ORGANISM: Artificial Sequence
<220> FEATURE:
<223> OTHER INFORMATION: Primer

<400> SEQUENCE: 49
ccaagaaagt gataacgaga ataatatcaa gaatac                               36

<210> SEQ ID NO 50
<211> LENGTH: 44
<212> TYPE: DNA
<213> ORGANISM: Artificial Sequence
<220> FEATURE:
<223> OTHER INFORMATION: Primer

<400> SEQUENCE: 50
aggtcgacgg tatcgttaaa taaaaacgta taccaaatat tcag                      44

<210> SEQ ID NO 51
<211> LENGTH: 18
<212> TYPE: DNA
<213> ORGANISM: Artificial Sequence
<220> FEATURE:
<223> OTHER INFORMATION: Primer

<400> SEQUENCE: 51
cgataccgtc gacctcga                                                   18

<210> SEQ ID NO 52
<211> LENGTH: 32
<212> TYPE: DNA
<213> ORGANISM: Artificial Sequence
<220> FEATURE:
<223> OTHER INFORMATION: Primer

<400> SEQUENCE: 52
ggttaaacta gtatgggtaa aaactataag tc                                   32

<210> SEQ ID NO 53
<211> LENGTH: 33
<212> TYPE: DNA
<213> ORGANISM: Artificial Sequence
<220> FEATURE:
<223> OTHER INFORMATION: Primer

<400> SEQUENCE: 53
gtgcccgtcg actcattcga aatgactgaa ttg                                  33